United States Patent [19]

Kohn et al.

[11] Patent Number: 5,378,729

[45] Date of Patent: Jan. 3, 1995

[54] AMINO ACID DERIVATIVE ANTICONVULSANT

[75] Inventors: Harold L. Kohn, Houston; Darrell Watson, Belton, both of Tex.

[73] Assignee: Research Corporation Technologies, Inc., Tucson, Ariz.

[21] Appl. No.: 710,610

[22] Filed: Jun. 4, 1991

Related U.S. Application Data

[63] Continuation-in-part of Ser. No. 354,057, May 19, 1989, abandoned, and Ser. No. 392,870, Aug. 11, 1989, abandoned, which is a continuation of Ser. No. 80,528, Jul. 31, 1987, abandoned, which is a continuation-in-part of Ser. No. 916,254, Oct. 7, 1986, abandoned, which is a continuation-in-part of Ser. No. 702,195, Feb. 15, 1985, abandoned, said Ser. No. 354,057, is a continuation-in-part of Ser. No. 80,528, Feb. 15, 1985.

[51] Int. Cl.$^6$ .............. A61K 31/535; A61K 31/445; C07D 211/72; C07D 261/04
[52] U.S. Cl. ................... 514/231.2; 514/315; 514/397; 514/406; 514/415; 514/424; 514/461; 514/468; 514/486; 546/292; 548/371.4; 548/245; 564/148; 564/152; 564/154
[58] Field of Search .............. 564/148, 155, 154, 152; 548/616, 245, 371.4; 514/461, 548, 549; 546/292

[56] References Cited

U.S. PATENT DOCUMENTS

| | | | |
|---|---|---|---|
| 2,676,188 | 4/1954 | Bruce et al. | 564/155 |
| 2,721,197 | 10/1955 | Sheehan | 564/155 |
| 3,340,147 | 9/1967 | Martin et al. | 514/616 |
| 3,657,341 | 4/1972 | Thorne et al. | 260/558 A |
| 3,707,559 | 12/1972 | Mazur et al. | 564/158 |
| 4,018,826 | 4/1977 | Gless, Jr. et al. | 564/215 |
| 4,260,684 | 4/1981 | Schult | 564/155 |
| 4,303,673 | 12/1981 | Biedermann et al. | 564/155 |
| 4,513,009 | 4/1985 | Roques et al. | 564/155 |
| 4,595,700 | 6/1986 | Donald et al. | 514/616 |
| 4,618,708 | 10/1986 | Roques et al. | 564/154 |
| 4,873,241 | 10/1989 | Napier et al. | 514/237.8 |

FOREIGN PATENT DOCUMENTS

| | | |
|---|---|---|
| 0885303 | 3/1981 | Belgium . |
| 0194464 | 2/1980 | European Pat. Off. . |
| 0007441 | 10/1980 | European Pat. Off. . |
| 0038758 | 10/1981 | European Pat. Off. . |
| 0042626 | 12/1981 | European Pat. Off. . |
| 0046707 | 3/1982 | European Pat. Off. . |
| 0263506 | 10/1987 | European Pat. Off. . |
| 0400400 | 5/1990 | European Pat. Off. . |
| 1927692 | 12/1969 | Germany . |
| 0393355 | 10/1965 | Switzerland . |
| 1051220 | 12/1966 | United Kingdom . |

OTHER PUBLICATIONS

Chemical Abstracts, vol. 92; No. 7:51712r (Feb. 18, 1990).

Chemical Abstracts, vol. 96; No. 5:35710r (Feb. 1, 1982).

Chemical Abstracts, vol. 101; No. 9; 72124v (Aug. 27, 1984).

Chemical Abstracts, vol. 91; No. 21:175147; (Nov. 19, 1979).

(List continued on next page.)

Primary Examiner—Marianne M. Cintins
Assistant Examiner—T. Criares
Attorney, Agent, or Firm—Scully, Scott, Murphy & Presser

[57] ABSTRACT

The present invention relates to compounds exhibiting central nervous system (CNS) activity which are useful in the treatment of epilepsy and other CNS disorders. The compounds of this invention have the following general formula:

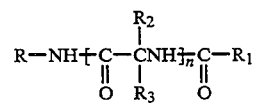

and pharmaceutically acceptable salts thereof.

150 Claims, No Drawings

OTHER PUBLICATIONS

Kohn, et al. (1988) Brain Research 457: 371–375, Marked Sterospecificity in a New Class of Anticonvulsants.

Chemical Abstracts, vol. 97; 145266d (1982).

White, et al. (1981) JACS, 103:4231–4239, Active-Site-Directed Inhibition of alpha-Chymotrypsin by Deaminatively Produced Carbonium Ions: An Example of Suicide of Enzyme-Activated-Substrate Inhibition.

Legall, et al. (1988) Int. J. Protein Res., 12:279–291 Synthesis of Functionalized Non-Natural Amino Acid Derivatives via Amidoalkylation Transformations.

Conley, et al. (1987) J. Med. Chem., 30(3):574–580, Functionalized DL-Amino Acid Derivatives, Potent New Agents for the Treatment of Epilepsy.

Garcia, et al. (1984) Tetrahedron Letters, 25(42) 4841–4844, New Synthetic "Tricks" Triphenylphosphine-Mediated Amide Formation from Carboxylic Acids and Azides.

Rebek, et al. (1979), J. Am. Chem. Soc., 101(3):737, On the Rate of Site-Site Interactions in Functionalized Polystyrenes.

Cortes, et al. (1985) J. Med. Chem., 28:601–606, Effect of Structural Modification of the Hydantion Ring on Anticonvulsant Activity.

Ikeda, et al. (1977) Tetrahedron, 33(5): 489–495, Photochemical Synthesis of 1,2,3,4-Tetrahydroisoquinolin-3-ones from N-Chloroacetylbenzylamines.

Katritzky, et al. (1990) J. Org. Chem. 55: 2206–2214, Benzotriazole-Assisted Synthesis of Monoacyl Animals and Their Peptide Derivatives.

Lipshutz et al. (1983) J. Am. Chem. Soc. 105; 7703–7713, Heterocycles as Masked Diamide/Dipeptide Equivalents, Formation and Reactions of Substituted 5-(Acylamino) Oxazoles as Intermediates en Route to the Cyclopeptide Alkaloids.

Lipshutz et al. (1983) J. Org. Chem. 48:3745–3750, An Approach to the Cyclopeptide Alkaloids (Phenylcyclopeptines) via Heterocyclic Diamide/Dipeptide Equivalents, Preparation and N-Alkylation Studies of 2,4(5)-Disubstituted Imidazoles.

Rogues, (1987) 193rd ACS National Meeting Amer. Chem. Society, Apr. 15–10, 1987, Use of Various Metallopeptidase Inhibitors to Study the Physilogical Rate of Endogenous Neuropeptides.

Kohn, et al. (1990) J. Med Chem. 33:919–926, Preparation and Anticonvulsant Activity of a Series of Functionalized $\beta$-Aromatic and $\alpha$ Heteroaromatic Amino Acids.

Lipshutz et al. "Heterocycles in Synthesis . . . Imidazoles" Journal of the American Chemical Society, vol. 106, No. 2, pp. 457–459 CA 102(19): 160030n (1985).

AMINO ACID DERIVATIVE ANTICONVULSANT

This invention was made with Government support under NS15604 awarded by the National Institutes of Health. The Government has certain rights in the invention.

The present application is a continuation-in-part of copending U.S. patent application Ser. No. 07/354,057 filed on May 9, 1989 and a CIP of U.S. patent application Ser. No. 07/392,870 filed on Aug. 11, 1989 both now abandoned. U.S. patent application Ser. No. 07/354,057 filed on May 19, 1989, now abandoned being a continuation-in-part of U.S. patent application having Ser. No. 07/080,528, filed on Jul. 31, 1987 now abandoned, which is a continuation-in-part of U.S. patent application Ser. No. 06/916,254, filed Oct. 7, 1986, now abandoned which is a continuation-in-part of U.S. patent application Ser. No. 06/702,195, filed Feb. 15, 1985 now abandoned said U.S. patent application Ser. No. 07/392,870 filed Jul. 11, 1989, abandoned being a continuation application of U.S. patent application having Ser. No. 07/080,528, filed on Jul. 31, 1987, now abandoned, which is a continuation-in-part of U.S. patent application Ser. No. 06/916,254, filed Oct. 7, 1986, now abandoned, which is a continuation-in-part of U.S. patent application Ser. No. 06/702,195 filed on Feb. 15, 1985 now abandoned.

The present invention relates to compounds and pharmaceutical compositions having central nervous system (CNS) activity which are useful in the treatment of epilepsy and other CNS disorders. More specifically, the compounds of this invention can be characterized as protected amino acid derivatives having the following general formula:

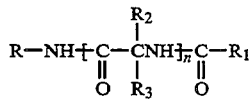

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group, or electron donating group;

$R_1$ is hydrogen or lower alkyl, lower alkenyl, lower alkynyl, aryl lower alkyl, aryl, heterocyclic lower alkyl heterocyclic, lower cycloalkyl, lower cycloalkyl lower alkyl, each unsubstituted or substituted with an electron donating group or an electron withdrawing group and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, $S(O)_a$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, lower alkyl and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$ or $PR_4SR_7$, $NR_4PR_5R_6$ or $PR_4NR_5R_7$,

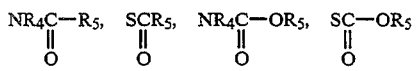

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group and $R_7$ is $R_6$ or $COOR_8$ or $COR_8$ $R_8$ is hydrogen or lower alkyl, or aryl lower alkyl, and the aryl or alkyl group may be unsubstituted or substituted with an electron withdrawing group or an electron donating group and n is 1-4 and a is 1-3.

The predominant application of anticonvulsant drugs is the control and prevention of seizures associated with epilepsy or related central nervous system disorders. Epilepsy refers to many types of recurrent seizures produced by paroxysmal excessive neuronal discharges in the brain; the two main generalized seizures are petit mal, which is associated with myoclonic jerks, akinetic seizures, transient loss of consciousness, but without convulsion; and grand mal which manifests in a continuous series of seizures and convulsions with loss of consciousness.

The mainstay of treatment for such disorders has been the long-term and consistent administration of anticonvulsant drugs. Most drugs in use are weak acids that, presumably, exert their action on neurons, glial cells or both of the central nervous system. The majority of these compounds are characterized by the presence of at least one amide unit and one or more benzene rings that are present as a phenyl group or part of a cyclic system.

Much attention has been focused upon the development of anticonvulsant drugs and today many such drugs are well known. For example, the hydantions, such as phenytoin, are useful in the control of generalized seizures and all forms of partial seizures. The oxazolidinediones, such as trimethadione and paramethadione, are used in the treatment of nonconvulsive seizures. Phenacemide, a phenylacetylurea, is one of the most well known anticonvulsants employed today, while much attention has recently been dedicated to the investigation of the diazepines and piperazines. For example, U.S. Pat. Nos. 4,002,764 and 4,178,378 to Allgeier, et al. disclose esterified diazepine derivatives useful in the treatment of epilepsy and other nervous disorders. U.S. Pat. No. 3,887,543 to Nakanishi, et al. describes a thieno [2,3-e][1,4]diazepine compound also having anticonvulsant activity and other depressant activity. U.S. Pat. No. 4,209,516 to Heckendorn, et al. relates to triazole derivatives which exhibit anticonvulsant activity and are useful in the treatment of epilepsy and conditions of tension and agitation. U.S. Pat. No. 4,372,974 to Fish, et al. discloses a pharmaceutical formulation containing an aliphatic amino acid compound in which the carboxylic acid and primary amine are separated by three or four units. Administration of these compounds in an acid pH range are useful in the treatment of convulsion disorders and also possess anxiolytic and sedative properties.

Unfortunately, despite the many available pharmacotherapeutic agents, a significant percentage of the population with epilepsy or related disorders are poorly managed. Moreover, none of the drugs presently available are capable of achieving total seizure control and most have disturbing side-effects. Clearly, current therapy has failed to "seize control" of these debilitating diseases.

It is therefore one object of the present invention to provide novel compounds exhibiting CNS activity, particularly anticonvulsant activity.

Another object of this invention is to provide pharmaceutical compositions useful in the treatment of epilepsy and other CNS disorders.

A further object of this invention is to provide a method of treating epilepsy and related convulsant disorders.

These and other objects are accomplished herein by providing compounds of the following general formula:

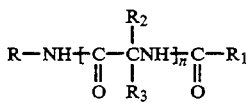

wherein R, $R_1$, $R_2$, $R_3$, $R_4$, $R_5$, $R_6$, $R_7$, $R_8$, n, Z, Y are as defined hereinabove.

The present invention contemplates employing the compounds of Formula I in compositions of pharmaceutically acceptable dosage forms. Where the appropriate substituents are employed, the present invention also includes pharmaceutically acceptable addition salts. Moreover, the administration of an effective amount of the present compounds, in their pharmaceutically acceptable forms or the addition salts thereof, can provide an excellent regime for the treatment of epilepsy, nervous anxiety, psychosis, insomnia and other related central nervous disorders.

The alkyl groups when used alone or in combination with other groups, are lower alkyl containing from 1 to 6 carbon atoms and may be straight chain or branched. These groups include methyl, ethyl, propyl, isopropyl, butyl, isobutyl, tertiary butyl, amyl, hexyl, and the like.

The aryl lower alkyl groups include, for example, benzyl, phenethyl, phenpropyl, phenisopropyl, phenbutyl, and the like, diphenylmethyl, 1,1-diphenylethyl, 1,2-diphenylethyl, and the like.

The term aryl, when used along or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polycyclic and are fused rings. Polynuclear aromatic compound is meant to encompass bicyclic, tricyclic fused aromatic ring system containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl.

Lower alkenyl is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E-)-4-methyl-2-pentenyl, pentadienyl, e.g., 1,3 or 2,4-pentadienyl, and the like.

The term alkynyl include alkyene substituents containing 2 to 6 carbon atoms and may be straight chained as well as branched. It includes such groups as ethynyl, propynyl, 1-butynyl, 2-butynyl, 1-pentynl, 2-pentynyl, 3-methyl-1-pentynyl, 3-pentynyl, 1-hexynyl, 2-hexynyl, 3-hexynyl and the like.

The term cycloalkyl when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Furthermore, the substituents may either be in endo or exo positions in the bridged bicyclic systems.

The term "electron-withdrawing and electron donating" refer to the ability of a substituent to withdraw or donate electrons relative to that of hydrogen if the hydrogen atom occupied the same position in the molecule. These terms are well understood by one skilled in the art and are discussed in *Advanced Organic Chemistry*, by J. March, John Wiley and Sons, New York N.Y., pp. 16–18 (1985) and the discussion therein is incorporated herein by reference. Electron withdrawing groups include halo, including br .o, fluoro, chloro, iodo and the like; nitro, carboxy, ᴊwer alkenyl, lower alkynyl, formyl, carboxyamido, ıryl, quaternary ammonium, trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One skilled in the art will appreciate that the aforesaid substituents may have electron donating or electron withdrawing properties under different chemical conditions. Moreover, the present invention contemplates any combination of substituents selected from the above-identified groups.

The term halo includes fluoro, chloro, bromo, iodo and the like.

The term acyl includes lower alkanoyl.

As employed herein, the heterocyclic substituent contains at least one sulfur, nitrogen or oxygen, but also may include one or several of said atoms. The heterocyclic substituents contemplated by the present invention include heteroaromatics and saturated and partially saturated heterocyclic compounds. These heterocyclics may be monocyclic, bicyclic, tricyclic or polycyclic and are fused rings. They may contain up to 18 ring atoms and up to a total of 17 ring carbon atoms and a total of up to 25 carbon atoms. The heterocyclics are also intended to include the so-called benzoheterocycles. Representative heterocyclics include furyl, thienyl, pyrazolyl, pyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolidinyl, imidazolinyl, imadazolidinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the nitric oxides of pyridyl, pyrazinyl, and pyrimidinyl and the like. The preferred heterocyclic are thienyl, furyl, pyrrolyl, benzofuryl, benzothienyl, indolyl, methylpyrrolyl, morpholinyl, pyridyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclic is furyl and pyridyl.

The preferred compounds are those wherein n is 1, but di, tri and tetrapeptides are also contemplated to be within the scope of the claims.

The preferred values of R is aryl lower alkyl, especially benzyl, and the preferred $R_1$ is H or lower alkyl. The most preferred $R_1$ group is methyl.

The most preferred electron donating substituent and electron withdrawing substituent are halo, nitro, alkanoyl, formyl, arylalkanoyl, aryloyl, carboxyl, carbalkoxy, carboxamide, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl)amino, amino lower alkyl mercapto, mercaptoalkyl, alkylthio; and alkyldithio. The term "sulfide" encompasses mercapto, mercapto alkyl and alkylthio, while the term disulfide encompasses alkyldithio. These preferred substituents may be substituted on any one of $R_1$, $R_2$, $R_3$, $R_4$, $R_5$ or $R_6$, $R_7$ or $R_8$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino, alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein $R_{18}$ is lower alkyl], N-lower alkylhydroxyl amino [(NR$_{18}$)OH wherein $R_{18}$ is lower alkyl], N-lower alkyl-O-lower alkyl hydroxyamino, i.e., [N(R$_{18}$)OR$_{19}$ wherein $R_{18}$ and $R_{19}$ are independently lower alkyl] and o-hydroxylamino (—O—NH$_2$); alkylamido such as acetamido, trifluoroacetamido, lower alkoxyamino, (e.g. NH(OCH$_3$); and heterocyclicamino, such as pyrazoylamino.

The hetereocyclic groups representative of $R_2$ and $R_3$ have the formula

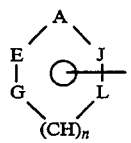

XI or those corresponding partially or fully saturated form thereof wherein n is 0 or 1

A, Z, L and J are independently CH, or a heteroatom selected from the group consisting of N, O, S, and G is CH, or a heteroatom selected from the group consisting of N, O and S, but when n is O, G is CH, or a heterocyclic selected from the group consisting of NH, O and S with the proviso that at most two of A, E, L, J and G are heteroatoms.

If the ring depicted hereinabove contains a nitrogen ring atom, then the N-oxide forms are also contemplated to be within the scope of the invention.

When $R_2$ or $R_3$ is a heterocyclic of the above formula, it may be bonded to the main chain by a ring carbon atom. When n is O, $R_2$ or $R_3$ may additionally be bonded to the main chain by a nitrogen ring atom.

It is preferred that one of $R_2$ and $R_3$ is hydrogen

In a preferred embodiment, one of $R_2$ and $R_3$ is hydrogen and that the other is heterocyclic. It is preferred that one of $R_2$ and $R_3$ is a heterocyclic having Formula XI. The preferred heterocyclics include furyl, thienyl, benzothienyl, benzofuryl, oxazolyl, thiazolyl, isoxazolyl, indolyl, pyrazolyl, isoxazolidinyl, benzothienyl, benzofuryl, morpholinyl, indolyl, pyrrolyl, furfuryl, and methylpyrrolyl, pyridyl, pyrazinyl, imidazolyl, pyrimidinyl or pyridazinyl. In another preferred embodiment, one of $R_2$ and $R_3$ is alkyl (e.g. methylisopropyl), aryl (e.g., phenyl), 2-thiomethylethyl, lower alkoxy (e.g., ethoxy, methoxy), anilino, propenyl, alkylamino (e.g., ethylamino or methylamino). In another preferred embodiment, one of $R_2$ and $R_3$ is hydrogen and the other is heterocyclic lower alkyl, lower alkenyl, amino, lower alkoxy amino, N-lower alkylhydroxyamino, lower alkoxyamino, N-lower alkyl-O-lower alkylhydroxyamino or aralkoxycarbonylhydrazino, Preferred compounds of the present invention have the following general formula:

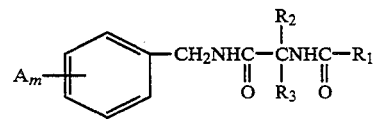

wherein $R_1$ is H or lower alkyl, $R_2$ and $R_3$ are as defined above and A is hydrogen or an electron donating group or electron-withdrawing group and m is 0-5. It is preferred that A is hydrogen (i.e., m=0). However, values of m equalling 1, 2 or 3 are also preferred.

Preferred embodiments include compounds of Formula I

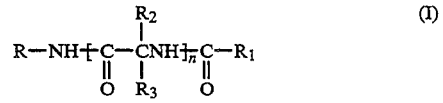

(I)

wherein R and $R_1$, independently, are hydrogen, lower alkyl, lower alkenyl, lower alkynyl, aryl lower alkyl, aryl, heterocyclic, lower alkyl heterocyclic, each unsubstituted or substituted with at least one substituent;

$R_2$ and $R_3$, independently, are hydrogen, lower alkyl, lower alkenyl, lower alkynyl, aryl lower alkyl, aryl, heterocyclic, lower alkyl heterocyclic, each unsubstituted or substituted with at least one substituent; halogen or a heteroatom containing oxygen, nitrogen, sulfur or phosphorous substituted with hydrogen, lower alkyl or aryl, said lower alkyl or aryl groups being substituted or unsubstituted; and n is 1 to 4.

Another preferred embodiment is a compound having Formula I

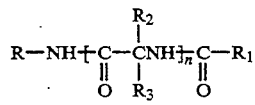

(I)

wherein R is aryl, aryl lower alkyl, heterocyclic, lower alkyl heterocyclic, polynuclear aromatic or lower alkyl polynuclear aromatic, each unsubstituted or substituted with at least one electron withdrawing substituent or at least one electron donating substituent;

$R_1$ is H or lower alkyl, unsubstituted or substituted with at least one electron withdrawing substituent or at least one electron donating substituent;

$R_2$ and $R_3$, independently, are hydrogen, lower alkyl, lower alkenyl, lower alkynyl, aryl, aryl lower alkyl, heterocyclic, lower alkyl heterocyclic, polynuclear aromatic, lower alkyl polynuclear aromatic, each unsubstituted or substituted with at least one electron donating substituent, halogen or a heteroatom containing oxygen, nitrogen, sulfur or phosphorous substituted with hydrogen, lower alkyl or aryl, said lower alkyl or aryl groups being substituted or unsubstituted; and n is 1 to 4.

Another preferred embodiment of the present invention is a compound of Formula I

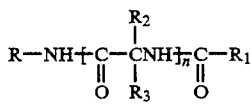

wherein R is aryl lower alkyl, heterocyclic, lower alkyl heterocyclic, polynuclear aromatic or lower alkyl polynuclear aromatic, each of which may be unsubstituted or substituted with at least one halo, nitro, acyl, carboxyl, carboalkoxy, carboxamide, cyano, sulfonyl, sulfoxide (sulfinyl), heterocyclic, guanidine, quaternary ammonium hydroxy, alkoxy, alkyl, amino, phenoxy, mercapto, sulfide or disulfide;

$R_1$ is H or lower alkyl which may be unsubstituted or substituted with at least one halo, nitro, acyl, carboxamide, cyano, sulfonyl, sulfoxide (sulfinyl), heterocyclic, guanidine, quaternary ammonium, hydroxy, lower alkoxy, amino, phenoxy, sulfide, or disulfide;

$R_2$ is hydrogen, lower alkyl, lower alkenyl, lower alkynyl, aryl, heterocyclic, lower alkyl heterocyclic, polynuclear aromatic, lower alkyl polynuclear aromatic, each unsubstituted or substituted with at least one electron withdrawing substituent or at least one electron donating substituent; halogen or a heteroatom consisting of oxygen, nitrogen, sulfur or phosphorous, said heteroatom being substituted with hydrogen, lower alkyl or aryl, said lower alkyl or aryl groups being substituted or unsubstituted;

$R_3$ is hydrogen, lower alkyl, lower alkenyl, lower alkynyl, aryl, heterocyclic, lower alkyl heterocyclic, polynuclear aromatic, lower alkyl polynuclear aromatic, each unsubstituted or substituted with at least one electron withdrawing substituent or at least one electron donating substituent; halogen or a heteroatom consisting of oxygen, nitrogen, sulfur, or phosphorous said heteroatom being substituted with hydrogen, lower alkyl or aryl, said lower alkyl or aryl groups being substituted or unsubstituted;
and n is 1 to 4;

Another preferred embodiment is a compound of Formula I

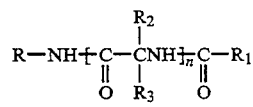

(I)

wherein R is aryl, aryl lower alkyl, heterocyclic or heterocyclic lower alkyl and R is unsubstituted or is substituted with at least one electron withdrawing group, or electron donating group;

$R_1$ is hydrogen or lower alkyl, unsubstituted or substituted with an electron donating group or an electron withdrawing group and $R_2$ and $R_3$ are independently hydrogen, lower alkyl, lower alkenyl, lower alkynyl, aryl lower alkyl, aryl, heterocyclic, heterocyclic lower alkyl, or Z-Y wherein $R_2$ and $R_3$ may be unsubstituted or substituted with at least one electron withdrawing group or electron donating group;

Z is O, $S,S(O)_a$, $NR_4$, $PR_4$ or a chemical bond;

Y is hydrogen, lower alkyl, aryl, aryl lower alkyl, lower alkenyl, lower alkynyl, heterocyclic, heterocyclic lower alkyl, or halo and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$ or $PR_4SR_7$, $NR_4PR_5R_6$ or $PR_4R_5R_7$,

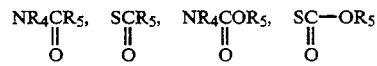

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group-and $R_7$ is $R_6$ or $COOR_8$ or $COR_8$, $R_8$ is hydrogen or lower alkyl, or aryl lower alkyl, wherein the aryl or lower alkyl groups may be unsubstituted or substituted with an electron withdrawing or electron donating group, n is 1–4 and a is 1–3.

Another class of preferred compounds of the Formula I have the formula

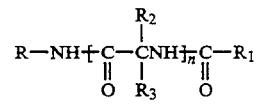

wherein R is aryl, aryl lower alkyl, heterocyclic or heterocyclic alkyl which is unsubstituted or substituted with at least one electron withdrawing group or at least one electron donating group;

$R_1$ is hydrogen or lower alkyl which is unsubstituted or substituted with at least one electron withdrawing group or one electron donating group, $R_2$ and $R_3$ are independently hydrogen, lower alkenyl, lower alkynyl, aryl, aryl lower alkyl, Z-Y or a heterocyclic group which may be unsubstituted or substituted with at least one electron withdrawing or one electron donating group, with the proviso that $R^2$ and $R^3$ cannot both be hydrogen;

Z is O, S, $NR_4$, $PR_4$ or a chemical bond;

Y is hydrogen, lower alkyl, aryl, aryl lower alkyl, lower alkenyl, lower alkynyl or halo, and Y may be unsubstituted or substituted with an electron donating group or an electron withdrawing group, provided that when Y is halo, Z is a chemical bond; or ZY taken together is $NR_4NR_5R_6$, $NR_4OR_5$, $ONR_4R_5$, $OPR_4R_5$, $PR_4OR_5$, $SNR_4R_5$, $NR_4SR_5$, $SPR_4R_5$, or $PR_4SR_5$, $NR_4PR_5R_6$ or $PR_4NR_5R_6$, $R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group;

n is 1–4.

Of this preferred group, it is especially preferred that n is 1.

The preferred compounds are those in which R is aryl, aryl lower alkyl, heterocyclic, or heterocyclic lower alkyl, $R_1$ is hydrogen or lower alkyl, $R_2$ and $R_3$ are independently hydrogen, heterocyclic, lower alkyl, aryl, lower alkoxy, lower alkenyl, amino, hydroxylamino, lower alkoxy amino, N-lower alkyl hydroxyamino, N-lower alkyl-O-lower alkyl hydroxyamino, aralkoxy carbonyl hydrazino or alkylmercapto and n is 1.

In another preferred embodiment, n is 1, R and $R_1$ are as defined hereinabove and one of $R_2$ and $R_3$ is hydrogen and the other is heterocyclic, heterocyclic lower alkyl, aryl N-hydroxylamino, lower alkoxyamino, N-lower alkylhydroxylamino, N-lower alkyl-O-lower alkylhydroxyamino.

Another preferred embodiment is wherein n is 1, R and $R_1$ are as defined hereinabove, one of $R_2$ and $R_3$ is as defined hereinabove or the other is heterocyclic, heterocyclic lower alkyl, lower alkyl heterocyclic, aryl, N-hydroxylamino, lower alkoxy amino, N-lower alkyl hydroxylamino, N-lower alkyl-O-lower alkyl hydroxylamino, lower alkoxy, dialkyl lower amino, lower alkylamino, aryl lower alkylcarbonyl hydrazino, or lower alkylmercapto.

The various combination and permutations of the Markush groups of $R_1$, $R_2$, $R_3$ R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$ and R with respect to each value of n.

The compounds of the present invention may contain one (1) or more asymmetric carbons and may exist in racemic and optically active forms. The configuration around each asymmetric carbon can be in either the D or L form. (It is well known in the art that the configuration around a chiral carbon atoms can also be described as R or S in the Cahn-Prelog-Ingold nomenclature system). All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atoms to which the groups $R_2$ and $R_3$ are attached as substituted. When n is 1, the compounds of the present invention is of the formula

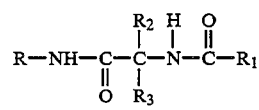

wherein R, $R_1$, $R_2$, $R_3$, $R_4$, $R_5$, $R_6$, Z and Y are as defined previously. As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the stereoisomer, including all possible enantiomers and diastereomers. The compounds of the present invention are directed to all of the optical isomers, i.e., the compounds of the present invention are either the L-stereoisomer or the D-stereoisomer. These stereoisomers may be found in mixtures of the L and D stereoisomer, e.g., racemic mixtures. The D stereoisomer is preferred.

Depending upon the substituents, the present compounds may form addition salts as well. All of these forms are contemplated to be within the scope of this invention including mixtures of the stereoisomeric forms.

The following three schemes of preparation are generally exemplary of the process which can be employed for the preparation of the present complex.

Scheme I

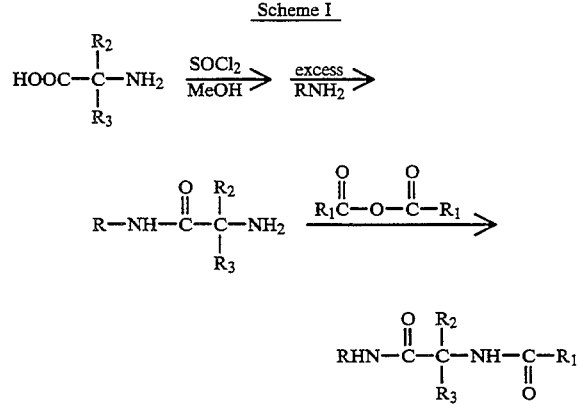

Scheme II

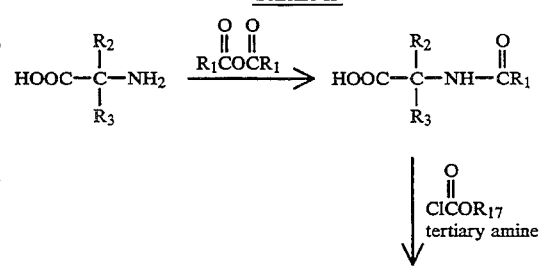

Scheme II (continued)

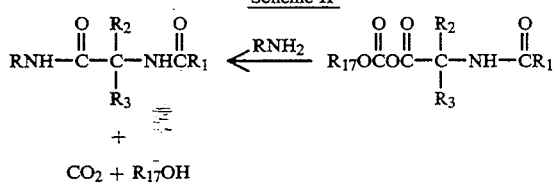
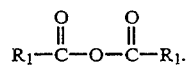

$CO_2 + R_{17}OH$

Scheme III

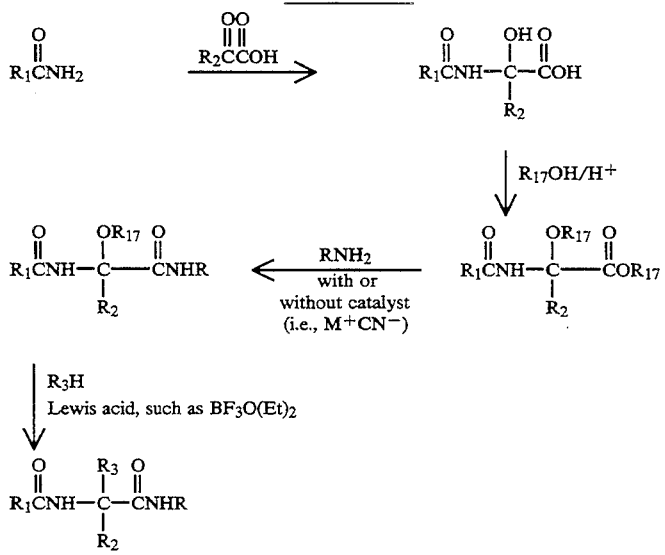

wherein $R_3$=aryl, heteroaromatic and $R_7$ is as defined hereinabove.

More specifically, these compounds can be prepared by art-recognized procedures from known compounds or readily preparable intermediates. For instance, compounds of Formula I can be prepared by reacting amines of Formula II with an acylating derivative of a carboxylic acid of Formula III under amide forming conditions:

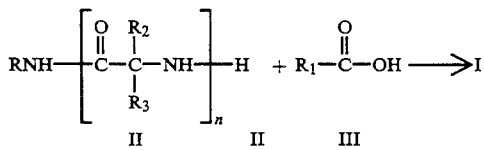

wherein R, $R_1$, $R_2$, $R_3$ and are as defined hereinabove and n=1.

The amide forming conditions referred to herein involve the use of known derivatives of the described acids, such as the acyl halides, (e.g.

$R_1-\underset{\underset{O}{\|}}{C}-X$, wherein X is Cl, Br and the like), anhydrides (e.g.,

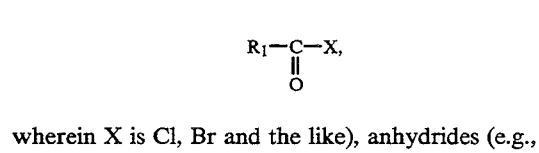

mixed anhydrides, or lower alkyl esters, and the like. It is preferred that the acylating derivative used is the anhydride, $$R_1-\underset{\underset{}{\|}}{\overset{O}{C}}-O-\underset{\underset{}{\|}}{\overset{O}{C}}-R_1.$$

When alkyl esters are employed, amide bond formation can be catalyzed by metal cyanides such as sodium or potassium cyanides.

Another exemplary procedure for preparing compounds wherein at least one of $R_2$ and $R_3$ is aromatic or heteroaromatic is depicted in Scheme IV.

The ester (IV) is reacted with halogen and ultraviolet light in the presence of a catalyst, e.g., AIBN, to form the halo derivative (V). (V) is reacted in the presence of a Lewis acid, such as zinc chloride, with an aromatic or heteroaromatic compound to form the compound (VI). (VI) in turn is hydrolyzed and then reacted with alkyl-haloformate, such as alkylchloroformate in the presence of a tertiary amine to generate the mixed N-acyl amino acid carbonic ester anhydride (VIII). This intermediate is reacted with an amine under amide forming conditions to give the compound of Formula I. Alternatively, (VI) can be reacted directly with an amine ($RNH_2$) optionally in the presence of a metal catalyst, such as metal cyanides, e.g., potassium or sodium cyanide, under amide forming conditions to form a compound of Formula I. Alternatively, compound VIII can be prepared by an independent method and converted to VI which is then reacted with an amine, with or without catalyst to form the compound of Formula I.

Scheme IV

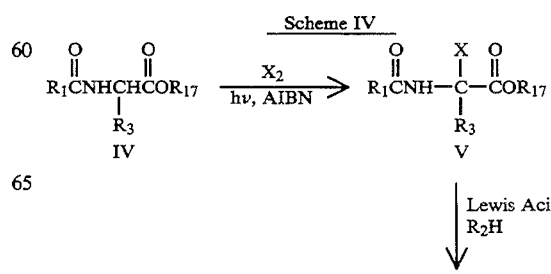

-continued
Scheme IV

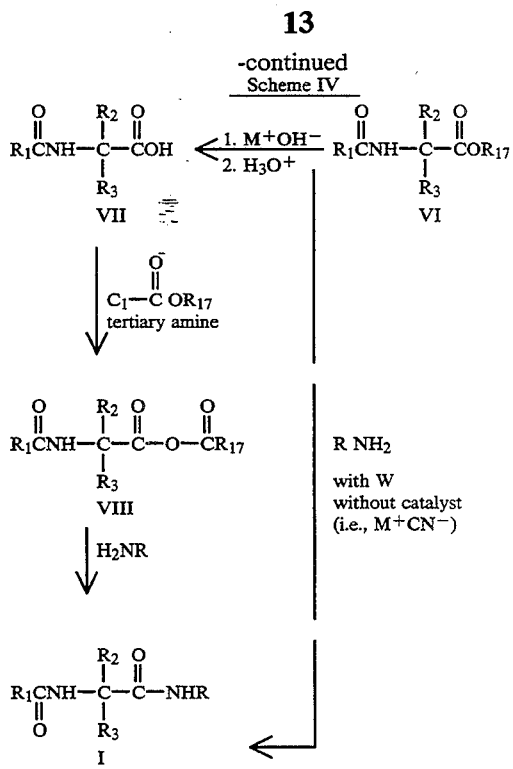

X = halogen (i.e., C¹, Br)
R$_{16}$ = lower alkyl, aryl, arly lower alkyl
M+ = metal cation (i.e., Na+, K+)

Two additional synthetic routes may be employed for the preparation of compounds wherein R$_2$ or R$_3$ is Z-Y as defined hereinabove. In one scheme, for the preparation of these complexes, a substitution reaction is used:

Scheme V

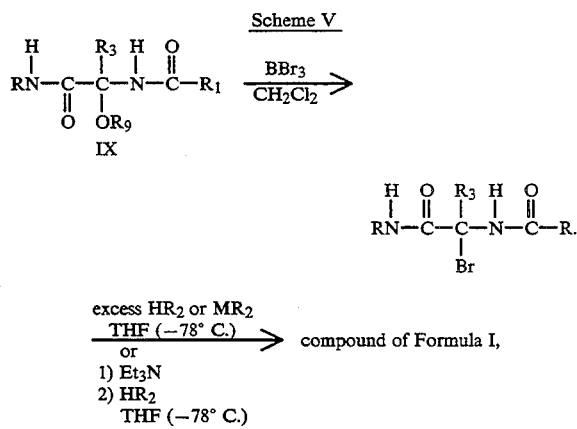

In the above scheme, R$_9$ is lower alkyl, R$_2$ is Z-Y and Z, Y, R, R$_3$ and R$_1$ are as defined hereinabove.

The ether functionality on IX can be cleaved by treatment with Lewis acids, such as BBr$_3$ in an inert solvent such as methylene chloride to form the corresponding halo (bromo) derivative. Addition of either an excess of the H-R$_2$ or MR$_2$ or the sequential addition of triethylamine and H-R$_2$ to a THF mixture containing the halo derivative furnishes the desired product. For example, in the case wherein the compound of Formula IX is 2-acetamido-N-benzyl-2-ethoxy acetamide, its treatment with BBr$_3$ in CH$_2$Cl$_2$ led to the formation of the α-bromo derivative, 2-acetamido-N-benzyl-2-bromoacetamide. Addition of an excess of HR$_2$ or the sequential addition of triethylamine and HR$_2$ to a THF mixture containing the bromo adduct furnishes the desired product.

In another procedure, the product wherein R$_2$ or R$_3$ is Z-Y can also be prepared by substitution reaction on a quaternary ammonium derivative of the compound of Formula I as outlined below Scheme VI

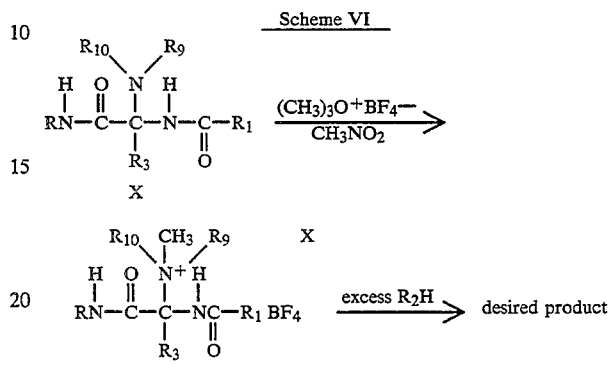

In scheme VI, R, R$_1$, R$_3$ and R are as defined hereinabove, R$_2$ is Z-Y and R$_9$ and R$_{10}$ are independently lower alkyl. In scheme VI, methylation of compound X with a methylation reagent, such as trimethyloxonium tetrafluoroborate provided the corresponding ammonium derivative. Subsequent treatment of the ammonium salt with HR$_2$ furnishes the desired product. For example, methylation of 2-acetamido-N-benzyl-2-(N,N-dimethylamino) acetamide with trimethyloxonium tetrafluoroborate in nitromethane furnished the quaternary ammonium derivative, 2-acetamido-N-benzyl-(N,N,N-trimethylammonium) acetamide tetrafluoroborate in high yields. Subsequent treatment of the salt with the HR$_2$ reagent in the methanol leads to the production of the desired product.

As in any organic reaction, solvents can be employed such as methanol, ethanol, propanol, acetone, tetrahydrofuran, dioxane, dimethylformamide, dichloromethane, chloroform, and the like. The reaction is normally effected at or near room temperature, although temperatures from 0° C. up to the reflux temperature of the reaction mixture can be employed.

As a further convenience, the amide forming reaction can be effected in the presence of a base, such as tertiary organic amine, e.g., triethylamine, pyridine, 4-methylmorpholine, picolines and the like, particularly where hydrogen halide is formed by the amide forming reaction, e.g., the reaction acyl halide and the amine of Formula II. Of course, in those reactions where hydrogen halide is produced, any of the commonly used hydrogen halide acceptors can also be used.

The exact mineral acid or Lewis acid employed in the reaction will vary depending on the given transformation, the temperature required for the conversion and the sensitivity of the reagent toward the acid in the reaction employed.

The various substituents on the present new compounds, e.g., as defined in R, R$_1$, R$_2$ and R$_3$ can be present in the starting compounds, added to any one of the intermediates or added after formation of the final products by the known methods of substitution or conversion reactions. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can be then transformed to the corresponding alkyl groups by various methods, including the Woff-Kishner reduction and Clemmenson reduction. Amino groups can be alkylated to form mono, dialkylamino and trialkylamino groups; and mercapto and hydroxy groups can be alkylated to form corresponding thioethers or ethers, respectively. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

In the above reactions, if the substituents themselves are reactive, then the substituents can themselves be protected according to the techniques known in the art. A variety of protecting groups known in the art may be employed. Examples of many of these possible groups may be found in "Protective Groups in Organic Synthesis," by T. W. Greene, John Wiley & Sons, 1981.

Resulting mixtures of isomers can be separated in the pure isomers by methods known to one skilled in the art, e.g., by fractional distillation, crystallization and/or chromotagraphy.

The present compounds obviously exist in stereoisomeric forms and the products obtained thus can be mixtures of the isomers, which can be resolved. Optically pure functionalized amino acid derivatives can be prepared directly from the corresponding pure chiral intermediate. Racemic products can likewise be resolved into the optical antipodes, for example, by separation of diastereomeric salts thereof, e.g., by fractional crystallization, by selective enzymatic hydrolysis, e.g., papain digestion, or by use of a chiral stationary phase in chromotagraphy (HPLC). For a discussion of chiral stationary phases for HPLC, See, DeCamp, Chirality, 1, 2-6 (1989), which is incorporated herein by reference with the same force and effect as if fully set forth herein.

For example, a racemic mixture of any of the intermediate in any of the schemes, e.g.,

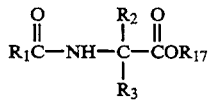

wherein $R_{17}$ is H (which can be prepared according to the procedures of Schemes 1, 2, 3 or 4) is reacted with an optically active amine, $RNH_2$, e.g., (R)(+)α-methylbenzylamine to form a pair of diasteroomeric salts. Diastereomers can then be separated by recognized techniques known in the art, such as fractional recrystallization and the like.

In another method, a racemic mixture of final products or intermediates can be resolved by using enzymatic methods. Since enzymes are chiral molecules, it can be used to separate the racemic modification, since it will preferentially act on one of the compounds, without affecting the enantiomer. For example, acylase, such as acylase I, can be used to separate the racemic modification of an intermediate D,L(±)α-acetamido-2-furanacetic acid. It acts on the L (±)α-acetamido-2-furanacetic acid, but will not act on the D enantiomer. In this way, the D(−)α-acetamido-2-furanacetic acid can be isolated. The intermediate can then react with the amine ($RNH_2$) under amide forming conditions as described hereinabove to form the compound of Formula I.

The active ingredients of the therapeutic compositions and the compounds of the present invention exhibit excellent anticonvulsant activity when administered in amounts ranging from about 10 mg to about 100 mg per kilogram of body weight per day. A preferred dosage regimen for optimum results would be from about 20 mg to about 50 mg per kilogram of body weight per day, and such dosage units are employed that a total of from about 1.0 gram to about 3.0 grams of the active compound for a subject of about 70 kg of body weight are administered in a 24-hour period. This dosage regimen may be adjusted to provide the optimum therapeutic response and is preferably administered one to three times a day in dosages of about 600 mg per administration. For example, several divided doses may be administered daily or the dose may be proportionally reduced as indicated by the exigencies; of the therapeutic situation. A decided practical advantage is that the active compound may be administered in an convenient manner such as by the oral, intraveneous (where water soluble), intramuscular or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may convientyly be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 5 and 1000 mg of active compound.

The tablets, troches, pills, capsules and the like may also contain the following: A binder such as gum tragacanth, acacia, corn starch or gelatin; excipients such as dicalcium phosphate; a disintergrating agent such as corn starch, potato starch, alginic acid and the liek; a lubrican such as magnesium stearate; and a sweetening agent such as sucrose, lactose or saccharin mauy be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the acitve compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly, dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 250 to about 750 mg being preferred. Expressed in proportions, the active compound is generally present in from about 10 to about 750 mg/ml of carrier. In the case of compositions containing supplementary active ingredients, the dosages are determined by reference to the usual dose and manner of administration of the said ingredients.

The compounds of the present invention may be administered in combination with other anti-convulsant agents, such as phenytoin, phenbarbitol, mephenytoin, and phenacemide, and the like. This combination is likely to exhibit synergistic effects.

For a better understanding of the present invention together with other and further objects, reference is made to the following description and examples.

General Methods. Melting points were determined with a Thomas-Hoover melting point apparatus and are uncorrected. Infrared spectra (IR) were run on a Beckman IR-4250 and Perkin-Elmer 1330 and 283 spectrophotometers and calibrated against the 1601-cm$^{-1}$ band of polysytrene. Absorption values are expressed in wavenumbers (cm$^{-1}$). Proton nuclear magnetic resonance ($^1$H NMR) spectra were recorded on Varian Associates Models T-60 and FT-80A, General Electric QE 300, and Nicolet NT-300 NMR spectrometers. Carbon nuclear magnetic resonance ($^{13}$C NMR) spectra were run on a Varian Associates Models FT-80A General Electric QE 300 and Nicolet NT-300 instrument. Chemical shifts are in parts per million ($\delta$ values) relative to Me$_4$Si, and coupling constants (J values) are in hertz. Mass spectral data were obtained at an ionizing voltage of 70 eV on a Hewlett-Packard 5930 gas chromotagraph-mass spectrometer and a Bell-Howell 21-491 spectrometer as well as at the Eli Lilly Laboratories on a Varian MAT-CH-5 spectrometer. High-resolution (EI mode) mass spectra were performed by Drs. James Hudson and John Chinn at the Department of Chemistry, University of Texas at Austin, on a CEC21-110B double-focusing magnetic-sector spectrometer at 70 eV. Elemental analyses were obtained at Spang Microanalytical Laboratories, Eagle Harbor, Mich. and at the Eli Lilly Research Laboratories.

The solvents and reactants were of the best commercial grade available and were used without further purification unless noted. All anhydrous reactions were run under nitrogen, and all glassware was dried before use. In particular, acetonitrile and triethylamine were distilled from CaH$_2$, while dichloromethane was distilled from P$_2$O$_5$. Acetic anhydride, benzaldehyde and ethyl chloroformate were fractionally distilled.

Preparation of N-Acetyl-D- and L-amino acid-N-benzylamides

General Procedure. The D- or L-amino acid amide (11 mmol) was dissolved in dichloromethane (15 mL) and then acetic anhydride (1.23 g, 1.40 mL, 12 mmol) was added dropwise. The solution was stirred at room temperature (18 h) and then concentrated to dryness. The residue was recrystallized from chloroform/hexane. The following examples 1–7 were prepared according to this procedure.

EXAMPLE 1

Preparation of N-Acetyl-D,L-alanine-N'-benzylamide

Acetic anhydride (2.20 g, 0.022 mol) was slowly added to a methylene chloride solution (30 mL) of D,L-alanine-N-benzylamide (3.80 g, 0.021 mol) and allowed to stir at room temperature (3 h). The mixture was then successively washed with $H_2O$ (15 mL), 1% aqueous NaOH (15 mL) and $H_2O$ (15 mL), dried ($Na_2SO_4$) and concentrated in vacuo. The residue was recrystallized from $CH_2Cl_2$.

Yield: 2.50 g (54%). mp 139°–141° C.

$^1$H NMR (DMSO-$d_6$): δ1.22 (d,J=7.1 Hz, 3H), 1.84 (s, 3H), 4.04–4.50 (m, 3H), 7.26 (s, 5H), 8.11 (br d,J=7.3 Hz, 1H), 8.42 (br t,J=6 Hz, 1H).

$^{13}$C NMR (DMSO-$d_6$): 18.2, 22.4, 41.9, 48.2, 126.5, 126.9, 128.1, 139.4, 168.9, 172.4 ppm.

IR (CHCl$_3$) 3440, 3300, 3005, 1660, 1515 cm$^{-1}$.

Mass spectrum (CI mode), m/e: 221 (P+I); mol wt 220.1208

(Calculated for $C_{12}H_{16}N_2O_2$, 220.1212).

EXAMPLE 2

N-Acetyl-D-alanine-N'-benzylamide

Yield: 1.36 g (56%). mp 139°–141° C. $[α]_D^{23}$=+36.2 (c 2.5, MeOH).

$^1$H NMR (80 MHz, DMSO-$d_6$): δ1.25 (d,J=7.1 Hz, 3H), 1.86 (s, 3H), 4.10–4.50 (m, 1H), 4.30 (d,J=6.0 Hz, 2H), 7.26 (s, 5H), 8.09 (d,J=7.3 Hz, 1H), 8.40 (t,J=6.0 Hz, 1H ).

$^{13}$C NMR (80 MHz, DMSO-$d_6$): 18.3, 22.5, 42.0, 48.4, 126.6, 127.0 (2C), 128.2 (2C), 139.4, 169.2, 172.5 ppm.

IR (KBr): 3290, 1635 (br), 1540, 1455, 700, 695 cm$^{-1}$.

Mass spectrum, m/e (relative intensity): 221 (30), 114 (20), 106 (40), 91 (80), 87 (100), 77 (5), 72 (20), 65 (5).

Elemental analysis Calculated for $C_{12}H_{16}N_2O_2$ 65.42% C; 7.34% H; 12.72% N. Found 65.31% C; 7.28% H; 12.63% N.

EXAMPLE 3

N-Acetyl -L-alanine-N'-benzylamide

Yield: 1.11 g (46%). mp 139°–142° C. $[α]_D^{23}$=−35.3 (c 2.5, MeOH).

$^1$H NMR (80 MHz, DMSO-$d_6$): δ1.23 (d,J=7.2 Hz, 3H), 1.86 (s, 3H), 4.26–4.35 (m, 1H), 4.29 (d,J=5.8 Hz, 2H), 7.22–7.33 (s, 5H), 8.10 (d,J=7.4 Hz, 1H), 8.42 (t,J=5.8 Hz, 1H).

$^{13}$C NMR (80 MHz, DMSO-$d_6$): 18.3, 22.6, 42.0, 48.4, 126.7, 127.0 (2C) 128.3 (2C) 139.5, 169.2, 172.6 ppm.

IR (KBr): 3290, 1635 (br), 1545, 1450, 700, 695 cm$^{-1}$.

Mass spectrum, m/e (relative intensity): 221 (40), 114 (40), 106 (80), 106 (80), 91 (75), 87 (100), 77 (5), 72 (15), 65 (5).

Elemental analysis Calculated for $C_{12}H_{16}N_2O_2$ 65.42% C; 7.34% H; 12.72% N. Found 65.58% C; 7.32% H; 12.43% N.

EXAMPLE 4

Preparation of N-Acetyl-D,L-phenylglycine-N'-methylamide

Acetic anhydride (2.90 g, 28 mmol) was added dropwise to D,L-phenylglycine-N-methylamide (3.4 g, 20 mmol) and allowed to stir at room temperature (1.5 h). During this time, a copious white precipitate formed. This material was collected by filtration, dried in vacuo and recrystallized from absolute alcohol.

Yield: 2.00 g (49%). mp 232°–235° C. (dec).

$^1$H NMR (DMSO-$d_6$): δ1.89 (s, 3H), 2.58 (d,J=4.6 Hz, 3H), 5.42 (d,J=8.1 Hz, 1H), 7.35 (s, 5H), 8.18 (br q,J=4.2 Hz, 1H), 8.47 (d,J=8.1 Hz, 1H).

$^{13}$C NMR (DMSO-$d_6$): 22.4, 25.5, 56.3, 127.1, 127.3, 128.1, 139.0, 168.9, 170.3 ppm.

IR (KBr): 3310, 1645 cm$^{-1}$.

Mass spectrum (CI mode), m/e: 207 (P+I).

Elemental analysis Calculated for $C_{11}H_{14}N_2O_2$ 64.06% C; 6.86% H; 13.58% N. Found 63.79% C; 6.66% H; 13.27% N.

EXAMPLE 5

Preparation of N-Acetylglycine-N-benzylamide

The D,L-amino acid amide (11 mmol) was dissolved in dichloromethane (15mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 1.84 g (81%). mp 140°–142° C.

$^1$NMR (DMSO-$d_6$): δ1.88 (s, 3H), 3.74 (d,J=5.3 Hz, 2H), 4.30 (d,J=5.1 Hz, 2H), 7.27 (s, 5H), 8.37 (br s, 1H), 8.75 (br s, 1H).

$^{13}$C NMR (DMSO-$d_6$): 22.5, 42.0, 42.5, 126.6, 127.1 (2C), 128.1 (2C), 139.3, 169.0, 169.6 ppm.

IR (KBr): 3060, 1655, 1640, 1560, 1545, 1450, 1300, 740, 710 cm$^{-1}$.

Mass spectrum, m/e (relative intensity): 206 (3), 147 (12), 106 (100), 91 (75), 73 (50).

Elemental analysis Calculated for $C_{11}H_4N_2O_2$ 64.05% C; 6.86% H; 13.58% N. Found 64.03% C; 6.79% H; 13.61% N.

EXAMPLE 6

Preparation of N-Acetyl-D,L-valine-N-benzylamide

The D,L-amino acid amide (11 mmol) was dissolved in dichloromethane (15 mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 2.35 g (86%). mp 192°–193° C.

$^1$H NMR (DMSO-$d_6$): δ0.83 (d,J=6.7 Hz, 6H), 1.87 (s, 3H), 1.73–2.09 (m, 1H), 4.11 (d,J=8.8 Hz, 1H), 4.27 (d,J=5.8 Hz, 2H), 7.26 (s, 5H), 7.89 (d,J=8.8 Hz, 1H), 8.84 (t,J=5.8 Hz, 1H).

$^{13}$C NMR (DMSO-$d_6$): 18.1, 19.2, 22.4, 30.2, 41.9, 57.8, 126.6, 127.1 (2C), 128.1 (2C), 139.4, 169.2, 171.1 ppm.

IR (KBr): 1625, 1540, 1535, 1450 1380 1290 750 695 cm$^{-1}$.

Mass spectrum, m/e (relative intensity): 142 (16), 114 (43), 106 (29), 91 (57), 72 (100).

Elemental analysis Calculated for $C_{14}H_{20}N_2O_2$ 67.70% C; 8.13% H; 11.28% N. Found 67.58% C; 8.05% H; 11.10% N.

EXAMPLE 7

Preparation of N-Acetyl-D,L-phenylglycine-N-benzylamide

The D,L-amino acid amide (11 mmol) was dissolved in dichloromethane (15mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 2.05 g (66%). mp 202°–203° C.

$^1$H NMR (DMSO-d$_6$): δ1.91 (s, 3H), 4.27 (d,J=5.6 Hz, 2H), 5.50 (d,J=7.9 Hz, 1H), 7.21 (s, 5H), 7.36 (s, 5H), 8.38–8.86 (m, 2H).

$^{13}$C NMR (DMSO-d$_6$): 22.3, 42.0, 56.3, 126.6 (2C), 127.0, 127.1 (2C), 127.4 (2C), 128.1 (2C), 138.9, 139.0, 168.9, 169.9 ppm.

IR (KBr): 3020, 1635, 1580, 1540, 1450, 1265, 745, 690 cm$^{-1}$.

Mass spectrum, m/e (relative intensity): 283 (20), 264 (21), 149 (100), 131 (20), 118 (34), 106 (92), 91 (70), 79 (56), 77 (54), 65 (45), 51 (37).

Elemental analysis Calculated for $C_{17}H_{18}N_2O_2$ 72.31% C; 6.44% H; 9.92% N. Found 72.49% C; 6.47% H; 9.89% N.

Preparation of N-Acetyl-D- and L-phenylglycine-N-benzylamide

General Procedure. The chiral Boc-protected phenylglycine-N-benzylamide was dissolved in trifluoroacetic acid (0.04M) and was stirred at room temperature (30 min), during which time gas evolved. The solution was concentrated in vacuo and the residue was redissolved in enough methanol to form a solution of 0.2M. Methanesulfonic acid (1 equiv) was added dropwise and stirred for 5 min. After concentrating the solution in vacuo, the residue was repeatedly dissolved in methanol and the solvent was removed (3 times). The residue was then dried under vacuum (18 h), leaving a yellow oil.

Without further purification, the phenylglycine-N-benzylamide methanesulfonate was dissolved in tetrahydrofuran (0.2M) and then was cooled in an ice bath. Triethylamine (2 equiv) was added dropwise, followed by acetyl chloride (1 equiv). The ice bath was removed and stirring was continued at room temperature (18 h). The solution was concentrated in vacuo and the residue was recrystallized from 1:1 95% ethanol/water. Examples 8 and 9 were prepared according to this procedure.

EXAMPLE 8

N-Acetyl-D-phenylgylcine-N-benzylamide

The reaction was run on an 11.9 mmol scale.

Yield: 2.97 g (88%). mp 219°–221° C. $[α]_D=-103.0$ (c 1%, EtOH).

$^1$H NMR (DMSO-d$_6$): δ1.91 (s, 3H), 4.27 (d,J=5.5 Hz, 2H), 5.50 (d,J=7.8 Hz, 1H), 7.14–7.44 (m, 10H), 8.56 (d,J=7.8 Hz, 1I), 8.79 (t,J=5.5 Hz, 1H).

$^{13}$C NMR (DMSO-d$_6$): 22.4, 42.0, 56.4, 126.7, 127.0 (2C), 127.2 (2C), 127.4, 127.9 (2C), 128.1 (2C), 138.9, 139.0, 168.9, 170.0 ppm.

IR (KBr): 3260, 1620, 1525, 1450, 1370, 720, 690 cm$^{-1}$.

Mass spectrum, m/e (relative intensity): 203 (2), 149 (94), 106 (100), 91 (32), 86 (43), 77 (14).

Elemental analysis Calculated for $C_{17}H_{18}N_2O_2$ 72.32% C; 6.43% H; 9.92% N. Found 72.04% C; 6.22% H; 9.78% N.

EXAMPLE 9

N-Acetyl-L-phenylglycine-N-benzylamide

Beginning with 16.1 mmol N-t-Boc-L-phenylglycine-N-benzylamide.

Yield: 2.99 g (66%). mp 221°–222° C. $[α]_D=+105.1$ (c 1%, EtOH).

$^1$H NMR (DMSO-d$_6$): δ1.99 (s, 3H), 4.36 (d,J=5.6 Hz, 2H), 5.60 (d,J=8.0 Hz, 1H), 7.23–7.53 (m, 10H), 8.60 (d,J=8.0 Hz, 1H), 8.83 (t,J=5.6 Hz, 1H).

$^{13}$C NMR (DMSO-d$_6$): 22.4, 42.1, 56.5, 126.8, 127.1 (2C), 127.3 (2C), 127.5, 128.2 (4C), 139.0, 139.1, 169.1, 170.1 ppm.

IR (KBr): 3295, 1630, 1530, 1450, 1395, 720, 695 cm$^{-1}$.

Mass spectrum, m/e (relative intensity): 223 (1), 203 (2), 149 (98), 106 (100), 91 (32), 86 (43), 77 (11).

Elemental analysis Calculated for $C_{17}H_{18}N_2O_2$ 72.32% C; 6.43% H; 9.92% N. Found 72.53% C; 6.49% H; 9.67% N.

EXAMPLE 10

Preparation of N-Acetyl-D,L-alanine-N-(3-methoxy)benzylamide

The D,L-amino acid amide (11 mmol) was dissolved in dichloromethane (15mL) and then acetic anhydride (1.23 g, 1.40 mL, 12 mmol) was added dropwise. The solution was stirred at room temperature (4–6 h) and then concentrated to dryness. The residue was recrystallized from chloroform/hexane.

Yield: 0.47 g (17%). mp 112°–115° C.

$^1$H NMR (DMSO-d$_6$): δ1.23 (d,J=7.1 Hz, 3H), 1.85 (s, 3H), 3.73 (s, 3H), 3.99–4.48 (m, 1H), 4.25 (d,J=6.1 Hz, 2H), 6.58–7.35 (m, 4H), 8.05 (d,J=7.4 Hz, 1H), 8.35 (t,J=6.0 Hz, 1H).

$^{13}$C NMR (DMSO-d$_6$): 18.1, 22.5, 41.8, 48.3, 54.9, 112.2, 112.3, 119.0, 129.2, 141.0, 159.3, 169.0, 172.4 ppm.

IR (KBr): 3270, 3065, 1625, 1580, 1450, 1260, 1150, 1095, 900, 775, 700, 690 cm$^{-1}$.

Elemental analysis Calculated for $C_{13}H_{18}N_2O_3$ 62.37% C; 7.26% H; 11.19% N. Found 62.29% C; 7.13% H; 11.08% N.

EXAMPLE 11

Preparation of N-Trimethylacetyl-D,L-alanine-N-benzylamide

D,L-Alanine-N-benzylamide (3.56 g, 20 mmol) was dissolved in dichloromethane (25 mL) and trimethylacetic anhydride (4.10 g, 4.46 mL, 22 mmol) was added dropwise. The solution was stirred at room temperature (18 h) and then concentrated to dryness. The solid residue was recrystallized from benzene/petroleum ether (30°–60° C.).

Yield: 2.07 g (40%). mp 123°–124° C.

$^1$H NMR (DMSO-d$_6$): δ1.12 (s, 9H), 1.27 (d,J=7.1 Hz, 3H), 4.23–4.42 (m, 1H), 4.31 (d,J=5.4 Hz, 2H), 7.23–7.30 (m, 5H), 7.38 (d,J=7.4 Hz, 1H), 8.26 (t,J=5.4 Hz, 1H).

$^{13}$C NMR (DMSO-d$_6$): 18.1, 27.2 (3C), 37.9, 42.0, 48.4, 126.6, 127.0 (2C), 128.2 (2C), 139.4, 172.5, 177.1 ppm.

IR (KBr): 3300, 1630, 1535 (br), 1455, 745, 695 cm$^{-1}$.

Mass spectrum, m/e (relative intensity): 262 (2), 203 (19), 156 (18), 128 (51), 106 (31), 91 (100), 77 (15), 65 (28).

Elemental analysis Calculated for $C_{15}H_{22}N_2O_2$ 68.66% C; 8.47% H; 10.68% N. Found 68.91% C; 8.14% H; 10.67% N.

EXAMPLE 12

Preparation of N-Acetyl-D, L-methionine-N-benzylamide

N-Acetyl-D,L-methionine (4.78 g, 25 mmol) was combined with acetonitrile (75 mL) and the mixture was placed into an ice/salt water bath (−5° C.). Triethylamine (2.53 g, 3.48 mL, 25 mmol) was added dropwise, followed by ethyl chloroformate (2.71 g, 2.39 mL, 25 mmol). All additions were done slowly so that the temperature of the mixture did not rise above 0° C. The mixture was then stirred at −5° C. (20 min). Benzylamine (3.00 g, 3.06 mL, 28 mmol) in acetonitrile (5 mL) was added dropwise and the mixture was stirred at +−5° C. (1 h) and then room temperature (18 h).

The mixture was filtered and a white precipitate was collected and dried in vacuo and identified as the desired product ($^1$H NMR and $^{13}$C NMR analyses). The filtrate was concentrated in vacuo and the residue was combined with hot tetrahydrofuran (50 mL) and cooled in the freezer (3 h), resulting in the formation of a white precipitate. The mixture was filtered and the precipitate was collected, dried in vacuo, and identified as triethylammonium hydrochloride.

The latter filtrate containing tetrahydrofuran was concentrated in vacuo and the resulting residue-was purified by flash column chromatography (ethyl acetate). A white solid ($R_f$=0.50, ethyl acetate) was isolated and was identified as the desired product ($^1$H NMR, and $^{13}$C NMR analyses). The two solids identified as N-acetyl-D,L-methionine-N-benzylamide were combined and recrystallized from benzene/petroleum ether (30°–60° C.).

Yield: 2.98 g (43%). mp 134°–135° C.

$^1$H NMR (DMSO-d$_6$): δ1.69–1.94 (m, 2H), 1.87 (s, 3H), 2.02 (s, 3H), 2..29–2.59 (m, 2H), 4.10–4.53 (m, 1H), 4.29 (d,J=6.0 Hz, 2H), 7.26 (s, 5H), 8.12 (d,J=8.5 Hz, 1H), 8.47 (t,J=6.0 Hz, 1H).

$^{13}$C NMR (DMSO-d$_6$): 14.6, 22.5, 29.7, 31.8, 42.0, 52.0, 126.6, 127.0 (2C), 128.2 (2C), 139.4, 169.5, 171.4 ppm.

IR (KBr): 3280, 1630, 1545, 1460, 750, 700 cm$^{-1}$.

Mass spectrum, m/e (relative intensity): 280 (3), 206 (100), 164 (29), 146 (20), 106 (54), 91 (76), 77 (14), 65 (24).

Elemental analysis Calculated for $C_{14}H_{20}N_2O_2S$ 59.96% C; 7.20% H; 9.99% N. Found 60.02% C; 7.14% H; 9.91% N.

EXAMPLE 13

Preparation of N-Acetylalanine-N'-(3-fluoro)benzylamide

N-Acetylalanine (3.28 g, 25 mol) was combined with acetonitrile (100 mL) and the mixture was placed into an ice/salt bath at −5° C. Triethylamine (2.53 g, 3.5 mL, 25 mmol) was added dropwise followed by the addition of ethyl chloroformate (2.71 g, 2.40 mL, 25 mmol). All additions were done slowly so that the temperature of the mixture did not rise above 0° C. The mixture was then stirred at −5° C. for 20 minutes. 3-Fluorobenzylamine (3.58 g, 28 mmol) and acetonitrile (5 mL) was added dropwise and was stirred at −5° C. for one hour and then at room temperature for 18 hours. The reaction became homogenous during this time interval.

The solution was concentrated in vacuo and the residue was combined with hot tetrahydrofuran (100 mL) and cooled in the freezer for 3 hours resulting in the formation of a white precipitate. The mixture was filtered and the precipitate was collected, dried in vacuo and identified as triethylammonium hydrochloride (3.51 g, mp 253°–257° C.). The filtrate was concentrated in vacuo and the resulting yellow solid was recrystallized from chloroform/diethyl ether.

Yield: 3.22 g (54%). mp 120°–121° C.

$^1$H NMR (DMSO-d$_6$): δ1.27 (d,J=7.1 Hz, 3H), 1.90 (s, 3H), 4.23–4.41 (m, 1H), 4.33 (d,J=6.1 Hz, 2H), 7.05–7.37 (m, 4H), 8.19 (d,J=7.1 Hz, 1H), 8.53 (t,J=6.1 Hz, 1H).

$^{13}$C NMR (DMSO-d$_6$): 17.9, 22.4, 41:5, 48.5, 113.3 (d,J=20.4 Hz), 113.5 (d,J=21.7 Hz), 122.8, 130.1 (d,J=7.9 Hz), 142.4 (d,J=7.4 Hz), 162.3 (d,J=243.6 Hz), 169.6, 172.8 ppm.

IR (KBr): 3280, 1645, 1545, 1450, 745, 680 cm$^{-1}$.

Mass spectrum, m/e (relative intensity): 238 (18), 151 (22), 124 (49), 114 (47), 109 (100), 87 (76), 72 (27).

Elemental analysis Calculated 60.48% C; 6.36% H; 11.76% N. Found 60.55% C; 6.32% H; 11.71% N.

EXAMPLE 14

Preparation of D,L-α-Acetamido-N-benzyl-3-thiopheneacetamide

D,L-α-Acetamido-3-thiopheneacetic acid (2.99 g, 15 mmol) was combined with acetonitrile (60 mL) and the mixture was placed into an ice/salt water bath (−5° C.). Triethylamine (1.51 g, 2.10 mL, 15 mmol) was added dropwise, followed by ethyl chloroformate (1.63 g, 1.43 mL, 15 mmol). All additions were done slowly so that the temperature of the mixture did not rise above 0° C. The mixture was then stirred at −5° C. (20 min). Benzylamine (1.77 g, 1.80 mL, 16.5 mmol) in acetonitrile (10 mL), was added dropwise and the mixture was stirred at −5° C. (1 h) and then room temperature (18 h). The mixture was concentrated in vacuo and the residue was combined with hot tetrahydrofuran (50 mL) and cooled in the freezer (3 h), resulting in the formation of a white precipitate. The mixture was filtered and the precipitate was collected, dried in vacuo, and identified as triethylammonium hydrochloride ($^1$H NMR analysis). The filtrate was concentrated in vacuo and the resulting yellow solid was recrystallized from 1:1 95% ethanol/water.

Yield: 1.91 g (44%). mp 198°–199° C.

$^1$H NMR (DMSO-d$_6$): δ1.91 (s, 3]I), 4.29 (d,J=5.2 Hz, 2H), 5.61 (d,J=7.9 Hz, 1H), 7.15–7.50 (m, 3H), 8.55 (d,J=7.9 Hz, 1H), 8.74 (t,J=5.2 Hz, 1H).

$^{13}$C NMR (DMSO-d$_6$): 22.3, 42.0, 52.5, 122.4, 126.1, 126.7, 127.0 (3C), 128.2 (2C), 139.0, 139.2, 169.0, 169.8 ppm.

IR (KBr): 3460, 1675, 1570, 1400, 720, 695 cm$^{-1}$.

Mass spectrum, m/e (relative intensity): 288 (2), 245 (3), 155 (88), 112 (100), 91 (31), 85 (17), 65 (7).

Elemental analysis Calculated for $C_{15}H_{16}N_2O_2S$ 62.48% C; 5.59% H; 9.71% N. Found 62.41% C; 5.47% H; 9.55% N.

EXAMPLE 15

Preparation of
D,L-α-Acetamido-N-benzyl-2-thiopheneacetamide

N-Acetyl-D,L-ethoxyglycine-N-benzylamide (6.26 g, 25 mmol) was combined with dry ether (175 mL) and then boron trifluoride etherate (5.68 g, 5.0 mL, 40 mmol) was added dropwise, resulting in a homogeneous solution. After stirring a short time, a small amount of a yellow oil separated from the solution. Thiophene (8.41 g, 8.0 mL, 100 mmol) was then added dropwise via syringe and the reaction was stirred at room temperature (4 d). The mixture was cooled in an ice bath and cold aqueous saturated NaHCO$_3$ (200 mL) was added and the aqueous layer was extracted with ethyl acetate (2×100 mL). The organic washings and the original ether layer were combined, dried (Na$_2$SO$_4$), and concentrated in vacuo. The residue was purified by flash column chromatography, using 94:6 chloroform/methanol as an eluant (R$_f$=0.7 94: 6 chloroform/methanol), and then recrystallized from benzene.

Yield: 2.67 g (37%). mp 167°–169° C.

$^1$H NMR (DMSO-d$_6$): δ1.91 (s, 3H), 4.31 (d,J=6.0 Hz, 2H), 5.74 (d,J=7.9 Hz, 1H), 6.99–7.44 (m, 8H), 8.64 (d,J=7.9 Hz, 1H), 8.85 (t,J=6.0 Hz, 1H).

$^{13}$C NMR (DMSO-d$_6$): 22.4, 42.3, 52.2, 125.6, 125.8, 126.6, 126.9, 127.3 (2C), 128.3 (2C), 139.0, 141.4, 169.2, 169.3 ppm.

Mass spectrum, m/e (relative intensity): 289 (2), 181 (6), 155 (100), 112 (100), 91 (100), 85 .(34), 74 (24).

Elemental analysis Calculated for C$_{15}$H$_{16}$N$_2$O$_2$S 62.48% C; 5.59% H; 9.71% N. Found 62.64% C; 5.73% H; 9.61% N.

EXAMPLE 16

Preparation of
D,L-α-Acetamido-N-benzyl-2-furanacetamide

N-Acetyl-D,L-2-(2-furyl)glycine (0.47 g, 2.56 mmol) was combined with acetonitrile (10 mL) and cooled to −5° C. (ice/salt water bath). Triethylamine (0.26 g, 0.36 mL, 2.56 mmol) was then rapidly added and the mixture stirred at −5° C. (3 min). Ethyl chloroformate (0.28 g, 0.25 mL, 2.56 mmol) was added dropwise between −4° C. and −3° C., and the resulting suspension was stirred at −4° C. (20 min), and then an acetonitrile solution (2 mL) of benzylamine (0.30 g, 0.31 mL, 2.82 mmol) was carefully added. During the addition of benzylamine the temperature of the solution did not go above 0° C. The mixture was stirred at −5° C. (1 h) and at room temperature (18 h), and then concentrated in vacuo. The residue was then triturated with hot tetrahydrofuran (5 mL), cooled at −16° C. (3 h), and the resulting white precipitate was filtered and identified as triethylamine hydrochloride ($^1$H NMR, 60 MHz, δ1.00 (t,J=7.5 Hz, CH$_3$), 2.82 (q,J=7.5 Hz, CH$_2$), 3.83 (s, NH)). The filtrate was evaporated to dryness in vacuo and the resulting oil purified by flash chromatography (98:2 chloroform/methanol) to give 0.09 g (13%) of the desired product as a white solid: R$_f$0.30 (98:2 chloroform/methanol).

mp 178°–179° C.

$^1$H NMR (300 MHz, DMSO-d$_6$): δ1.90 (s, CH$_3$), 4.31 (d,J=6.0 Hz, CH$_2$), 5.58 (d,J=8.1 Hz, CH), 6.27–6.33 (m, C$_3$·H), 6.40–6.44 (m, C$_4$·H), 7.20–7.36 (m, Ph), 7.60–7.64 (m, C$_5$·H), 8.57 (d,J=8.1 Hz, NH), 8.73 (t,J=6.0 Hz, NH).

$^{13}$C NMR (300 MHz, DMSO-d$_6$): 22.35 (CH$_3$), 42.27 (CH$_2$), 50.95 (CH), 107.60 (C$_3$·), 110.55 (C$_4$·), 126.82 (2C$_2$·· or 2C$_3$··), 127.08 (2C$_2$·· or 2C$_3$··), 128.27 (C$_4$·), 139.05 (C$_1$·), 142.58 (C$_5$·),
151.16 (C$_2$·), 168.02 (CH$_3$CO), 169.30 (NHCO) ppm.

IR (KBr): 3230, 1625 (br), 1525 (br), 1375 (br), 1230, 1090, 890 cm$^{-}$.

Mass spectrum, m/e (relative intensity): 273 (1), 139 (100), 96 (94), 91 (51), 65 (9).

Elemental analysis Calculated for C$_{15}$H$_{16}$N$_2$O$_3$ 66.16% C; 5.83% H; 10.29% N. Found 65.92% C; 5.83% H; 10.15% N.

EXAMPLE 17

Preparation of
D,L-α-Acetamido-N-benzyl-2-pyrroleacetamide

2-Acetamido-N-benzyl-2-ethoxyacetamide (2.00 g, 8.0 mmol) was suspended in anhydrous ethyl ether (60 mL), and then boron trifluoride etherate (1.82 g, 1.57 mL, 12.8 mmol) was added in one portion and the resulting solution was stirred (15 min). The pyrrole (2.14 g, 2.22 mL, 32 mmol) was then added in one portion and the solution was stirred at room temperature (48 h) during which time a precipitate formed. Hexanes (80 mL) were then added to the suspension, and the mixture was filtered and the brown semi-solid was triturated with 95:5 chloroform/methanol (30 mL) to furnish a green solid. This material was purified by flash chromatography (95:5 chloroform/methanol) to yield 0.94 g (35%) of the desired product as a white solid: R$_f$0.29 (96:4 chloroform/methanol).

mp 174°–175° C.

$^1$H NMR (300 MHz, CD$_3$CN): δ1.93 (s, CH$_3$), 4.35 (d,J=6.0 Hz, CH$_2$), 5.42 (d,J=6.9 Hz, CH), 6.00–6.18 (m, C$_3$·H, C$_4$·H), 6.68–6.72 (m, C$_5$·H), 7.04 (d,J=6.9 Hz, NH), 7.17 (t,J=6.0 Hz, NH), 7.10–7.47 (m, Ph), 9.10–9.80 (br s, NH).

$^{13}$C NMR (300 MHz, CD$_3$CN): 23.02 (CH$_3$), 43.83 (CH$_2$), 52.65 (CH), 107.57 (C$_3$·), 108.85 (C$_4$·), 119.33 (C$_5$·), 127.96 (C$_2$·), 128.01 (2C$_2$·· or 2C$_3$··), 128.09 (2C$_2$·· or 2C$_3$··), 129.49 (C$_4$··), 140.01 (C$_1$··), 170.94 (COCH$_3$), 171.21 (CONH) ppm.

IR (KBr): 3320, 1570 (br), 1470 (br), 1330, 1230, 950, 890, 860, 760, 710, 690, 655 cm$^{-}$.

Mass spectrum, m/e (relative intensity): 171 (12), 228 (2), 213 (1), 180 (2), 164 (9), 137 (93), 108 (20), 95 (100), 91 (38), 82 (35), 68 (15).

High resolution mass spectral analysis Calculated for C$_{15}$H$_{17}$N$_3$O$_2$ 271.-13208. Found 271.13144.

EXAMPLE 18

Preparation of
D,L-2-Acetamido-N-benzyl-2-ethoxyacetamide

An ethanolic solution (420 mL) of ethyl 2-acetamido-2-ethoxyacetate (27.92 g, 147 mmol) and benzylamine (23.70 g, 24 mL, 221 mmol) was stirred at 40°–45° C. for 3 days. The reaction mixture was evaporated in vacuo and the residue recrystallized (1:3.5 tetrahydrofuran/hexanes (650 mL)) to yield 25.80 g (70%) of the desired product as beige crystals: R$_f$0.59 (95:5 chloroform/methanol).

mp 153°–155° C.

$^1$H NMR (300 MHz, CDCl$_3$): δ1.20 (t,J=7.0 Hz, CH$_3$), 2.07 (s, CH$_3$), 3.60–3.76 (m, CH$_2$CH$_3$), 4.40–4.54 (m, CH$_2$NH), 5.60 (d,J=8.7 Hz, CH), 6.63 (d,J=8.7 Hz, NH), 7.00 (br s, NH), 7.26–7.36 (m, Ph).

$^{13}$C NMR (300 MHz, CDCl$_3$): 15.06 (CH$_3$CH$_2$), 23.25 (CH$_3$CO), 43.60 (CH$_2$NH), 64.51 (CH$_2$CH$_3$), 77.43

(CH), 127.69 (2C$_2$'' or 2C$_3$'', C$_4$), 128.79 (2C$_2$'' or 2C$_3$''), 137.57 (C$_1$''), 168.13 (COCH$_3$), 171.29 (CONH) ppm.

IR (KBr): 3260, 1630 (br), 1550 (sh), 1505 (br), 1380, 1360, 1230, 1115, 1060, 1015, 890, 745, 690 cm$^{-1}$.

Mass spectrum, m/e (relative intensity): 251 (4), 163 (9), 116 (98), 106 (34), 91 (98), 74 (100).

Elemental analysis Calculated for C$_{13}$H$_{18}$N$_2$O$_3$ 62.38% C; 7.25% H; 11.19% N. Found 62.49% C; 7.27% H; 11.24% N.

EXAMPLE 19

Preparation of D, L-2-Acetamido-N-benzyl-2-methoxyacetamide

To a methanolic solution (180 mL) of methyl 2-acetamido-2-methoxyacetate (8.73 g, 54 mmol) was rapidly added benzylamine (8.68 g, 8.80 mL, 81 mmol) and then the mixture was stirred at 50° C. (3 days) during which time a beige precipitate appeared. The solvent was removed in vacuo and the resulting precipitate was recrystallized from tetrahydrofuran (2×) to give 7.67 g (32%) of the desired product as beige crystals: R$_f$ 0.35 (95:5 chloroform/methanol).

mp 145°–146° C.

$^1$H NMR (300 MHz, CDCl$_3$): δ2.06 (s, CH$_3$CO), 3.37 (s, CH$_3$O), 4.40–4.35 (m, CH$_2$), 5.52 (d,J=8.7 Hz, CH), 7.12 (d,J=8.7 Hz, NH), 7.20–7.40 (m, Ph, NH).

$^{13}$C NMR (300 MHz, CDCl$_3$): 23.03 (CH$_3$CO), 43.51 (CH$_2$), 55.84 (CH$_3$O), 78.94 (CH), 127.62 (C$_4$''), 127.70 (2C$_2$'' or 2C$_3$''), 128.70 (2C$_2$ or 2C$_3$''), 137.45 (C$_1$''), 166.91 (COCH$_3$), 17 1.57 (CONH) ppm.

IR (KBr): 1260, 1825 (br), 1550, 1505, 1435, 1390, 1370, 1230, 1120, 1050, 935, 890, 690 cm$^{-1}$.

Mass spectrum, m/e (relative intensity): 237 (1), 205 (2), 177 (2), 163 (4), 146 (1), 134 (1), 121 (2), 106 (26), 102 (98), 91 (95), 77 (13), 61 (100).

Elemental analysis Calculated for C$_{12}$H$_{16}$N$_2$O$_3$ 61.00% C; 6.83% H; 11.86% N. 60.91% C; 6.85% H; 11.66% N.

EXAMPLE 20

Preparation of (D,L)-α-Acetamido-N-benzyl-2-(5-methylfuran)acetamide

N-Acetyl-D,L-ethoxyglycine-N-benzylamide (2.00 g, 8.0 mmol) was suspended in anhydrous ethyl ether, and then boron trifluoride etherate (1.82 g, 12.8 mmol) was rapidly added, and the resulting solution was stirred for 15 min. The 2-methylfuran (2.63 g, 32.0 mmol) was then added and the reaction was stirred at room temperature (3 d). The reaction mixture was poured into an aqueous saturated NaHCO$_3$ solution and extracted with ethyl acetate (3×). The ethyl acetate extracts were combined, dried (Na$_2$SO$_4$) and evaporated in vacuo to give a beige solid, which was purified by flash chromatography (98:2 chloroform/methanol) to give the desired product as a white crystalline solid.

Yield: 1.40 g (61%) R$_f$ 0.25 (98:2 chloroform/methanol). mp 148°–150° C.

$^1$H NMR (DMSO-d$_6$) δ1.88 (s, CH$_3$CO), 2.23 (s, CH$_3$), 4.24–4.36 (m, CH$_2$), 5.49 (d,J=8.0 Hz, CH), 6.01 (br s, C$_3$'H), 6.14 (d, J=2.4 Hz, C$_4$'H), 7.20–7.31 (m, Ph), 8.52 (d, J=8.0 Hz, NH), 8.69 (t,J=5.6 Hz, NH).

$^{13}$C NMR (DMSO-d$_6$) 13.44 (CH$_3$), 22.35 (CH$_3$CO), 44.11 (CH$_2$), 53.23 (CH), 107.51 (C$_3$'' or C$_4$'), 110.40 (C$_3$' or C$_4$'), 128.13 (C$_4$''), 128.18 (2C2'' or 2C$_3$''), 129.43 (2C$_2$'' or 2C$_3$''), 139.69 (C$_1$''), 149.18 (C$_2$'' or C$_5$'), 153.81 (C$_2$' or C$_5$'), 170.78 (CH$_3$CO), 173.03 (CONH) ppm.

IR (KBr) 3270, 1620 (br), 1520 (br), 1440, 1360, 1210, 1010 cm$^-$.

Mass spectrum, m/e (relative intensity) 286 (3), 179(8), 153 (57), 152 (57), 111 (23), 110 (100), 97 (23), 91 (31).

Elemental Analysis Calculated: 67.12% C; 6.34% H; 9.78% N. Found: 66.92% C; 6.52% H; 9.52% N.

EXAMPLE 21

Preparation of (D,L)-α-Acetamido-N-benzyl-2-benzofuranacetamide

N-Acetyl-D,L-ethoxyglycine-N-benzylamide (1.00 g, 4 mmol) was suspended in anhydrous ethyl ether (30 mL) and then boron trifluoride etherate (0.91 g, 6.3 mmol) was rapidly added, and the resulting solution was stirred for 15 min. The benzofuran (1.89 g, 16 mmol) was then added and the reaction was stirred at room temperature (3 d). The reaction mixture was poured into an ice-cold saturated aqueous solution of NaHCO$_3$, and then the mixture was maintained at this temperature for an additional 15 min. The mixture was extracted with ethyl acetate (2×), and the organic layers were combined, dried (Na$_2$SO$_4$) and evaporated in vacuo. The residue was purified by flash chromatography (100% chloroform, then 99:1 chloroform/methanol) to yield the desired product.

Yield: 0.43 g (33%). R$_f$ 0.30 (98:2 chloroform/methanol). mp 195°–196° C.;

$^1$H NMR (DMSO-d$_6$) δ1.94 (s, CH$_3$CO), 4.34 (d,J=5.7 Hz, CH$_2$), 5.77 (d,J=8.1 Hz, CH), 7.24–7.32 (m, C$_3$'H, C$_5$'H, C$_6$'H, Ph), 7.54 (d,J=7.0 Hz, C$_4$'H or C$_7$'H), 7.62 (d,J=7.0 Hz, C$_4$'H or C$_7$'H), 8.74 (d,J=8.1 Hz, NH), 8.86 (t,J=5.7 Hz, NH).

$^{13}$C NMR (DMSO-d$_6$) 22.27 (CH$_3$CO), 42.30 (CH$_2$), 51.22 (CH), 104.34 (C$_3$'), 110.90 (C$_7$'), 121.05 (C$_4$'), 122.90 (C$_5$'), 124.28 (C$_6$'), 126.73 (C$_3$'$_a$), 127.01 (2C$_2$'' or 2C$_3$''), 127.69 (2C$_2$'' or 2C$_3$''), 128.14 (C$_4$''), 138.87 (C$_1$''), 154.10 (C$_7$'$_a$), 154.30 (C$_2$') 167.40 (CH$_3$CO), 169.26 (CONH) ppm.

IR (KBr) 3230, 1625 (br), 1520 (br), 1440, 1090, 1085, 890,735, 690 cm$^{-1}$;

Mass spectrum, m/e (relative intensity) 322 (5), 279 (1), 264 (1), 234 (1), 215 (5) 189 (45), 146 (100), 130 (11), 118 (7), 91 (87), 65 (16).

High resolution mass spectrum, Calcd for C$_{19}$H$_{18}$N$_2$O$_3$ 322.1317. Found 322.1318.

EXAMPLE 22

Preparation of (D,L)-α-Acetamido-N-benzyl-2-benzo[b]thiopheneacetamide

N-Acetyl-D,L-ethoxyglycine-N-benzylamide (1.00 g, 4 mmol) was suspended in anhydrous ethyl ether (15 mL) and then boron trifluoride etherate (0.91 g, 6.3 mmol) was rapidly added, and the resulting solution was stirred for 15 min. The benzo[b]thiophene (2.14 g, 16 mmol) was then added and the reaction was stirred at room temperature (3 d). The solution was poured into an ice-cold saturated aqueous solution of NaHCO$_3$, and then stirred for 15 min at 0° C. The mixture was extracted with ethyl acetate (2×), and the organic layers were combined, dried (Na$_2$SO$_4$) and evaporated in vacuo to give an orange oil. The oil was triturated with ethyl ether to yield a crystalline product which was filtered and further purified by flash chromatography (99:1 chloroform/n(ethanol) to give the desired product.

Yield: 0.06 g (4%). $R_f$ 0.32 (99:1 chloroform/methanol). mp 226°–227° C.

$^1$H NMR (DMSO-$d_6$) δ1.94 (s, CH$_3$CO), 4.34 (d, J=5.7 Hz, CH$_2$), 5.86 (d, J=8.1 Hz, CH), 7.20–7.38 (m, C$_3$'H, C$_6$'H, C$_7$'H, Ph), 7.77–7.80 (m, C$_4$'H or C$_5$'H), 7.89–7.93 (m, C$_4$'H or C$_5$'H), 8.76 (d, J=8.1 Hz, NH), 8.97 (t,J=5.7 Hz, NH).

$^{13}$C NMR (DMSO-$d_6$) 22.34 (CH$_3$CO), 42.38 (CH$_2$), 52.70 (CH), 122.15 (C$_4$' or C$_7$'), 122.32 (C$_4$' or C$_7$'), 123.45 (C$_3$'), 124.37 (C$_5$' or C$_6$'), 124.41 (C$_5$' or C$_6$'), 126.89 (C$_4$''), 127.27 (2C$_2$'' or 2C$_3$''), 128.27 (2C$_2$'' or 2 C$_3$''), 138.84 (C$_{3'a}$ or C$_{7''a}$), 138.95 (C$_{3'a}$ or C$_{7'a}$), 142.58 (C$_1$'), 168.65 (CH$_3$CO), 169.12 (CONH) ppm. [A distinct signal for the C$_2$' carbon was not detected and is presumed to coincide with the C$_1$' carbon at 142.58 ppm.].

IR (KBr) 3240, 1610 (br), 1510 (br), 1420, 1360, 1215, 1085, 885, 730, 710,685 cm$^{-1}$.

Mass spectrum, m/e (relative intensity) 338 (8), 295 (2), 205 (76), 162 (100), 135 (22), 108 (12), 91 (59).

Elemental Analysis: Calculated: 67.43% C; 5.36% H; 8.28% N. Found: 67.21% C; 5.37 %H; 8.12% N.

EXAMPLE 23

Preparation of (D,L)-α-Acetamido-N-benzyl-3-indoleacetamide

N-Acetyl-D,L-ethoxyglycine-N-benzylamide (0.69 g, 2.75 mmol) was suspended in anhydrous ethyl ether (20 mL) and then boron trifluoride etherate (0.63 g, 4.40 mmol) was rapidly added, and the resulting solution was stirred for 15 min. The indole (1.30 g, 11.00 mmol) was then added and the reaction was stirred at room temperature (22 h). Petroleum ether (35°–60° C.) was added to the reaction, and the resulting semisolid material filtered, and washed with petroleum ether (35°–60° C.). Purification of the reaction mixture was accomplished by flash chromatography (98:2 chloroform/methanol) to produce the title compound as a white solid.

Yield: 0.25 g (18%). $R_f$ 0.14 (95:5 chloroform/methanol) mp 213°–214° C.

$^1$H NMR (DMSO-$d_6$) δ1.90 (s, CH$_3$CO), 4.36 (d,J=6.0 Hz, CH$_2$), 5.72 (d,J=7.2 Hz, CH), 6.90–7.37 (m, Ph, C$_2$'H), 7.02 (dd,J=7.5 Hz, J=7.5 Hz, C$_5$'H or C$_6$'H), 7.12 (dd,J=7.5 Hz, J=7.5 Hz, C$_5$'H or C$_6$'H), 7.39 (d,J=7.5 Hz, C$_4$'H or C$_7$'H), 7.65 (d J=7.5 Hz, C$_4$'H or C$_7$'H), 7.86 (d,J=7.2 Hz, NHCH), 8.13 (t,J=6.0 Hz, NHCH$_2$), 10.30–10.80 (br s, NH).

$^{13}$C NMR (DMSO-$d_6$) 22.32 (CH$_3$CO), 42.23 (CH$_2$), 49.98 (CH), 111.51 (C$_7$'), 112.08 (C$_3$'), 118.76 (C$_4$' or C$_6$'), 119.24 (C$_4$' or C$_6$'), 121.37 (C$_5$'), 123.94 (C$_2$'), 126.58 (C$_{3'a}$), 126.71 (C$_4$''), 127.33 (2C$_2$'' or 2C$_3$''), 128.18 (2C$_2$'' or 2C$_3$''), 136.28 (C$_{7'a}$), 139.44 (C$_1$''), 169.13 (CH$_3$CO), 170.81 (CONH) ppm.

IR (KBr) 3260, 1610 (br), 1515 (br), 1450, 1420, 1370, 1350, 1235, 1095, 895, 735, 715, 695, 600 cm$^{-1}$.

Mass spectrum, m/e (relative intensity) 321 (5), 278 (1), 264 (1), 233 (1), 214 (6), 187 (85), 171 (3), 145 (100), 118 (18), 91 (39).

Elemental Analysis: Calculated: 71.01% C; 5.96% H; 13.06% N. Found: 70.87% C; 6.15% H; 12.78% N.

EXAMPLE 24

Preparation of (D,L)-α-Acetamido-N-benzyl-2-(5-methylpyrrole)acetamide

N-Acetyl-D,L-ethoxyglycine-N-benzylamide (2.00 a, 8 mmol) was suspended in anhydrous ethyl ether (175 mL), and then boron trifluoride etherate (1.38 g, 9.7 mL) was added and the resulting solution stirred (15 min). The 2-methylpyrrole (0.85 g, 10 mmol) was then added and the reaction mixture was stirred under N$_2$ (6 d), during which time the color of the reaction mixture turned reddish brown and a dark-brown deposit formed at the bottom of the flask. The clear solution was decanted and treated with an aqueous saturated NaHCO$_3$ solution containing ice (100 mL) for 30 min. The aqueous reaction mixture was extracted with ethyl acetate (3×30 mL). The combined extracts were dried (Na$_2$SO$_4$) and the solvent removed in vacuo. The brown oily residue was purified by flash column chromatography using 98:2 chloroform/methanol as the eluent to yield the desired compound. The product was recrystallized from ethyl acetate/hexane to give a light yellow amorphous solid.

Yield 0.20 g (94%) $R_f$ 0.44 (95:5, chloroform/methanol). mp 167°–168° C.

$^1$H NMR (DMSO-$d_6$) δ1.87 (s, CH$_3$), 2.13 (s, COCH$_3$), 4.27 (br s, CH$_2$), 5.33 (d,J=7.4 Hz, CH), 5.60 (s, C$_4$H), 5.77 (s, C$_3$H), 7.19–7.30 (m, 5 PhH), 8.22 (d,J=7.4 Hz, NH), 8.45 (t,J=5.5 Hz, NH), 10.38 (s, NH).

$^{13}$C NMR (DMSO-$d_6$) 12.74 (CH$_3$), 22.49 (COCH$_3$), 42.11 (CH$_2$), 51.21 (CH), 105.09 (C$_4$), 106.07 (C$_3$), 126.16 (C$_5$), 126.64 (C$_4$'), 126.85 (C$_2$), 127.09 (2C$_2$' or 2C$_3$'), 128.17 (2C$_2$' or 2C$_3$'), 139.33 (C$_1$'), 168.88 (COCH$_3$), 169.79 (CONH) ppm.

IR (KBr) 3250, 1630, 1520, 1420, 1360, 1300, 1260, 1230, 1160, 1110, 1020 cm$^{-1}$.

Mass spectrum, m/e (relative intensity) 285 (M+,10), 178 (20), 152 (24), 151 (100), 110 (12), 109 (93), 108 (22), 107 (25), 94 (16), 91 (43).

Elemental Analysis: Calculated: 67.35% C; 6.71% H; 14.73% N. Found: 67.57% C; 6.90% H; 14.52% N.

Synthesis of Unsubstituted and Substituted-α-Acetamido-N-benzyl-2-furanacetamides General Procedure. 4-Methylmorpholine (1 equiv) was added to a solution of α-acetamido-2-furanacetic acid (1 equiv) in dry tetrahydrofuran (75 mL/10 mmol) at −10 to −15° C. under N$_2$. After stirring (2 min), isobutyl chloroformate (1 equiv) was added leading to the precipitation of a white solid. The reaction was allowed to proceed for 2 additional minutes and then a solution of the substituted benzylamine (1 equiv) in tetrahydrofuran (10mL/10 mmol) was added over 5 min at −10 to −15° C. The reaction mixture was allowed to stir at room temperature for 5 min and then the 4-methylmorpholine hydrochloride salt filtered. The organic layer was concentrated in vacuo, and the residue was triturated with ethyl acetate, and the remaining white solid filtered. Concentration of the ethyl acetate layer led to additional amounts of the white solid. The desired product was purified by either recrystallization, or flash chromatography of the combined solid material. Examples 25-32 were prepared according to this procedure.

EXAMPLE 25

(D,L)-α-Acetamido-N-benzyl-2-furanacetamide

Using benzyl amine (0.27 g, 2.56 mmol) and racemic α-acetamido-2-furanacetic acid (0.47 g, 2.56 mmol) gave the desired compound. The product was recrystallized from ethyl acetate to give a white solid.

Yield: 0.46 g (65%) $R_f$ 0.30 (98:2 chloroform/methanol). mp 177°–178° C.

$^1$H NMR (DMSO-d$_6$) δ1.90 (s, CH$_3$), 4.31 (d,J=6.0 Hz, CH$_2$), 5.58 (d,J=8.1 Hz, CH), 6.27–6.33 (m, C$_3$H), 6.40–6.44 (m, C$_4$H), 7.20–7.36 (m, 5 PhH), 7.60–7.64 (m, C$_5$H), 8.57 (d,J=8.1 Hz, NH), 8.73 (t,J=6.0 Hz, NH).

EXAMPLE 26

(D,L)-α-Acetamido-N-(2-fluorobenzyl)-2-furanacetamide

Using 2-Fluorobenzylamine (1.13 g, 9.0 mmol) and racemic α-acetamido-2-furanacetic acid (1.50 g, 8.2 mmol) gave the desired product.

Yield: 1.20 g (50%). $R_f$ 0.36 (96:4 chloroform/methanol). mp 193°–195° C. (recrystallized from EtOAc).

$^1$H NMR (DMSO-d$_6$) δ1.89 (s, COCH$_3$), 4.33 (d,J=5.5 Hz, CH$_2$), 5.58 (d,J=8.0 Hz, CH), 6.28 (s, C$_4$H), 6.29 (s, C$_3$H), 7.62 (s, C$_5$H), 7.13–7.35 (m, 4 ArH), 8.61 (d,J=8.0 Hz, NH), 8.76 (t,J=5.5 Hz, NH).

$^{13}$C NMR (DMSO-d$_6$) 22.35 (COCH$_3$), 36.12 (d,J$_{CF}$=6.6 Hz, CH$_2$), 50.88 (CH), 107.64 (C$_4$), 110.43 (C$_3$), 115.04 (d,J$_{CF}$=21.4 Hz, C$_{3'}$), 124.29 (d,J$_{CF}$=4.2 Hz, C$_{5'}$), 125.64 (d,J$_{CF}$=15.0 Hz, C$_{1'}$), 128.94 (d,J$_{CF}$=9.0 Hz, C$_{4'}$ or C$_{6'}$), 129.27 (d,J$_{CF}$=5.5 Hz, C$_{4'}$ or C$_{6'}$), 142.66 (C$_5$), 151.07 (C$_2$), 159.99 (d,J$_{CF}$=244.4 Hz, C$_{2'}$), 168.17 (COCH$_3$), 169.24 (CONH) ppm.

IR (KBr) 3270, 1630, 1520, 1440, 1360, 1220, 1180, 1140, 1100, 1000, 740 cm$^{-1}$.

Mass spectrum, m/e (relative intensity) 291 (M$^+$+1, 3), 274 (2), 247(3), 165 (4), 145 (10), 139 (98), 138 (46), 126 (7), 110 (10), 109 (65), 97 (93), 96 (100).

Elemental Analysis: Calculated: 62.02% C; 5.21% H; 9.65% N. Found: 62.20% C; 5.19% H; 9.69% N.

EXAMPLE 27

(D,L)-α-Acetamido-N-(3-fluorobenzyl)-2-furanacetamide

Making use of 3-fluorobenzylamine (1.13 g, 9.0 mmol) and racemic α-acetamido-2-furanacetic add (1.50 g, 8.2 mmol) gave the desired product.

Yield 1.90 g (80%). $R_f$ 0.30 (96:4 chloroform/methanol). mp 163°–165° C. (recrystallized from ethyl acetate).

$^1$H NMR (DMSO-d$_6$) δ1.89 (s, COCH$_3$), 4.31 (d,J=5.5 Hz, CH$_2$), 5.55 (d,J=7.8 Hz, CH), 6.31 (s, C$_4$H), 6.42 (s, C$_3$H), 6.98–7.37 (m, 4 ArH), 7.62 (s, C$_5$H), 8.61 (d,J=7.8 Hz, NH), 8.70 (t,J=5.5 Hz, NH).

$^{13}$C NMR (DMSO-d$_6$) 22.35 (COCH$_3$), 41.71 (CH$_2$), 51.01 (CH), 107.73 (C$_4$), 110.59 (C$_3$), 113.50 (d,J$_{CF}$=21.6 Hz, C$_{2'}$ or C$_{4'}$), 113.60 (d,J$_{CF}$=22.3 Hz, C$_{2'}$ or C$_{4'}$), 122.95 (br, C$_{6'}$), 130.18 (d,J$_{CF}$=8.6 Hz, C$_{5'}$), 142.21 (d,J$_{CF}$=7.5 Hz, C$_{1'}$), 142.66 (C$_5$), 151.03 (C$_2$), 162.28 (d,J$_{CF}$=243.3 Hz, C$_{3'}$), 168.23 (COCH$_3$), 169.31 (CONH) ppm.

IR (KBr) 3230, 1630, 1540, 1440, 1360, 1220, 1140, 1000, 730 cm$^{-1}$.

Mass spectrum, m/e (relative intensity) 290 (M$^+$, 71), 231 (7), 165 (18), 140 (23), 139 (100), 126 (16), 109 (6), 97 (118), 96 (100), 96 (30).

Elemental Analysis: Calculated: 62.02% C; 5.21% H; 9.65% N. Found: 61.97% C; 5.35% H; 9.53% N.

EXAMPLE 28

(D,L)-α-Acetamido-N-(4-fluorobenzyl)-2-furanacetamide

Using racemic α-acetamido-2-furanacetic acid (1.50 g, 8.2 mmol) and 4-fluorobenzylamine (1.13 g, 9.0 mmol) gave the desired product.

Yield 2.10 g (88%). $R_f$ 0.30 (96:4 chloroform/methanol). mp 188°–190° C. (recrystallized from ethyl acetate).

$^1$H NMR (DMSO-d$_6$) δ1.88 (s, COCH$_3$), 4.27 (d,J=5.5 Hz, CH$_2$), 5.55 (d,J=8.0 Hz, CH), 6.27 (s, 1H), 6.41 (s, 1H), 7.09–7.15 (m, 2ArH), 7.12–7.27 (m, 2 ArH), 7.61 (s, 1H), 8.58 (d,J=8.0 Hz, NH), 8.75 (t,J=5.5 Hz, NH).

$^{13}$C NMR (DMSO-d$_6$) 22.28 (COCH$_3$), 41.51 (CH$_2$), 50.87 (CH), 107.52 (C$_4$), 110.46 (C$_3$), 114.90 (d,J$_{CF}$=21.1 Hz, C$_{3'}$), 129.48 (d,J$_{CF}$=8.3 Hz, C$_{2'}$), 135.23 (d,J$_{CF}$=3.2 Hz, C$_{1'}$), 142.53 (C$_5$), 151.08 (C$_2$), 161.12 (d,J$_{CF}$=242.2 Hz, C$_{4'}$), 167.95 (COCH$_3$), 169.13 (CONH) ppm.

IR (KBr) 3230, 1620, 1500, 1360, 1320, 1260, 1210, 1140, 1000, 820, 780, 730 cm$^{-1}$.

Mass spectrum, m/e (relative intensity) 291 (M$^+$+1,4), 165 (4), 140 (9), 139 (92), 138 (52), 124 (G), 109 (71), 97 (60), 96 (100).

Elemental Analysis: Calculated: 62.02% C; 5.21% H; 9.65% N. Found: 61.76% C; 5.41% H; 9.43% N.

EXAMPLE 29

(D,L)-α-Acetamido-N-(2,5-difluorobenzyl)-2-furanacetamide

Using 2,5-difluorobenzylamine (1.30 g, 9.0 mmol) and racemic α-acetamido-2-furanacetic acid (1.50 g, 8.2 mmol) gave the desired product.

Yield 1.60 g (64%). $R_f$ 0.38 (96:4 chloroform/methanol). mp 177°–178° C. (recrystallized from ethyl acetate).

$^1$H NMR (DMSO-d$_6$) δ1.89 (s, COCH$_3$), 4.31 (d,J=5.5 Hz, CH$_2$), 5.55 (d,J=7.7 Hz, CH), 6.32 (s, C$_4$H), 6.43 (s, C$_3$H), 7.22–7.25 (m, 3 ArH), 7.62 (s, C$_5$H), 8.62 (d,J=7.7 Hz, NH), 8.78 (t,J=5.5 Hz, NH).

$^{13}$C NMR (DMSO-d$_6$) 22.30 (COCH$_3$), 35.98 (d,J$_{CF}$=5.8 Hz, CH$_2$), 51.02 (CH), 107.81 (C$_4$), 110.58 (C$_3$), 115.06 (dd,J$_{CF}$=19.5, 25.6 Hz, C$_{3'}$ or C$_{6'}$), 115.16 (dd,J$_{CF}$=15.6, 24.7 Hz, C$_{3'}$ or C$_{6'}$), 116.52 (dd,J$_{CF}$=10.1, 23.9 Hz, C$_{4'}$), 127.98 (dd,J$_{CF}$=9.2, 17.7 Hz, C$_{1'}$), 142.69 (C$_5$), 150.78 (C$_2$), 155.89 (d,J$_{CF}$=239.0 Hz, C$_{2'}$ or C$_{5'}$), 158.18 (d,J$_{CF}$=238.8 Hz, C$_{2'}$ or C$_{5'}$), 168.38 (COCH$_3$), 169.35 (CONH) ppm.

IR (KBr) 3230, 1620, 1520, 1480, 1360, 1260, 1230, 1180, 1140, 1000, 860, 810, 730, 710 cm$^{-1}$.

Mass spectrum, m/e (relative intensity) 309 (M$^+$+1, 1), 266 (1), 222(1), 165 (5), 140 (5), 139 (61), 138 (36), 127 (37), 97 (44), 96 (100).

Elemental Analysis: Calculated: 58.44% C; 4.58% H; 9.09% N. Found: 58.68% C; 4.69% H; 8.87% N.

EXAMPLE 30

(D,L)-α-Acetamido-N-(2,6-difluorobenzyl)-2-furanacetamide

Marking use of 2,6-difluorobenzylamine (1.30 g, 9.0 mmol) and racemic α-acetamido-2-furanacetic acid (1.50 g. 8.2 mmol) the desired product was formed.

Yield 1.90 g (73%). mp 237°–239° C. (recrystallized from ethanol). $^1$H NMR (DMSO-d$_6$) δ1.86 (COCH$_3$), 4.33 (d,J=4.5 Hz, CH$_2$), 5.53 (d,J=8.3 Hz, CH), 6.17 (s, C$_4$H), 6.38 (s, C$_3$H), 7.05–7.10 (m, 2 ArH), 7.36–7.41 (m, 1 ArH), 7.60 (s, C$_5$H), 8.52 (d,J=8.3 Hz, NH), 8.66 (t,J=4.5 Hz, NH).

$^{13}$C NMR (DMSO-d$_6$) δ22.33 (COCH$_3$), 30.74 (t,J$_{CF}$=4.4 Hz, CH$_2$), 50.48 (CH), 107.24 (C$_4$), 110.40 (C$_3$), 111.61 (dd,J$_{CF}$=8.0, 25.1 Hz, C$_{3'}$, C$_{5'}$), 113.67 (t,J$_{CF}$=19.5 Hz, C$_{1'}$), 129.98 (t,J$_{CF}$=10.5 Hz, C$_{4'}$), 142.50 (C$_5$), 151.23 (C$_2$), 160.93 (d,J$_{CF}$=248.1, C$_{2'}$ or C$_{6'}$), 161.10 (d,J$_{CF}$=248.1 Hz, C$_{2'}$ or C$_{6'}$), 167.59 (COCH$_3$), 169.00 (CONH) ppm.

IR (KBr) 3230, 1620, 1530, 1460, 1360, 1320, 1260, 1220, 1160, 1140, 1030, 1000, 820 780, 750, 740, 710 cm$^{-1}$.

Mass spectrum, m/e (relative intensity) 309 (M$^+$ +1, 4), 265 (2), 165 (4), 147 (7), 140 (8), 139 (87), 138 (36), 127 (54), 97 (58), 96 (100).

Elemental Analysis: Calculated: 58.44% C; 4.58% H; 9.09% N. Found: 58.62% C; 4.74% H; 8.99% N.

EXAMPLE 31

(D)-(−)-α-Acetamido-N-benzyl-2-furanacetamide

Starting with D-α-acetamido-2-furanacetic acid (2.45 g, 13.38 mmol) and benzylamine (1.43 g, 13.38 mmol), the desired product was obtained. Yield: 2.54 g (70%) The product was further recrystallized from ethyl acetate to give the title compound.

Yield: 2.30 g mp 196°–197° C. [α]$^{26}$D[c=1, MeOH]=−78.3°. Addition of R(−)-mandelic acid to a CDCl$_3$ solution the product gave only one signal for the acetamide methyl protons. Mass spectrum, m/e (relative intensity) 272 (M$^+$, 2), 184(2), 165 (2), 140 (8), 139(88), 138 (34), 97 (46), 96 (100), 91 (63).

Elemental Analysis: Calculated: 66.16% C; 5.92% H; 10.29% N. Found: 66.09% C; 6.01% H; 10.38% N.

EXAMPLE 32

(L)-(+)-α-Acetamido-N-benzyl-2-furanacetamide

Using L-α-acetamido-2-furanacetic acid (2.83 g, 15.46 mmol) and benzylamine (1.65 g, 15.4G mmol) gave 3.80 g of the enriched desired product. $^1$H NMR analysis with R(−)-mandelic acid showed that it was greater than 80% enriched in the title compound. The pure L-enantiomer was obtained by recrystallization from absolute ethanol.

Yield: 1.60 g. mp 196°–197° C. [α]$^{26}$D[c=1, MeOH]=+79.0°.

Mass spectrum, m/e (relative intensity) 273 (M$^+$ +1,3), 229 (2), 214 (2), 184 (1), 165 (7), 157 (4), 140 (33), 139 (100), 138 (95), 97(98), 96 (100), 91 (98).

Elemental Analysis: Calculated: 66.16% C; 5.92% H; 10.29% N. Found: 65.89% C; 5.86% H; 10.42% N.

EXAMPLE 33

Resolution of (D,L)-α-Acetamido-2-furanacetic acid Using (R)-(+)-α-Methylbenzylamine and (S)-(−)-α-Methylbenzylamine (R)-(+)-α-Methylbenzylamine (13.22 g, 0.11 mol) was added to an absolute ethanol solution (550 mL) of racemic α-acetamido-2-furanacetic acid (20.00 g, 0.11 mol). The resulting solution was cooled in the freezer overnight. The white precipitate (12.00 g) which separated upon cooling was filtered, and the mother liquid evaporated to give a salt which was later used for obtaining L-α-acetamido-2-furanacetic acid. The initial salt was recrystallized (3×) from absolute ethanol to yield 4.00 g of the pure diasteromeric salt.

mp 173°–175° C. [α]$^{26}$D[c=1, MeOH]=−108.

Elemental Analysis Calculated: 63.14% C; 6.62% H; 9.21% N. Found: 63.19% C; 6.62% H; 9.12% N.

The purified salt was treated with 5% aqueous NH$_4$OH solution, extracted with ethyl ether (3×50 mL), and then acidified with a 8.5% aqueous solution of H$_3$PO$_4$ and then extracted with ethyl acetate (3×100 mL) to yield 2.45 g(25%) of D-α--acetamido-2-furanacetic acid.

mp 169°–171° C.

[α]$^{26}$D[c=1, MeOH]=−184.2°.

Elemental Analysis: Calculated: 52.46% C; 4.95% H: 7.65% N. Found: 52.17% C; 4.89% H: 7.56% N.

The salt obtained after evaporation of the main mother liquor was hydrolysed with 5% aqueous NH$_4$OH solution to give 10.10 g of the enriched L-α-acetamido-2-furanacetic acid [[α]$^{26}$D[c=1, MeOH]=+47.7°]. (S)-(−)-methylbenzylamine (6.70 g, 0.055 mol) was added to a solution of enriched L-α-acetamido-2-furanacetic acid (10.10 g, 0.055 mol) in absolute ethanol (275 mL). The white precipitate of the diasteroemeric salt (8.10 g) that separated upon cooling the solution in the freezer (1 h) was filtered. The salt was recrystallized from absolute ethanol (3×) to yield 3.00 g of the salt, mp 172°–174° C. [α]$^{26}$D[c=1, MeOH]=+106°.

Elemental Analysis: Calculated: 63.14% C; 6.62% H; 9.21% N. Found: 63.18% C; 6.47% H: 9.00% N.

The salt from the third recrystallization was treated with a 5% aqueous NH$_4$OH solution and extracted with ethyl ether (3×50 mL), and then acidified with a 8.5% aqueous solution of H$_3$PO$_4$, and then extracted with ethyl acetate (3×100 mL) to give 1.63 g (32%) of L-α-acetamido-2-furanacetic acid.

mp 169°–171° C. [α]$^{26}$D[c=1, MeOH]=+182°.

EXAMPLE 34

Enzymatic Separation of D(−)α-acetamido-2-furanacetic acid from DL (±)α-acetamido-2-furanacetic acid DL (±)α-acetamido-2-furanacetic acid (2.00 g, 10.9 mmol) was suspended in deionized H$_2$O (600 mL). An aqueous solution of LiOH (1N) was added to this suspension dropwise until all of the acid had dissolved and the pH was 7.2. Acylase 1, Grade II (20 mg, activity=900 units/mg, Sigma Chemical Company, Cat. No. A 8376) was then added to the above solution and the mixture stirred at 34°–37° C. (41 h). The suspension was then cooled to room temperature and acidified to pH 1.5 with aqueous 1N HCl. The suspended material was filtered, and the filtrate was saturated with solid NaCl, and then extracted with ethyl acetate (3×250 mL). The combined ethyl acetate extracts was dried (Na$_2$SO$_4$). The solvent was removed in vacuo and the residue was triturated with ethyl acetate (10 mL). The white solid (0.75 g) that remained was filtered and was pure D(−)α-acetamido-2-furanacetic acid; mp 168°–169° C., mixed mp with an authentic sample 168°–169° C.; [α]$_D^{26}$[c=1, MeOH]=−184.3°.

EXAMPLE 35

Preparation of D,L-α-Acetamido-2-furanacetic Acid

An ethereal solution of ZnCl$_2$(1N, 28 mL, 0.028 mol) was added to a stirred solution of ethyl acetamido-2-bromoacetate (4.40 g, 0.019 mol) and furan (11.23 g, 0.165 mol) in dry tetrahydrofuran (100 mL), and allowed to stir at room temperature (5 h). The mixture was then treated with H$_2$O (50 mL), the organic phase separated, and the aqueous layer extracted with CH$_2$Cl$_2$ (2×100 mL). The organic layers were combined, dried (Na$_2$SO$_4$) and the volatile materials were removed by distillation in vacuo to give approximately 4.00 g (97%) of light-brown semi-solid material. TLC analysis showed a major spot at R$_f$ 0.30 (99:1 chloroform/methanol). The desired compound, D,L-ethyl α-acetamido-2-furanacetate, was purified by flash column chromatography on silica gel using 99:1 chloroform/methanol as the eluent to give 3.60 g (87%) of a beige solid.

mp 68°–70° C.

D,L-Ethyl α-acetamido-2-furanacetate (4.00 g, 19 mmol) was dissolved in 90:10 ethanol/water (150 mL) and then KOH (2.00 g, 35 mmol) was added and the resulting solution stirred at room temperature (48 h). The reaction was concentrated in vacuo and the residue diluted with H$_2$O and then washed with ethyl ether (3×50 mL). The aqueous layer was then made acidic with a 8.5% aqueous solution of H$_3$PO$_4$ and extracted with ethyl acetate (3×150 mL). The organic layers were combined, dried (Na$_2$SO$_4$), evaporated to dryness in vacuo to give the desired compound.

Yield: 2.65 g (76%). R$_f$ 0.37 (8:1:1 isopropanol/NH$_4$OH/H$_2$O). mp 172°–174° C.

EXAMPLE 36

Synthesis of (D,L)-2-Acetamido-4-pentenoic Acid-N-benzylamine

4-Methylmorpholine (0.55 g, 5.40 mmol) was added to a stirred solution of 2-acetamido-4-pentenoic acid (0.81 g, 5.18 mmol) in dry tetrahydrofuran (60 mL) at −10 to −15° C. under N$_2$. After stirring (2 min), isobutyl chloroformate (0.75 g, 5.70 mmol) was added leading to the precipitation of a white solid. The reaction was allowed to proceed for 2 additional minutes and then a solution of benzylamine (0.61 g, 5.70 mmol) in tetrahydrofuran (10 mL) was added slowly at −10 to −15° C. After stirring (5 min) at room temperature, the insoluble salt was removed by filtration. The filtrate was evaporated to dryness and the residue was triturated with ethyl acetate, and the remaining white solid was filtered to yield the desired product.

Yield 0.81 g (64%). R$_f$ 0.36 (4% methanol/chloroform). mp 118°–120° C. (recrystallized from ethyl acetate/cyclohexane).

$^1$H NMR (DMSO-d$_6$) δ1.83 (s, COCH$_3$), 2.22–2.49 (m, CH$_2$CH=CH$_2$), 4.26(d,J=5.3 Hz, CH$_2$Ph), 4.25–4.33 (m, CH), 4.99–5.09 (m, CH$_2$CH=CH$_2$), 7.21–7.29 (m, 5 PhH), 8.05 (d,J=7.6 Hz, NH), 8.46 (br s, NH).

$^{13}$C NMR (DMSO-d$_6$) 22.41 (COCH$_3$), 36.24 (CH$_2$CH=CH$_2$), 41.91 (CH$_2$Ph), 52.20 (CH), 117.15 (CH$_2$CH=CH$_2$), 126.54 (C$_4'$), 126.99 (2C$_2'$ or 2C$_3'$), 1:28.04 (2C$_2'$ or 2C$_3'$), 134.25 (CH$_2$CH=CH$_2$), 139.22 (C$_1'$), 169.0:2 (COCH$_3$), 170.96 (CONH) ppm.

Mass spectrum, m/e (relative intensity) 246 (M+, 4), 205 (4), 163 (15), 140 (8), 106 (33), 91 (77), 70 (100).

Elemental Analysis: Calculated: 68.27%C; 7.37% H; 11.37% N. Found: 68.55% C; 7.31% H; 11.48% N.

Mass spectrum m/e (relative intensity) 292 (M+ +1, 1), 233 (8), 158 (19), 157 (100), 116 (26), 115 (100), 106 (29), 91 (72).

Elemental Analysis: Calculated: 61.84% C; 7.26% H; 14.42% N. Found: 61.67 % C; 7.10% H; 14.14% N.

EXAMPLE 37

Synthesis of (D,L)-2-Acetamido-N-benzyl-2-(1-morpholine)acetamide

A mixture of ethyl 2-acetamido-2-(1-morpholine)acetate (0.59 g, 2.56 mmol), benzylamine (0.28 g, 9..82 mmol) and sodium cyanide (0.01 g, 0.26 mmol) in methanol (5 mL) was stirred at 50°–55° C. for 18 hr. The solvent was removed in vacuo and the residue triturated with ethyl acetate (5 mL). The white solid (0.35 g) that remained was collected by filtration and identified as the desired compound. The filtrate was concentrated and the residue purified By flash column chromatography (2% methanol/chloroform) on SiO$_2$. The initial fractions gave a trace amount (0.09 g) of (D,L)-2-acetamido-N-benzyl-2-(N-benzylamine)acetamide. Continued elution gave additional amounts (0.20 g) of the title compound.

(D,L)-2-Acetamido-N-benzyl-2-(N-benzylamine)acetamide:

Yield: 0.09 g (11%). mp 135°–138° C.

$^1$H NMR (DMSO-d$_6$) δ1.83 (s, COCH$_3$), 3.56 (d,J=13.6 Hz, NHCH), 3.66 (d,J=13.6 Hz, NHCH), 4.23 (d,J=5.4 Hz, CH$_2$), 4.89 (d,J=8.0 Hz, CH), 7.05–7.38 (m, 10 PhH), 8.20 (d,J=8.0 Hz, NH), 8.51 (t,J=5.4 Hz, NH).

$^{13}$C NMR (DMSO-d$_6$) 22.63 (COCH$_3$), 42.11 (CH$_2$), 48.57 (NHCH$_2$), 64.41 (CH), 126.65 (C$_4$), 126.70 (C$_4'$), 127.13, 128.00, 128.13, 128.22, 139.24 (C$_1$ or C$_1'$), 140.12 (C$_1$ or C$_1'$), 169.61 (COCH$_3$), 169.90 (CONH) ppm.

(D,L)-2-Acetamido-N-benzyl-2-(1-morpholine)acetamide.

Yield: 0.48 g (64%). R$_f$ 0.35 (4% methanol/chloroform). mp 171°–172° (recrystallized from ethyl acetate).

$^1$H NMR (DMSO-d$_6$) δ1.86 (s, COCH$_3$), 2.30–2.40 (m, CH$_2$NCH$_2$), 3.51 (br s, CH$_2$OCH$_2$), 4.18–4.33 (m, CH$_2$), 5.07 (d,J=8.9 Hz, CH), 7.18–7.25 (m, 5 PhH), 8.23 (d,J=8.9 Hz, NH), 8.58 (br s, NH).

$^{13}$C (DMSO-d$_6$) 22.39 (COCH$_3$), 42.20 (CH$_2$), 48.43 (CH$_2$NCH$_2$), 66.03 (CH), 69.24 (CH$_2$OCH$_2$), 126.76 (C$_4'$), 127.13 (2C$_2'$ or 2C$_3'$), 128.23 (2C$_2'$ or 2C$_3'$), 139.42 (C$_1'$), 168.02 (COCH$_3$), 170.20 (CONH) ppm.

EXAMPLE 38

Synthesis of (D,L)-Ethyl-2-acetamido-2-(ethylamino)acetate

A cold (−78° C.) solution of ethyl 2-acetamido-2-bromoacetate (2.10 g, 9.38 mmol) in dry tetrahydrofuran (80 mL) was added slowly into a cooled (−78° C.) tetrahydrofuran (20 mL) solution of methylamine (1.40 g, 31.04 mmol) over a period of 20 min. The reaction was stirred at −78° C. (1 h), and then at room temperature (1 h). The precipitated salt was filtered and the filtrate concentrated. The residue was purified by flash column chromatography on SiO$_2$ using 3% methanol/chloroform as the eluent to yield the desired compound as a light yellow oil.

Yield: 0.90 (51%).

R$_f$0.36 (4% methanol/chloroform).

$^1$H NMR (CDCl$_3$) 0.93 (t,J=6.7 Hz, NHCH$_2$CH$_3$), 1.12 (t,J=6.8 Hz, OCH$_2$CH$_3$), 1.87 (s, COCH$_3$), 2.48 (q,J=6.7 Hz, NHCH$_2$CH$_3$), 4.05 (q,J=6.8 Hz,

OCH$_2$CH$_3$), 5.05 (d,J=7.1 Hz, CH), 7.09 (d,J=7.1 Hz, NH).

$^{13}$C NMR (CDCl$_3$) 13.64 (NHCH$_2$CH$_3$), 14.55 (OCH$_2$CH$_3$), 22.53 (COCH$_3$), 39.06 (NHCH$_2$CH$_3$), 61.38 (CH), 64.14 (OCH$_2$CH$_3$), 170.09 (COCH$_3$), 170.20 (COOCH$_2$CH$_3$) ppm.

EXAMPLE 39

Using the procedures described herein, the following examples are also prepared:

(D,L)α-Acetamido-N-benzyl-3-furanacetamide (D,L)α-Acetamido-N-(2-fluorobenzyl)-3-furanacetamide (D,L)α-Acetamido-N-(3-fluorobenzyl)-3-furanacetamide (D,L)α-Acetamido-N-(4-fluorobenzyl)-3-furanacetamide α-Acetamide-N-benzyl-2-aminoacetamide Preparation of α-Heteroatom Substituted Amino Acids, Synthesis of Ethyl 2-Acetamido-2-substituted Acetates, General Procedure A cooled (−78° C.) solution of ethyl 2-bromo-2-acetamidoacetate (1 equiv) in THF (1 mmol/10 mL) was added slowly to a THF (1 mmol/4 mL) solution of the nitrogen nucleophile (5–10 equiv) at −78° C. The reaction was stirred at this temperature (0.5 h) and then at room temperature (1 h). The insoluble materials were filtered and washed with THF. The filtrate was concentrated in vacuo and the residue was purified by flash chromatography on SiO$_2$ gel (using the indicated solvent as the eluent) to give the desired product.

Using this procedure the following examples were prepared.

EXAMPLE 40

Synthesis of Ethyl 2-Acetamido-2-aminoacetate

Ethyl 2-bromo-2-acetamidoacetate (2.00 g, 8.93 mmol) and liquid NH$_3$ (5–6 equiv) yielded a light brown residue, which on purification by flash column chromatography on SiO2 gel (5% MeOH/CHCl$_3$) gave the desired product as a yellow oil.

Yield: 1.00 g (70%). R$_f$0.21 (5% MeOH/CHCl$_3$).

$^1$H NMR (CDCl$_3$) δ1.31 (t,J=7.1 Hz, 3H), 2.03 (s, 3H), 2.61 (br s, 2H), 4.24 (q,J=7.1 Hz, 2H), 5.21 (d,J=7.1 Hz, 1H), 7.50 (d,J=7.1 Hz, 1H).

$^{13}$C NMR (CDCl$_3$) 13.72, 22.68, 59.70, 61.73, 170.40, 170.68 ppm.

EXAMPLE 41

Synthesis of Ethyl 2-Acetamido-2-(methylamino)acetate

Use of ethyl 2-bromo-2-acetamidoacetate (2.00 g, 8.93 mmol) and MeNH$_2$ (2.50 g, 80.6 mmol) gave an oily residue (1.50 g). The residue was purified by flash column chromatography on SiO$_2$ gel (3% MeOH/CHCl$_3$) to yield the desired product as an oil.

Yield: 1.00 g (65%).

$^1$H NMR (CDCl$_3$) δ1.32 (t,J=7.1 Hz, 3H), 2.07 (s, 3H), 2.36 (s, 3H), 4.26 (q,J=7.1 Hz, 2H), 5.20 (d,J=7.4 Hz, 1H), 6.60 (br s, 1H).

$^{13}$C NMR (CDCl$_3$) 14.02, 23.06, 30.84, 62.04, 65.72, 170.09, 170.40 ppm.

EXAMPLE 42

Synthesis of Ethyl 2-Acetamido-2-(N,N-dimethylamino)acetate

Ethyl 2-bromo-2-acetamidoacetate (2.00 g, 8.93 mmol) and Me$_2$NH (5–6 equiv) gave the desired product as a yellow oil.

Yield: 1.50 g (89%).

$^1$H NMR (CDCl$_3$) δ1.25 (t,J=7.1 Hz, 3H), 2.02 (s, 3H), 2.23 (s, 6H), 4.10–4.25 (m, 2H), 5.24 (d,J=8.3 Hz, 1H), 6.59 (d,J=8.3Hz, 1H).

$^{13}$C NMR (CDCl$_3$) 14.05, 23.00, 40.28 (2 C), 61.84, 69.24, 169.38, 170.57 ppm.

EXAMPLE 43

Synthesis of Ethyl 2-Acetamido-2-(4-morpholine)acetate

Using morpholine (1.71 g, 19.64 mmol) and ethyl 2-bromo-2-acetamidoacetate (2.00 g, 8.93 mmol) gave an oily residue, which was purified by flash column chromatography on SiO2 gel (2% MeOH/CHCl$_3$) to give the desired product as a thick oil.

Yield: 1.90 g (93%). R$_f$0.29 (3% MeOH/CHCl$_3$).

$^1$H NMR (CDCl$_3$) δ1.32 (t,J=6.8 Hz, 3H), 2.07 (s, 3H), 2.43–2.72 (m, 4H 3.58–3.78 (m, 4H), 4.26 (q,J=6.8 Hz, 2H), 5.27 (d,J=7.9 Hz, 1H), 6.39 (d,J=7.9 Hz, 1H).

$^{13}$C NMR (CDCl$_3$) 14.21, 23.25, 48.47 (2 C), 62.06, 66.71 (2C), 69.22, 169.00, 170.46 ppm.

EXAMPLE 44

Synthesis of Ethyl 2-Acetamido-2-(N-anilino)acetate

Use of aniline (1.83 g, 19.6 mmol) and ethyl 2-bromo-2-acetamidoacetate (2.00 g, 8.93 mmol) provided a brown residue which was purified by flash column chromatography on SiO$_2$ gel (CHCl$_8$-2% MeOH/CHCl$_3$ gradient) to yield the desired product.

Yield: 1.80 g (85%). R$_f$0.52 (4% MeOH/CHCl$_3$). mp 87°–89° C. (recrystallized from ethyl acetate/petroleum ether).

$^1$H NMR (CDCl$_3$) δ1.29 (t,J=7.1 Hz, 3H), 1.84 (s, 3H), 4.27 (q,J=7.1 Hz, 2H), 5.89 (d,J=8.2 Hz, 1H), 6.43 (d,J=8.2 Hz, 1H), 6.68–6.71 (m, 2H), 6.80–6.83 (m, 1H), 7.17–7.22 (m, 2H). The remaining amino proton was not detected.

$^{13}$C NMR (CDCl$_3$) 13.96, 22.98, 60.19, 62.41, 11.87 (2C), 119.29, 129.37 (2C), 144.09, 169.77, 170.14 ppm.

IR (KBr) 3340, 1720, 1635, 1590, 1490, 730, 710 cm$^{-1}$.

Mass spectrum (FD) 237 (M$^+$+1).

Elemental analysis Calculated for C$_{12}$H$_{16}$N$_2$O$_3$ 61.00% C; 6.83% H; 11.86% N. Found 60.88%C; 6.56% H; 12.00% N.

EXAMPLE 45

Synthesis of Ethyl 2-Acetamido-2-(N-(3-pyrazolylamino))acetate

Using ethyl 2-bromo-2-acetamidoacetate (2.00 g, 8.92 mmol) and 3-aminopyrazole (1.85 g, 22.32 rental) and purification of the reaction product by chromatography on SiO$_2$ gel (2% MeOH/CHCl$_3$) gave the desired product as a yellow oil.

Yield: 1.80 g (89%). R$_f$0.35 (8% MeOH/CHCl$_3$).

$^1$H NMR (CDCl$_3$) δ1.21 (t,J=7.1 Hz, 3H), 1.89 (s, 3H), 4.20 (q,J=7.1. Hz 2H), 5.64 (d,J=1.8 Hz, 1H), 5.71 (br s, 1H), 5.73 (d,J=7.1 Hz, 1H), 7.29 (d,J=1.8 Hz,

1H), 7.98 (d,J=7.1 Hz, 1H). The remaining amino proton was not detected.

$^{13}$C NMR (CDCl$_3$) 13.73, 22.49, 61.41, 62.02, 91.79, 130.53, 153.02, 169.96, 170.93 ppm.

EXAMPLE 46

Synthesis of Ethyl 2-Acetamido-2-(N-hydroxyamino)acetate

Using ethyl 2-bromo-2-acetamidoacetate (2.10 g, 9.37 mmol) and anhydrous NH$_2$OH (0.93 g, 28.00 mmol) gave an oily residue. The residue was purified by flash column chromatography on SiO$_2$ gel (5% MeOH/CHCl$_3$) to give the desired product. The product was recrystallized from EtOH to give a white flaky solid.

Yield: 1.00 g (61%). R$_f$0.24 (5% MeOH/CHCl$_3$). mp 119°–121° C.

$^1$H NMR (DMSO-d$_6$) δ1.19 (t,J=6.9 Hz, 3H), 1.87 (s, 3H), 4.10 (q,J=6.9 Hz, 2H), 5.09 (dd,J=4.0, 8.0 Hz, 1H), 6.06 (br s, 1H), 7.63 (s, 1H), 8.50 (d,J=8.0 Hz, 1H)

$^{13}$C NMR (DMSO-d$_6$) 14.05, 22.46, 60.82, 67.37, 169.19, 169.48 ppm.

IR (KBr) 3300, 1750, 1660, 1540, 1390, 610 cm$^{-1}$.

Mass spectrum (FD) 177 (M$^+$+1).

Elemental analysis Calculated for C$_6$H$_{12}$N$_2$O$_4$ 40.91% C; 6.87% H; 15.90% N. Found 40.79% C; 6.87% H; 15.90% N.

EXAMPLE 47

Synthesis of Ethyl 2-Acetamido-2-(N-(N-methylhydroxyamino))acetate

MeNHOH (17.39 mmol) (prepared from MeNHOH-HCl (2.00 g, 23.95 mmol) and NaOMe (0.94 g, 17.39 mmol)), and ethyl 2-bromo-2-acetamidoacetate (1.00 g, 4.46 mmol) gave an oily residue. The residue was triturated with EtOAc (5 mL) and the solid that remained was filtered and recrystallized from EtOH to give the desired product as a white solid.

Yield: 0.70 g (82%). R$_f$0.34 (5% MeOH/CHCl$_3$). mp 148°–150° C.

$^1$H NMR (DMSO-d$_6$) δ1.17 (t,J=7.0 Hz, 3H), 1.89 (s, 3H), 2.37 (s, 3H), 4.00–4.20 (m, 2H), 5.04 (d,J=9.2 Hz, 1H), 8.17 (s, 1H), 8.43 (d,J=9.2 Hz, 1H).

$^{13}$C NMR (DMSO-d$_6$) 14.04, 22.28, 43.78, 60.79, 71.46, 168.29, 170.23 ppm.

IR (KBr) 3320, 3200 (br), 1760, 1660, 1530, 1470, 720, 640 cm$^{-1}$.

Mass spectrum (FD) 192 (M$^+$+1).

Elemental analysis Calculated for C$_7$H$_{14}$N$_2$O$_4$·0.25 H$_2$O 43.18% C; 7.51% H; 14.39% N. Found 43.28% C; 7.25% H; 14.64% N.

EXAMPLE 48

Synthesis of Ethyl 2-Acetamido-2-(N-(N,O-dimethylhydroxyamino))acetate

MeNHOMe (17.40 mmol) (prepared from MeNHOMe-HCl (2.18 g, 22.32 mmol) and NaOMe (0.94 g, 17.40 mmol)) and ethyl 2-bromo-2-acetamidoacetate (1.00 g, 4.46 mmol) gave a residue which was purified by flash column chromatography on SiO$_2$ gel (1% MeOH/CHCl$_3$) to give the desired product as an oil.

Yield: 0.(30 g (66%). R$_f$0.53 (2% MeOH/CHCl$_3$).

$^1$H NMR (CDCl$_3$) δ1.35 (t,J=7.0 Hz, 3H), 2.12 (s, 3H), 2.62 (s, 3H), 3.46 (s, 3H), 4.30 (q,J=7.0 Hz, 2H), 5.36 (d,J=8.9 Hz, 1H), 6.66 (d,J=8.9 Hz, 1H).

$^{13}$C NMR (CDCl$_3$) 14.06, 22.89, 40.30, 60.01, 61.89, 70.16, 168.14, 170.53 ppm.

Synthesis of 2-Acetamido-N-benzyl-2-substituted Acetamides, General Procedure A mixture of the ethyl 2-substituted-2-acetamidoacetate (1 equiv), benzylamine (1.2 equiv), and NaCN (0.1 equiv) in MeOH (1 mmol/25 mL) was stirred at 45°–50° C. (18 h). The solvent was removed in vacuo and the residue was purified using either trituration with EtOAc or flash column chromatography on SiO$_2$ gel with the indicated solvent as the eluent.

Using this procedure the following examples were prepared.

EXAMPLE 49

Synthesis of 2-Acetamido-N-benzyl-2-aminoacetamide

Ethyl 2-acetamido-2-aminoacetate (1.00 g, 6.25 mmol), benzylamine (0.80 g, 7.5 mmol) and NaCN (0.03 g, 0.61 mmol) gave a residue which solidified on standing (18 h). The reaction mixture was triturated with EtOAc (20 mL). The white solid which remained was filtered and then further purified by recrystallization on from EtOAc.

Yield: 1.00 g (72%). R$_f$0.21 (5% MeOH/CHCl$_3$). mp 131°–133° C. (dec.).

$^1$H NMR (DMSO-d$_6$) δ1.83 (s, 3H), 2.35 (br s, 2H), 4.28 (d,J=4.4 Hz, 2H), 4.91 (d, J=7.0 Hz, 1H), 7.20–7.32 (m, 5H), 8.31 (br s, 1H), 8.51 (br s, 1H).

$^{13}$C NMR (DMSO-d$_6$) 22.66, 42.05, 60.29, 126.67, 127.10 (2C), 128.18 (2C), 139.23, 169.24, 170.67 ppm.

IR (KBr) 3300, 1650 (br),1530 (br), 1450, 740 cm$^{-1}$.

Mass spectrum, m/e (relative intensity) 222 (M$^+$+1, 100), 221 (M$^+$, 29), 133 (8).

Elemental analysis Calculated for C$_{11}$H$_{15}$N$_3$O$_2$ 59.71% C; 6.83% H; 18.99% N. Found 59.86%C; 6.88% H; 18.72% N.

EXAMPLE 50

Synthesis of 2-Acetamido-N-benzyl-2-(methylamino)acetamide

Ethyl 2-acetamido-2-(methylamino)acetate (1.50 g, 8.63 mmol), benzylamine (1.11 g, 10.35 mmol) and NaCN (0.04 g, 0.82 mmol) gave a brown residue which was purified by flash column chromatography on SiO$_2$ gel (2% MeOH/CHCl$_3$) to yield the desired product.

Yield: 1.00 g (49%). R$_f$0.33 (3% MeOH/CHCl$_3$). mp 115°–117° C. (recrystallized from ethyl acetate/petroleum ether).

$^1$H NMR (DMSO-d$_6$) δ1.87 (s, 3H), 2.18 (s, 3H), 4.20–4.29 (m, 2H), 4.87 (d,J=7.9 Hz, 1H), 7.24–7.35 (m, 5H), 8.14 (d,J=7.9 Hz, 1H), 8.55 (br s, 1H). The remaining amino proton was not detected.

$^{13}$C NMR (DMSO-d$_6$) 22.52, 31.37, 42.04, 65.99, 126.68, 127.12 (2C), 128.18 (2C), 139.28, 169.51, 169.83 ppm.

IR (KBr) 3240, 1610 (br), 1500 (br), 1430, 725,670 cm$^{-1}$.

Elemental analysis Calculated for C$_{12}$H$_{17}$N$_3$O$_2$ 61.26% C; 7.28% H; 17.86% N. Found 61.12% C; 7.01% H; 17.71% N.

EXAMPLE 61

Synthesis of 2-Acetamido-N-benzyl-2-(ethylamino)acetamide

Using ethyl 2-acetamido-2-(ethylamino)acetate (0.90 g, 4.79 mmol), benzylamine (0.62 g, 5.75 mmol), and NaCN (0.03 g, 0.51 mmol) gave an oily residue which was purified by flash column chromatography on SiO$_2$ gel (3% MeOH/CHCl$_3$) to give the desired product as a white solid.

Yield: 0.35 g (29%). R$_f$0.34 (4% MeOH/CHCl$_3$). mp 123°–125° C. (recrystallized from ethyl acetate/hexane).

$^1$H NMR (DMSO-d$_6$) δ0.93 (t,J=6.8 Hz, 3H), 1.81 (s, 3H), 2.08 (br s, 1H), 2.40–2.48 (m, 2H), 4.22 (d,J=5.5 Hz, 2H), 4.90 (d,J=7.8 Hz, 1H), 7.20–7.27 (m, 5H), 8.08 (d,J=7.8 Hz, 1H), 8.48 (t,J=5.5 Hz, 1H).

$^{13}$C NMR (CDCl$_3$) 15.14, 22.97, 37.65, 43.53, 65.68, 127.44 (2C), 127.50, 128.64 (2C), 137.73, 169.75, 171.20 ppm.

IR (KBr) 3250, 1620 (br), 1510 (br), 1450 (br), 740, 680 cm$^{-1}$.

Elemental analysis Calculated for C$_{13}$H$_{19}$N$_3$O$_2$ 62.63% C; 7.68% H; 16.85% N. Found 62.69% C; 7.49% H; 16.65% N.

EXAMPLE 52

Synthesis of 2-Acetamido-N-benzyl-2-(N-anilino)acetamide

Employing ethyl 2-acetamido-2-(N-anilino)acetate (2.00 g, 8.47 mmol), benzylamine (1.09 g, 10.00 mmol), and NaCN (0.04 g, 0.84 mmol) gave a white solid which separated during the course of the reaction. The precipitate was filtered and purified by recrystallization from absolute EtOH to give the desired product.

Yield: 1.10 g (44 %). mp 183°–185° C.

$^1$H NMR (DMSO-d$_6$) δ1.84 (s, 3H), 4.31 (d,J=5.8 Hz, 2H), 5.67 (t,J=8.1 Hz, 1H), 6.04 (d,J=8.1 Hz, 1H), 6.59–6.64 (m, 1H), 6.70–6.72 (m, 2H), 7.06–7.11 (m, 2H), 7.20–7.33 (m, 5H), 8.41 (d,J=8.1 Hz, 1H), 8.72 (t,J=5.8 Hz, 1H).

$^{13}$C NMR (DMSO-d$_6$) 22.46, 42.25, 60.42, 113.21 (2C), 117.22, 126.72, 127.16 (2C), 128.18 (2C), 128.77 (2C), 138.99. 145.88, 168.65, 169.70 ppm.

IR (KBr)3270, 1630, 1520, 1490, 1430, 740, 690 cm$^{-1}$.

Mass spectrum, m/e (relative intensity) 297 (M$^+$, 2), 239 (7), 164 (28), 163 (100) (20), 121 (100), 106 (47), 104 (65), 93 (63), 91 (77).

Elemental analysis Calculated for C$_{17}$H$_{19}$N$_3$O$_2$ 68.67% C; 6.44% H; 14.13% N. Found 68.94% C; 6.42% H; 13.92% N.

EXAMPLE 53

Synthesis of 2-Acetamido-N-benzyl-2-(N-(3-pyrazolylamino))acetamide

A solution of ethyl 2-acetamido-2-(N-(3-pyrazolylamino))acetate (1.60 g, 7.1 mmol) in MeOH (40 mL) containing benzylamine (0.83 g, 7.8 mmol) and NaCN (50 mg, 1 mmol) was stirred at 45°–55° C. (18 h). TLC analysis (8% MeOH/CHCl$_3$) of the reaction mixture indicated the presence of only a minor amount of product. A second lot of NaCN (50 mg, 1 mmol) was then added and the reaction was allowed to proceed at 45°–55° C. (6 h) and then at room temperature (48 h). The solvent was removed in vacuo and the residue was triturated with EtOAc (15 mL). The insoluble solid that remained was filtered and purified by flash column chromatography on SiO$_2$ gel (798 MeOH/CHCl$_3$) to give the desired product.

Yield: 0.90 g (44%). R$_f$0.35 (8% MeOH/CHCl$_3$). mp 135°–137° C.

$^1$H NMR (DMSO-d$_6$) δ1.82 (s, 3H) 4.29 (d,J=5.9 Hz, 2H) 5.51–5.55 (m, 3H), 7.18–7.40 (m, 6H), 8.36 (br s, 1H), 8.53 (br s, 1H), 11.66 (br s, 1H).

$^{13}$C NMR (DMSO-d$_6$) 22.59, 42.29, 61.79, 90.68, 126.67, 127.07 (2C), 128.17 (2C), 129.10, 139.41, 153.53, 169.19, 169.67 ppm.

IR (KBr) 3230 (br), 1620 (br), 1500 (br), 1430, 730, 690 cm$^{-1}$.

Mass spectrum, m/e (relative intensity) 288 (M$^+$+1, 64), 287 (M$^+$,2), 230 (28), 229 (100), 153 (46).

Elemental analysis Calculated for C$_{14}$H$_{17}$N$_5$O$_2$.0.5 H$_2$O 56.47% C; 6.12% It; 23.63% N. Found 56.63% C; 5.79% H; 23.43% N.

Preparation of Functionalized α-Heteroatom Substituted Amino Acid General Procedure A BBr$_3$ solution (1M in CH$_2$Cl$_2$, 1.1 equiv) was added to a solution of 2-acetamido-N-benzyl-2-ethoxyacetamide (1 equiv) in CH$_2$Cl$_2$ (10 mmol/125 mL). The mixture was stirred at room temperature (5 h) and then concentrated to dryness in vacuo to give 2-acetamido-N-benzyl-2-bromoacetamide as a pale yellow crystalline material. The bromo adduct was then dissolved in THF (10 mmol/250 mL), cooled (−78° C.), and then added over a 15 min interval to a cooled (−78° C.) solution of the heteroatom nucleophile in THF (1 mmol/1 mL). The reaction mixture was stirred at this temperature (30 min) and then at room temperature (90 min). The insoluble salts were filtered and the filtrate concentrated in vacuo. The residue was then purified by flash column chromatography on SiO$_2$ gel using the indicated solvent as the eluent.

Using this procedure the following examples were prepared.

EXAMPLE 54

Synthesis of 2-Acetamido-N-benzyl-2-(N,N-dimethylamino)acetamide

By making use of 2-acetamido-N-benzyl-2-ethoxyacetamide (3.00 g, 12.0 mmol), BBr$_3$ (1M in CH$_2$Cl$_2$, 13.2 mL, 13.2 mmol), and Me$_2$NH (5–6 equiv) was obtained a brown residue which was purified by flash column chromatography on SiO$_2$ gel (2.5% MeOH/CHCl$_3$) to give the desired product. The product was recrystallized from ethyl acetate/hexane to give light yellow cubic crystals.

Yield: 1.20 g (40%). R$_f$0.39 (5% MeOH/CHCl$_3$). mp 104°–106° C.

$^1$H NMR (DMSO-d$_6$) δ1.91 (s, 3H), 2.11 (s, 6H), 4.22 (dd,J=5.2, 14.7 Hz, 1H), 4.34 (dd,J=6.1, 14.7 Hz, 1H), 5.11 (d,J=8.3 Hz, 1H), 7.23–7.31 (m, 5H), 8.18 (d, J=8.3 Hz, 1H), 8.55 (br s, 1H).

$^{13}$C NMR (DMSO-d$_6$) 22.43, 40.33 (2C), 42.28, 69.42, 126.73, 127.27 (2C), 128.21(2C), 139.49, 168.49, 170.31 ppm.

IR (KBr) 3280, 1670 (br), 1500 (br), 1460, 760,700 cm$^{-1}$. Mass spectrum (FD) 250 (M$^+$+1).

Elemental analysis Calculated for C$_{13}$H$_{19}$N$_3$O$_2$ 62.63% C; 7.68% H; 16.85% N. Found 62.82% C; 7.66% H; 16.69% N.

EXAMPLE 55

Synthesis of 2-Acetamido-N-benzyl-2-(N-hydroxyamino)acetamide

Using 2-acetamido-N-benzyl-2-ethoxyacetamide (2.00 g, 8.0 mmol), BBr$_3$ (1M in CH$_2$Cl$_2$, 8.8 mL, 8.8 mmol), and anhydrous NH$_2$OH (5–6 equiv) gave an oily residue. The residue was separated in three components by flash chromatography on SiO$_2$ gel (7.5% MeOH/CHCl$_3$).

2-Acetamido-N-benzyl -2-(N-hydroxyamino)acetamide

Yield: 0.14 g (7%). R$_f$0.30 (8% MeOH/CHCl$_3$). mp 144–146° C. (dec.) (recrystallized from EtOH)

$^1$H NMR (DMSO-d$_6$) δ1.88 (s, 3H), 4.31 (d,J=5.7 Hz, 2H), 5.08 (dd,J=4.4, 8.1 Hz, 1 H), 5.94 (dd,J=2.8, 4.4 Hz, 1H) 7.19–7.35 (m, 5H), 7.52 (d,J=2.8 Hz, 1H), 8.26 (d,J=8.1 Hz, 1H), 8.42 (t,J=5.7 Hz, 1H).

$^{13}$C NMR (DMSO-d$_6$) 22.69, 42.25, 67.86, 126.69, 127.14 (2C), 128.18 (2C), 139.08, 168.53,169.67 ppm.

IR (KBr) 3320 (br), 1660 (br), 1540 (br), 1460, 750, 700 cm$^{-1}$.

Mass spectrum (FD) 238 (M$^+$+1).

Elemental analysis Calculated for C$_{11}$H$_{18}$N$_3$O$_3$ 55.69% C; 6.37% H; 17.71% N. Found 55.86% C; 6.37% H; 17.38% N.

Dimer A

Yield: 0.05 g (3%). R$_f$0.27 (8% MeOH/CHCl$_3$). mp 177°–179° C. (recrystallized from EtOH).

$^1$H NMR (DMSO-d$_6$) δ1.82 (s, 6H), 4.25–4.34 (m, 4H), 5.21 (d,J=9.3 Hz, 2H), 7.20–7.33 (m, 10H), 8.16 (d,J=9.3 Hz, 2H), 8.26 (t,J=5.8 Hz, 2H), 8.51 (s, 1H).

$^{13}$C NMR (DMSO-d$_6$) 22.54 (2C), 42.30 (2C), 67.55 (2C), 126.63 (2C), 127.13 (4C), 128.11 (4C), 139.02 (2C), 168.24 (2C), 169.33 (2C) ppm.

IR (KBr) 3240 (br), 1640 (br), 1510 (br), 1450, 690 cm$^{-1}$.

Mass spectrum (FD) 442 (M$^+$+1).

Elemental analysis Calculated for C$_{22}$H$_{27}$N$_5$O$_5$ 59.85% C; 6.16% H; 15.86% N. Found 59.5G% C; 6.08% H; 15.64% N.

Dimer B

Yield: 0.10 g (6%). R$_f$0.18 (8% MeOH/CHCl$_3$). mp 184°–186° C. (recrystallized from MeOH).

$^1$H NMR (DMSO-d$_6$) δ1.87 (6H), 4.20 (dd,J=5.3, 15.3 Hz, 2H), 4.44 (dd,J=6.2, 15.3 Hz, 2H), 5.28 (d,J=9.0 Hz, 2H), 7.15–7.31 (m, 10H), 8.00 (d,J=9.0 Hz, 2H), 8.39 (dd,J=5.3,6.2 Hz, 2H), 8.51 (s, 1H).

$^{13}$C NMR (DMSO-d$_6$) 22.50 (2C), 42.58 (2C), 69.98 (2C), 126.73 (2C), 127.23 (4C), 128.22 (4C), 139.08 (2C), 167.60 (2C), 169.57 (2C) ppm.

IR (KBr) 3300 (br), 1660 (br), 1530 (br), 1450, 740, 700 cm$^{-1}$.

Mass spectrum (FD) 442 (M$^+$+1)

Elemental analysis Calculated for C$_{22}$H$_{27}$N$_5$O$_5$59.85% C; 6.16% H; 15.86% N. Found 60.09% C; 5.93% H; 15.76% N.

EXAMPLE 56

Improved Synthesis of 2-Acetamido-N-benzyl-2-(N-hydroxyamino)acetamide

2-Acetamido-N-benzyl-2-bromoacetamide (prepared from 2-acetamido-N-benzyl-2-ethoxyacetamide (3.00 g, 12.0 mmol) and BBr$_3$ (1M in CH$_2$Cl$_2$, 17.2 mL, 17.2 rental)) was dissolved in THF (250 mL), cooled (−10° C.), and then added dropwise (30 min) to a suspension of NH$_2$OH (5–6 equiv) in THF (50 mL) at −10° C. The reaction mixture was stirred (30 min) at this temperature and then allowed to warm to room temperature (1 h). The insoluble materials were filtered and the filtrate was concentrated in vacuo. The residue was separated into two components by flash column chromatography on SiO$_2$ gel (7.5% MeOH/CHCl$_3$).

2-Acetamido-N-benzyl-2-(N-hydroxyamino)acetamide

Yield: 0.66 g (23%). mp 144°–146° C. (dec.) (recrystallized from EtOH).

Dimer B

Yield: 0.10 g (5%). mp 184°–186° C. (recrystallized from MeOH).

Dimer A was not observed under these conditions.

EXAMPLE 57

Synthesis of 2-Acetamido-N-benzyl-2-(N$^2$-phenylhydrazino)acetamide

Using 2-acetamido-N-benzyl-2-ethoxyacetamide (2.00 g, 8.0 mmol), BBr$_3$ (1M in CH$_2$Cl$_2$, 10.0 mL, 10.0 mmol), and phenylhydrazine (2.60 g, 24.0 mmol) gave a pale yellow oily residue which was purified by flash column chromatography on SiO$_2$ gel (2% MeOH/CHCl$_3$) to give the desired product. The product was recrystallized from chloroform/hexane as a light yellow solid.

Yield: 0.75 g (29%). R$_f$0.26 (2% MeOH/CHCl$_3$). mp 132°–134° C.

$^1$H NMR (DMSO-d$_6$) δ1.89 (s, 3H), 4.28 (d,J=5.8 Hz, 2H), 4.89 (d,J=5.2 Hz, 1H), 5.09 (dd,J=5.2, 7.4 Hz, 1H), 6.61 (t,J=7.4 Hz, 1H), 6.70–7.28 (m, 10H), 8.29 (d,J=7.4 Hz, 1H), 8.60 (t,J=5.8 Hz, 1H).

$^{13}$C NMR (DMSO-d$_6$) 22.88, 42.22, 66.22, 112.66 (2C), 117.57, 126.65, 127.08 (2C), 128.15 (2C), 128.53 (2C), 139.12, 149.90, 168.66, 170.04 ppm.

IR (KBr) 3300, 1640 (br), 1610, 1.520 (br), 1460, 760, 700 cm$^{-1}$.

Mass spectra (FD) 313 (M$^+$+1).

Elemental analysis Calculated for C$_{17}$H$_{20}$N$_4$O$_2$ 65.37% C; 6.45% H; 17.94% N. Found 65.15% C; 6.25% H; 17.71% N.

EXAMPLE 58

Synthesis of 2-Acetamido-N-benzyl-2-(N$^2$-benzyloxycarbonylhydrazino)acetamide Employing 2-acetamido-N-benzyl-2-ethoxyacetamide (3.00 g, 12.0 mmol), BBr$_3$ (1M in CH$_2$Cl$_2$, 15.0 mL, 15.0 mmol), and benzyl carbazate (4.58 g, 27.6 mmol), 0.95 g (21%) of the desired product was obtained. The product was recrystallized from chloroform/hexane to give a white amorphous solid. R$_f$ 0.32 (2% MeOH/CHCl$_3$) mp 152°–154° C.

$^1$H NMR (DMSO-d$_6$) δ1.85 (s, 3H), 4.27 (d,J=4.4 Hz, 2H), 5.00 (s, 2H), 5.14 (dd, J =3.1, 8.0 Hz, 1H), 5.23 (t,J=3.1 Hz, 1H), 7.25–7.35 (m, 10H), 8.26 (d,J=8.0 Hz, 1H), 8.56 (br s, 1H), 8.66 (br s, 1H).

$^{13}$C NMR (DMSO-d$_6$) 22.71, 42.23, 65.56, 65.97, 126.69, 127.16 (2C), 127.61 (2C), 127.77, 128.13 (2C), 128.27 (2C), 136.74, 138.87, 168.04, 169.95 ppm.

IR (KBr) 3325, 1620 (br), 1500 (br), 1440, 740,680 cm$^{-1}$

Mass spectrum (FD) 371 (M$^+$+1).

Elemental analysis Calculated for $C_{19}H_{22}N_4O_4$ 61.61% C; 5.99% H; 15.13% N. Found 61.40% C; 6.21% H; 15.39% N.

EXAMPLE 59

Synthesis of 2-Acetamido-N-benzyl-2-phenoxyacetamide

Using 2-acetamido-N-benzyl-2-ethoxyacetamide (3.00 g, 12.0 mmol), $BBr_3$ (1M in $CH_2Cl_2$, 15.0 mL, 15.0 mmol), and NaOPh (4.18 g, 30 mmol) gave a brown oily residue which was purified by flash column chromatography on $SiO_2$ gel using first $CHCl_3$ and then 2% $MeOH/CHCl_3$ as the eluents to give the desired product. The compound was recrystallized from chloroform/hexane.

Yield: 0.80 g (22%).

$R_f$ 0.58 (3% $MeOH/CHCl_3$). mp 125°–128° C. (softens at 122° C.).

$^1H$ NMR (DMSO-$d_6$) δ1.83 (s, 3H), 4.35 (d,J=5.7 Hz, 2H), 6.18 (d,J=9.4 Hz, 1H), 6.94–6.99 (m, 2H), 7.02–7.33 (m, 8H), 8.98 (t,J=5.7 Hz, 1H), 9.10 (d,J=9.4 Hz, 1H).

$^{13}C$ NMR (DMSO-$d_6$) 22.54, 42.24, 76.44, 116.09 (2C), 121.78, 126.84, 127.26 (2C), 128.25 (2C), 128.44 (2C), 138.84, 155.97, 166.63, 170.73 ppm.

IR (KBr) 3300, 1650 (br), 1600, 1530 (br), 1490, 1450, 760, 700 cm$^{-1}$.

Mass spectrum (FD) 299 (M$^+$+1).

Elemental analysis Calculated for $C_{17}H_{18}N_2O_3$.0.5 $H_2O$ 66.43% C; 6.23% H; 9.11% Found 66.62% C; 6.23% H; 9.16% N.

EXAMPLE 60

Synthesis of 2-Acetamido-N-benzyl-2-(methylmercapto)acetamide

A cooled (−78° C.) solution of $Et_3N$ (4.85 g, 48.0 mmol) in THF (20 mL) was added to a cooled (−78° C.) solution of 2-acetamido-N-benzyl-2-bromoacetamide (prepared from 2-acetamido-N-benzyl-2-ethoxyacetamide (4.00 g, 16.0 mmol) and $BBr_3$ (1M in $CH_2Cl_2$, 20.0 mL, 20.0 mmol)) in THF (275 mL). A cooled (−78° C.) solution of excess MeSH (5–6 equiv) in THF (55 mL) was then added. The reaction mixture was stirred at this temperature (30 min) and then at room temperature (1 h). The insoluble materials were filtered and the filtrate was evaporated to dryness in vacuo. The oily residue obtained was purified by flash column chromatography on $SiO_2$ gel (2% $MeOH/CHCl_3$) to give 1.10 g (27%) of the desired product as a yellow orange oil. The product was purified by a second flash column chromatography on $SiO_2$ gel (2% $MeOH/CHCl_3$) to give 0.72 g of the pure product as a white solid.

$R_f$ 0.65 (3% $MeOH/CHCl_3$). mp 155°–157° C.

$^1H$ NMR (CD$_3$NO$_2$) δ1.98 (s, 3H), 2.08 (s, 3H), 4.39 (dd,J=6.1, 15.2 Hz, 1H), 4.49 (dd,J=6.1, 15.2 Hz, 1H), 5.51 (d,J=7.8 Hz, 1H), 7.15 (d,J=7.8 Hz, 1H), 7.17–7.41 (m, 6H).

$^{13}C$ NMR (CD$_3$NO$_2$) 12.28, 22.94, 44.26, 56.03, 128.46, 128.60 (2C), 129.77 (2C), 140.17, 169.19, 171.06 ppm.

IR (KBr) 3320, 1650 (br), 1520 (br), 1460, 750 cm$^{-1}$.

Mass spectrum (FD) 253 (M$^+$+1).

Elemental analysis Calculated for $C_{12}H_{16}N_2O_2S$ 57.12% C; 6.39% H; 11.10% N. Found 57.06% C; 6.57% H; 11.28% N.

EXAMPLE 61

Synthesis of 2-Acetamido-N-benzyl-2-(ethylmercapto)acetamide

Using the procedure described for the synthesis of 2-acetamido-N-benzyl-2-(methylmercapto)acetamide, 2-acetamido-N-benzyl-2-ethoxyacetamide (2.00 g, 8.0 mmol) and EtSH (0.65 g, 10.4 mmol) were converted to 0.80 g (38%) of the desired product. The compound was further purified by recrystallization from chloroform/hexane to give a beige solid. $R_f$ 0.60 (4% $MeOH/CHCl_3$). mp 146°–148° C.

$^1H$ NMR (DMSO-$d_6$) δ1.56 (t,J=7.4 Hz, 3H), 1.88 (s, 3H), 2.49–2.67 (m, 2H), 4.23 (dd,J=5.9, 15.2 Hz, 1H), 4.32 (dd,J=5.9, 15.2 Hz, 1H), 5.55 (d,J=9.1 Hz, 1H), 7.20–7.35 (m, 5H), 8.59 (d,J=9.1 Hz, 1H), 8.75 (t,J=5.9 Hz, 1H).

$^{13}C$ NMR (DMSO-$d_6$) 14.73, 22.43, 23.73, 42.10, 53.70, 126.87, 127.14 (2C), 128.32 (2C), 139.01, 167.89, 169.02 ppm.

IR (KBr) 3240, 1620 (br), 1510 (br), 1415, 680, 640 cm$^{-1}$.

Mass spectrum (FD) 267 (M$^+$+1).

Elemental analysis Calculated for $C_{13}H_{18}N_2O_2S$.0.25 $H_2O$ 57.65% C; 6.88% H; 10.34% N. Found 57.48% C; 6.84% H; 10.28% N.

Preparation of Functionalized α-Heteroatom Substituted Amino Acids, General Procedure A mixture of 2-acetamido-2-(N,N,N-trimethylammonium)acetamide tetrafluoroborate (1 eqiuv), and the nitrogen nucleophile (4–5 equiv) in MeOH (1 mmol/1 mL) was stirred at 55°–60° C. (3 h). The solvent was removed in vacuo and the residue was purified by flash column chromatography on $SiO_2$ gel using the indicated solvents as the eluent.

Using this procedure the following examples were prepared.

EXAMPLE 62

Synthesis of 2-Acetamido-N-benzyl-2-(N-methoxyamino)acetamide

Using a MeOH solution of MeONH$_2$ (prepared from MeONH$_2$.HCl (2.83 g, 33.9 mmol) and NaOMe (1.41 g, 26.1 mmol)), and 2-acetamido-2-(N,N,N-trimethylammonium)acetamide tetrafluoroborate (2.70 g, 7.67 mmol) gave an oily residue which was purified by flash column chromatography on $SiO_2$ gel (2% $MeOH/CHCl_3$) to give the desired product. The product was recrystallized from chloroform/hexane.

Yield: 0.80 g (42%). $R_f$ 0.23 (2% $MeOH/CHCl_3$) mp 95°–97° C.

$^1H$ NMR (DMSO-$d_6$) δ1.88 (s, 3H), 3.38 (s, 3H), 4.22–4.41 (m, 2H), 5.18 (dd,J=4.9, 7.8 Hz, 1H), 6.78 (d,J=4.9 Hz, 1H), 7.21–7.32 (m, 5H), 8.33 (d,J=7.8 Hz, 1H), 8.56 (br s, 1H).

$^{13}C$ NMR (DMSO-$d_6$) 22.64, 42.28, 61.42, 66.25, 126.74, 127.19 (2C), 128.19 (2C), 139.11, 167.95, 169.66 ppm.

IR (KBr) 3300, 1650, 1620, 1510 (br), 1440, 750, 680 cm$^{-1}$.

Mass spectrum (FD) 252 (M$^+$+1).

Elemental analysis Calculated for $C_{12}H_{17}N_3O_3$ 57.63% C; 6.82% H; 16.72% N. Found 57.06% C; 6.63% H; 16.65% N.

EXAMPLE 63

Synthesis of 2-Acetamido-N-benzyl-2-(N-(N-methylhydroxyamino))acetamide

An MeOH solution (30 mL) of MeNHOH (21.74 mmol) (prepared from MeNHOH.HCl (2.36 g, 28.26 mmol) and NaOMe (1.17 g, 21.74 mmol)) and 2-acetamido-2-(N,N,N-trimethylammonium)acetamide tetrafluoroborate (2.20 g, 6.25 mmol) gave a residue which was purified by flash column chromatography on $SiO_2$ gel (6% $MeOH/CHCl_3$) to give the desired product as a white solid. The product was then purified by recrystallization from EtOH.

Yield: 0.95 g (61%). $R_f$ 0.32 (8% $MeOH/CHCl_3$). mp 159°–161° C.

$^1H$ NMR (DMSO-$d_6$) δ1.95 (s, 3H), 2.43 (s, 3H), 4.26 (dd,J=5.7, 15.1 Hz, 1H), 4.35 (dd,J=5.7, 15.1 Hz, 1H), 5.09 (d,J=9.1 Hz, 1H), 7.21–7.29 (m, 5H), 8.05 (s, 1H), 8.18 (d,J=9.1 Hz, 1H), 8.23 (t,J=5.7 Hz, 1H).

$^{13}C$ NMR (DMSO-$d_6$) 22.40, 42.34, 43.92, 71.49, 126.62, 127.12 (2C), 128.12 (2C), 139.14, 167.82, 170.28 ppm.

IR (KBr) 3440 (br), 3300, 1640, 1530, 1460, 750, 700 $cm^{-1}$.

Mass spectrum (FD) 252 (M++1).

Elemental analysis Calculated for $C_{12}H_{17}N_3O_3$ 57.36% C; 6.82% H; 16.72% N. Found 57.65% C; 6.59% H; 16.66% N.

EXAMPLE 64

Synthesis of 2-Acetamido-N-benzyl-2-(N-(N,O-dimethylhydroxyamino))acetamide

An MeOH solution (20 mmol) of MeNHOMe (17.39 mmol) (prepared from MeNHOMe.HCl (2.20 g, 23.02 mmol) and NaOMe (0.94 g, 17.39 mmol)) and 2-acetamido-2-(N,N,N-trimethylammonium)acetamide tetrafluoroborate (2.10 g, 5.97 mmol) gave a solid residue. Flash column chromatography of the solid on $SiO_2$ gel (2% $MeOH/CHCl_3$) yielded pure desired product. The product was recrystallized from EtOH.

Yield: 1.30 g (82%). $R_f$ 0.39 (2% $MeOH/CHCl_3$). mp 165°–167° C.

$^1H$ NMR (DMSO-$d_6$) δ1.93 (s, 3H), 2.43 (s, 3H), 3.32 (s, 3 H), 4.25 (dd,J=5.9, 14.9 Hz, 1H), 4.37 (dd,J=5.9, 14.9 Hz, 1H), 5.19 (d,J=9.4 Hz, 1H), 7.21–7.35 (m, 5 H), 8.31 (d,J=9.4 Hz, 1H), 8.56 (t,J=5.9 Hz, 1H).

$^{13}C$ NMR (DMSO-$d_6$) 22.36, 39.68, 42.34, 59.16, 70.33, 126.74, 127.41 (2C), 128.21 (2C), 139.30, 167.38, 170.30 ppm.

IR (KBr) 3300, 1640 (br), 1540 (br), 1460, 750, 700 $cm^{-1}$.

Mass spectrum (FD) 266 (M++1).

Elemental analysis Calculated for $C_{13}H_{19}N_3O_3$ 58.85% C; 7.22% H; 15.84% N. Found 59.05% C; 7.37% H; 15.75% N.

EXAMPLE 65

Synthesis of 2-Acetamido-N-benzyl-2-(N-isoxazolidino)acetamide

Using 2-acetamido-2-(N,N,N-trimethylammonium)acetamide tetrafluoroborate (1.60 g, 4.55 mmol), isoxazolidine (prepared from isoxazolidine hydrobromide (2.41 g, 15.65 mmol) and NaOMe (0.70 g, 13.04 mmol)) gave the desired product. The product was recrystallized from chloroform/hexane to give a white amorphous solid.

Yield: 0.80 g (64%). $R_f$ 0.29 (4% $MeOH/CHCl_3$). mp 149°–151° C.

$^1H$ NMR (DMSO-$d_6$) δ1.91 (s, 3H), 2.05–2.20 (m, 2H), 2.45–2.89 (m, 1H), 2.98–3.07 (m, 1H), 3.74–3.90 (m, 2H), 4.25 (dd,J=6.1, 15.3 Hz, 1H), 4.35 (dd,J=6.1, 15.3 Hz, 1H), 5.23 (d,J=9.2 Hz, 1H), 7.15–7.35 (m, 5H), 8.49 (d,J=9.2 Hz, 1H), 8.56 (br s, 1 H).

$^{13}C$ NMR (DMSO-$d_6$) 22.26, 28.26, 42.15, 18.9,1, 66.19, 68.77, 126.64, 127.02 (2C), 128.13 (2C), 139.22, 167.43, 170.27 ppm.

IR (KBr) 3400 (br), 3300, 1650, 1530, 1470. 740,700,610 $cm^{-1}$.

Mass spectrum (FD) 278 (M++1).

Elemental analysis Calculated for $C_{14}H_{19}N_3O_3$ 60.64% C; 6.91% H; 15.15% N. Found 60.16% C; 7.04% H; 15.07% N.

Preparation of Functionalized α-Heteroatom Substituted Amino Acids. General Procedure 2-Acetamido-N-benzyl-2-ethoxyacetamide (1 equiv) was suspended in $Et_2O$ (100 mL/10 mmol), and then $BF_3.Et_2O$ (1.6–2.4 equiv) was rapidly added and the resulting solution was stirred (10 min). The nucleophile ($H_2O$ or EtSH) (1.6–4.0 equiv) was then added and the reaction was stirred at room temperature (18–48 h). The reaction was then quenched by the addition of an aqueous $NaHCO_3$ (100 mL/10 mmol)/ice mixture. The experimental workup varied slightly for each compound and is described in the following examples along with the observed spectral properties.

EXAMPLE 66

Synthesis of 2-Acetamido-N-benzyl-2-hydroxyacetamido

Reacting 2-acetamido-N-benzyl-2-ethoxyacetamide (1.00 g, 4.0 mmol), $BF_3.Et_2O$ (0.91 g, 6.4 mmol) and $H_2O$ (0.12 g, 6.7 mmol) followed by aqueous $NaHCO_3$ workup gave an aqueous reaction mixture. The solution was then extracted with EtOAc (3×50 mL), and the combined EtOAc extracts were dried ($Na_2SO_4$), and concentrated in vacuo. The residue was purified by flash column chromatography on $SiO_2$ gel (3% $MeOH/CHCl_3$) to give the desired product as a white solid.

Yield: 0.30 g (34%). $R_f$ 0.14 (3% $MeOH/CHCl_3$). mp 136°–138° C.

$^1H$ NMR(DMSO-$d_6$) δ1.85 (s, 3H), 4.29 (d,J=5.9 Hz, 2H), 5.48 (dd,J=5.5, 8.6 Hz, 1H), 6.47 (d,J=5.5 Hz, 1H), 7.21–7.35 (m, 5H), 8.52 (t,J=5.9 Hz, 1H), 8.59 (d,J=8.6 Hz, 1H).

$^{13}C$ NMR (DMSO-$d_6$) 22.66, 41.99, 71.42, 126.66, 127.22 (2C), 128.13 (2C), 139.20, 169.47, 169.62 ppm.

IR (KBr) 3300, 1620, 1530 (br), 1430 (br), 730,690 $cm^{-1}$.

Mass spectrum, m/e (relative intensity) 223 (M++1, 1), 163 (11), 134 (9), 106 (46), 91 (100), 77 (22), 65 (38).

Elemental analysis Calculated for $C_{11}H_{14}N_2O_3$ 59.45%. C; 6.35% H; 12.61% N. Found 59.2,1% C; 6.36% H; 12.50% N.

EXAMPLE 62 synthesis of 2-Acetamido-N-benzyl-2-(ethylmercapto)acetamide

Using 2-acetamido-N-benzyl-2-ethoxyacetamide (2.00 g, 8.0 mmol), $BF_3.Et_2O$ (2.72 g, 19.2 mmol) and EtSH (2.38 g, 38.4 mmol) gave an aqueous reaction mixture. The solution was extracted with CHCl₃ (3×100 mL). The combined CHCl₃ layers were dried (Na₂SO₄), and then concentrated in vacuo to give the desired product as white solid.

Yield: 1.90 g (89%). $R_f$ 0.60 (4% MeOH/CHCl₃). mp 148°–149° C. (mixed melting point with an authentic staple of Example 61 was undepressed).

EXAMPLE 68

Synthesis of 2,2-Diacetamido-N-benzylacetamide

Ac₂O (1 mL) was added to a solution of 2-acetamido-N-benzyl-2-aminoacetamide (1.10 g, 4.98 mmol) in dry pyridine (10 mL) and then CH₂Cl₂ (20 mL) was added. The mixture was stirred at room temperature (4 h) and then the volatile materials were removed in vacuo. The residue was then treated with a saturated aqueous NaHCO₃ solution (50 mL). The white solid that remained was the desired product and was filtered, dried (Na₂SO₄), and recrystallized from MeOH.

Yield: 1.20 g (92%). mp 265°–267° C. (dec.).

$^1$H NMR (DMSO-d₆) δ1.84 (s, 6H), 4.26 (d,J=5.8 Hz, 2H), 5.71 (t,J=7.6 Hz, 1H), 7.20–7.31 (m, 5H), 8.44 (d,J=7.6 Hz, 2H), 8.48 (t,J=5.8 Hz, 1H).

$^{13}$C (DMSO-d₆) 22.44 (2C), 42.26, 56.99, 126.62, 127.02 (2C), 128.12 (2C), 139.15, 168.19, 169.39 (2C) ppm.

IR (KBr) 3260, 1530, 1500, 740, 690 cm$^{-1}$.

Mass spectrum (FD) 264 (M⁺+1).

Elemental analysis Calculated for C₁₃H₁₇N₃O₃ 59.30% C; 6.51%H; 15.96% N. Found 59.16% C; 6.49%H; 15.86% N.

EXAMPLE 69

Synthesis of 2-Acetamido-N-benzyl-2-trifluoroacetamidoacetamide

Ice cold trifluoroacetic anhydride (8 mL) was added in one portion to ice cold 2-acetamido-N-benzyl-2-aminoacetamide (1.00 g, 4.53 mmol). The reaction was accompanied by the evolution of heat. After stirring (5 min), the volatile materials were removed in vacuo. The residue was treated with a saturated aqueous NaHCO₃ solution (20 mL), and the solid that remained was filtered and washed with H₂O to give the desired product. The product was recrystallized from EtOH.

Yield: 1.00 g (70%). $R_f$ 0.34 (8% MeOH/CHCl₃). mp 228°–230° C.

$^1$H NMR (DMSO-d₆) δ1.90 (s,3H), 4.30 (d,J=5.1 Hz, 2H), 5.85 (d,J=8.0 Hz, 1 H), 7.21–7.35 (m, 5H), 8.64 (d,J=8.0 Hz, 1H), 8.75 (t,J=5.1 Hz, 1H), 10.04 (s, 1H).

$^{13}$C NMR (DMSO-d₆) 22.52, 42.52, 57.42, 117.4 (q,JCF=288.3 Hz), 126.80, 127.16 (2C), 128.21 (2C), 138.93, 156.14 (q,JCF=35.3 Hz), 166.39, 169.88 ppm.

IR (KBr) 3300, 1720, 1660, 1520, 1380, 760,700 cm$^{-1}$.

Mass spectrum (FD) 318 (M⁺+1).

Elemental analysis Calculated for C₁₃H₁₄N₃O₃F₃ 49.21% C; 4.45% H; 13.24% N. Found 49.48% C; 4.43% H; 13.10% N.

EXAMPLE 70

Synthesis of 2-Acetamido-N-benzyl-2-(N,N,N-trimethylammonium)acetamide Tetrafluoroborate A solution of 2-acetamido-N-benzyl-2-(N,N-dimethylamino)acetamide (1.93 g, 7.76 mmol) in nitromethane (7 mL) was added slowly to an ice cold solution of trimethyloxonium tetrafluoroborate (1.26 g, 8.54 mmol) in nitromethane (6 mL). The reaction mixture was stirred at this temperature (15 min) and then at room temperature (2 h). Anhydrous Et₂O (~50 mL) was added to the reaction mixture and the white solid that separated was filtered, washed with Et₂O, and dried in vacuo.

Yield: 1.95 g (72%). mp 171°–173° C. (dec.).

$^1$H NMR (CD₃NO₂) δ2.14 (s, 3H), 3.18 (s, 9H), 4.50 (d,J=5.8 Hz, 2 H), 5.70 (d,J=9.3 Hz, 1H), 7.30–7.41 (m, 5H), 7.57 (d,J=9.3 Hz, 1H), 7.70 (br s, 1H).

IR (KBr) 3300, 1680 (br), 1530, 1490, 710 cm$^{-1}$.

Mass spectrum (FD) 264 (M+).

Elemental analysis Calculated for C₁₄H₂₂N₃O₂BF₄ 47.89% C; 6.31%H; 11.97% N. Found 47.80% C; 6.33% H; 12.00% N.

EXAMPLE 71

Synthesis of 2-Acetamido-N-benzyl-2-(ethylmercapto)acetamide-S-oxide

A solution of m-chloroperbenzoic acid (1.00 g (~65%), 3.76 mmol) in CH₂Cl₂ (10 mL) was added dropwise into a stirred, cooled (−10° to −15° C.) CH₂Cl₂ solution (125 mL) of 2-acetamido-N-benzyl-2-(ethylmercapto)acetamide (1.00 g, 3.76 mmol) under N₂. The reaction was stirred (30 min) at this temperature and then the m-chlorobenzoic acid was precipitated as its ammonium salt by passing NH₃ gas over the surface of the reaction solution. The excess NH₃ was removed by passing N₂ gas through the solution (20 min) at room temperature. The ammonium salt was filtered, and the filtrate was concentrated in vacuo. The residue was purified by flash chromatography on SiO₂ gel (2% MeOH/CHCl₃) to give the desired product. The product was recrystallized from chloroform/hexane as a white granular solid.

Yield: 0.55 g (52%). $R_f$ 0.23 (2% MeOH/CHCl₃). mp 135°–137° C.

$^1$H NMR (DMSO-d₆) δ1.15 (t,J=7.5 Hz, 3H), 1.99 (s, 3H), 2.49–2.56 (m, 1H), 2.65–2.72 (m, 1H), 4.34 (d,J=5.7 Hz, 2H), 5.55 (d,J=9.5 Hz, 1H), 7.23–7.34 (m, 5H), 8.74 (d,J=9.5 Hz, 1H), 8.77 (t,J=5.7 Hz, 1H).

$^{13}$C NMR (DMSO-d₆) 7.03, 22.34, 42.40, 42.47, 67.15, 126.89, 127.27 (2C), 128.24 (2C), 138.55, 164.66, 170.18 ppm.

IR (KBr) 3300 (br), 1640 (br), 1510 (br), 1370, 1230, 1100, 1020, 900 cm$^{-1}$.

Mass spectrum (FD) 283 (M⁺+1).

Elemental analysis Calculated for C₁₃H₁₈N₂O₃S 55.30% C; 6.43% H; 9.92% N. Found 55.17% C; 6.38% H; 9.70% N.

EXAMPLE 72

Synthesis of 2-Acetamido-N-benzyl-2-(S-ethylmercapto)acetamide-S-oxide

A solution of NaIO₄ (1.77 g, 8.27 mmol) in H₂O (20 mL) was added dropwise into a stirred solution of 2-acetamido-N-benzyl-2-(ethylmercapto)acetamide (2.00 g, 7.52 mmol) in MeOH (25 mL). A precipitate appeared rapidly. H₂O (~30 mL) was added to the mixture to dissolve most of the suspension, and the reaction was stirred (4 h) at room temperature. The reaction was concentrated in vacuo and the remaining aqueous mixture was extracted with CHCl₃ (3×100 mL). The combined CHCl₃ extracts were dried (Na₂SO₄) and the solvent was removed in vacuo. The oily residue (1.95 g, 92%) solidified on drying in vacuo. NMR analysis (DMSO-$d_6$) of the product showed that it was a 2:1 mixture of the two diastereomers of the desired product. The reaction was recrystallized from EtOAc to give nearly pure diastereomer A (1.20 g) that was obtained from the m-chloroperbenzoic acid reaction. The EtOAc mother liquor was concentrated and the remaining residue (0.75 g) was recrystallized from ethyl acetate/hexane to give a diastereomeric mixture (0.41 g) of the two diastereomers A and B in a 2:3 ratio, respectively.

$R_f$ 0.60 (4% MeOH/CHCl$_3$). mp 135°–137° C. (softens at 117° C.).

IR (KBr) 3300 (br), 1640 (br), 1510 (br), 1370, 1230, 1100, 1020, 900 cm$^{-1}$.

Mass spectrum (FD) 283 (M++I).

Elemental analysis: Calculated for $C_{13}H_{18}N_2O_3S$: 55.30% C; 6.43% H; 9.92% N. Found: 55.58% C; 6.49% H; 9.97% N.

The following NMR spectral properties have been assigned to compounds A and B.

Diastereomer A $^1$H NMR (DMSO-$d_6$) δ1.16 (t,J=7.5 Hz, 3H), 2.00 (s, 3H), 2.49–2.72 (m, 2 H), 4.28–4.39 (m, 2H), 5.56 (d,J=9.7 Hz, 1H), 7.21–7.34 (m, 5H), 8.71–8.77 (m, 2H).

$^{13}$C NMR (DMSO-$d_6$) 7.10, 22.43, 42.48, 42.57, 67.23, 126.98, 127.36 (2C), 128.33 (2C), 138.63, 164.73, 170.25 ppm.

Diastereomer B $^1$H NMR (DMSO-$d_6$) δ1.13 (t,J=7.6 Hz, 3H), 1.94 (s, 3H), 2.49–2.72 (m, 2H), 4.28–4.39 (m, 2H), 5.71 (d,J=9.9 Hz, 1H), 7.21–7.34 (m, 5H), 8.83 (d,J=9.9 Hz, 1H), 8.98 (t,J=5.6 Hz, 1H).

$^{13}$C NMR (DMSO-$d_6$) 6.47, 22.43, 41.53, 42.55, 67.90, 126.98, 127.36 (2C), 128.33 (2C), 138.39, 164.43, 169.82 ppm.

EXAMPLE 73

Synthesis of 2-Acetamido-N-benzyl-2-(ethanesulfonyl)acetamide

An aqueous solution (20 mL) of NaIO$_4$ (3.00 g, 14.02 mmol) was added to a MeOH solution (20 mL) of 2-acetamido-N-benzyl-2-(ethylmercapto)acetamide (0.95 g, 3.57 mmol). The initial homogeneous solution rapidly became turbid. H$_2$O (~10 mL) was then added dropwise until the system became homogeneous. The solution was stirred (18 h) at 50°–60° C. MeOH (50 mL) was added to the reaction solution and the precipitated salt was filtered and washed with MeOH (10 mL). The filtrate was concentrated and the remaining solution was extracted with CHCl$_3$ (3×50 mL). The combined CHCl$_3$ extracts were dried (Na$_2$SO$_4$), and concentrated in vacuo. The residue was purified by flash chromatography on SiO$_2$ gel (1% MeOH/CHCl$_3$) to give the desired product. The product was further purified by recrystallization from EtOH:.

Yield: 0.34 g (32%). $R_f$ 0.34 (3% MeOH/CHCl$_3$). mp 161°–163° C.

$^1$H NMR (DMSO-$d_6$) δ1.22 (t,J=7.4 Hz, 3H), 1.99 (s, 3H), 3.04–3.24 (m, 2 H), 4.31 (dd,J=5.7, 15.3 Hz, 1H), 4.41 (dd,J=5.7, 15.3 Hz, 1H), 5.93 (d,J=9.8 Hz, 1H), 7.22–7.35 (m, 5H), 9.13 (t,J=5.7 Hz, 1H), 9.17 (d,J=9.8 Hz, 1H).

$^{13}$C NMR (DMSO-$d_6$) 5.72, 22.27, 42.63, 45.,t3, 69.14, 127.02, 127.28 (2C), 128.33 (2C), 138.16, 161.88, 169.83 ppm.

IR (KBr) 3300, 2940, 1660, 1520, 1310, 1230, 1120, 900 cm$^{-1}$.

Mass spectrum (FD) 298 (M+).

Elemental analysis Calculated for $C_{13}H_{18}N_2O_4S$ 52.33% C; 6.08% H; 9.39% N. Found 52.52% C; 6.06% H; 9.53% N.

EXAMPLE 74

Synthesis of 2-Acetamido-N-benzyl-2-(N,N,N-trimethylammonium)acetamide Tetrafluoroborate A solution of 2-acetamido-N-benzyl-2-(N,N-dimethylamino)acetamide (1.93 g, 7.76 mmol) in nitromethane (7 mL) was added slowly to an ice cold solution of trimethyloxonium tetrafluoroborate (1.26 g, 8.54 mmol) in nitromethane (6 ml,). The reaction mixture was stirred at this temperature (15 min) and then at room temperature (2 h). Anhydrous Et$_2$O (−50 mL) was added to the reaction mixture and the white solid that separated was filtered, washed with Et$_2$O, and dried in vacuo.

Yield: 1.95 g (72%). mp 171°–173° C. (dec.).

$^1$H NMR (CD$_3$NO$_2$) δ2.14 (s, 3H), 3.18 (s, 9H), 4.50 (d,J=5.8 Hz, 2H), 5.70 (d,J=9.3 Hz, 1H), 7.30–7.41 (m, 5H), 7.57 (d,J=9.3 Hz, 1H), 7.70 (br s, 1H).

IR (KBr) 3300, 1680 (br), 1530, 1490, 710 cm$^{-1}$.

Mass spectrum (FD) 264 (M+).

Elemental analysis Calculated for $C_{14}H_{22}N_3O_2BF_4$ 47.89% C; 6.31% H; 11.97% N. Found 47.80% C; 6.33% H; 12.00% N.

EXAMPLE 75

Synthesis of 2-Acetamido-N-benzyl-2-(1-pyrrole)acetamide. A solution of 2-acetamido-N-benzyl-2-bromoacetamide (prepared from 2-acetamido-N-benzyl-2ethoxyacetamide (2.00 g, 8.0 mmol) and BBr$_3$ (1 M CH$_2$Cl$_2$ solution, 8.8 mL, 8.8 mmol)) was prepared in THF (225 mL) and cooled to −78° C. It was then added under N$_2$ gas atmosphere to a cooled (−78° C.) suspension of potassium pyrrole (2.71 g, 25.8 mmol) in THF (25 mL). The reaction mixture was stirred at −78° C. (1 h) and then at room temperature (1 h). It was then treated with water (10 mL) and acidified with 5% citric acid to pH 4.0 after which it was made basic with aqueous saturated Na$_2$CO$_3$ solution. The aqueous mixture was extracted with EtOAc (2×250 mL) and the organic layers were dried (Na$_2$SO$_4$). The volatile materials were removed in vacuo and the residue was purified by flash column chromatography on silica gel using 3% MeOH/CHCl$_3$ as the eluant to give 0.4 g (18%) of the desired product. It was purified by recrystallization from EtOH: mp 182°–184° C.; $R_f$ 0.44 (4% MeOH/CHCl$_3$); $^1$H NMR (DMSO-$d_6$) δ1.91 (s, COCH$_3$), 4.30 (d,J=5.5 Hz, CH$_2$), 6.01 (s,2×C$_3$H), 6.38 (d,J=8.7 Hz, CH), 6.85 (s, 2×C$_2$H), 7.11–7.35 (m, 5PhH), 8.96 (t,J=5.5 Hz, NH), 9.14 (d,J=8.7 Hz, NH); $^{13}$C NMR (DMSO-$d_6$) 22.22 (COCH$_3$), 42.15 (CH$_2$), 62.86 (CH), 107.79 (2C$_3$), 119.19 (2C$_2$), 126.76 (C$_{4'}$), 127.01 (2C$_2$, or 2C$_{3'}$), 128.11 (2C$_{2'}$ or 2C$_{3'}$), 138.34 (C$_{1'}$), 166.37 (CONH), 169.41 (COCH$_3$) ppm; mass spectrum, m/e (relative intensity) 272 (M++1, 22), 271 (M+, 100).

Anal. Calcd for $C_{15}H_{17}N_3O_2.0.2$ H$_2$O: C, 65.53; H, 6.37; N, 15.28. Found: C, 65.80; H, 6.22; N, 15.13.

EXAMPLE 76

Synthesis of 2-Acetamido-N-benzyl-2-(1-imidazole)acetamide. Making use of the experimental procedure described in the preceding experiment, 2-acetamido-N-benzyl-2-ethoxyacetamide (2.00 g, 8.0 mmol), BBr$_3$ (1M CH$_2$Cl$_2$ solution, 8.8 mL, 8.8 mmol), Et$_3$N (1.62 g, 1.60 mmol), and imidazole (0.60 g, 8.8 mmol) gave 0.60 g (30%) of the desired product. It was recrystallized from ethyl acetate/hexane as a beige colored solid: mp 146°–148° C.; R$_f$0. (7% MeOH/CHCl$_3$); $^1$H NMR (DMSO-d$_6$) δ1.85 (s, COCH$_3$), 4.30 (br s, CH$_2$), 6.53 (d,J=8.0 Hz, CH), 6.89 (s, C$_5$H), 7.12–7.33 (m, C$_4$H, 5PhH), 7.69 (s, C$_2$H), 9.06 (br s, NH), 9.29 (d,J=8.0 Hz, NH); $^{13}$C NMR (DMSO-d$_6$) 22.28 (COCH$_3$), 42.36 (CH$_2$), 61.18 (CH), 117.56 (C$_5$), 126.92 (C$_{4'}$), 127.16 (2C$_{2'}$ or 2C$_{3'}$), 128.19 (C$_4$), 128.26 (2C$_{2'}$ or 2C$_{3'}$), 136.21 (C$_2$), 138.27 (C$_{1'}$), 165.72 (CONH), 169.77 (COCH$_3$) ppm; mass spectrum, FD (relative intensity) 274 (M$^+$+2, 12), 273 (M$^+$+1, 77), 272 (100), 205 (34), 274 (18).

Anal. Calcd for C$_{14}$H$_{16}$N$_4$O$_2$: C, 61.75; H, 5.92; N, 20.57. Found: C, 61.95; H, 6.09; N, 20.32.

EXAMPLE 77

Synthesis of 2-Acetamido-N-benzyl-2-(1-pyrazole)acetamide. A solution of 2-acetamido-N-benzyl-2-bromoacetamide (prepared from 2-acetamido-N-benzyl-2-ethoxyacetamide (3.60 g, 14.4 mmol) and BBr$_3$ (1M CH$_2$Cl$_2$ solution, 15.8 mL, 15.8 mmol)) was prepared in THF (250 mL) and cooled to −78° C. A solution of triethylamine (2.91 g, 28.8 mmol) in THF (20 mL) was then added to the above solution. This was followed by the addition of THF (30 mL) solution of pyrazole (1.17 g, 17.28 mmol) and the mixture thus obtained was stirred at −78° C. (30 min) and room temperature (1 h). The insoluble materials were filtered and the solvents removed from the filtrate in vacuo. The residue was then purified by flash column chromatography on silica gel using 4% MeOH/CHCl$_3$ as the eluant to give 0.80 g (22%) of the desired product. It was then recrystallized from EtOAc as a white solid: nap 158°–160° C.; R$_f$ 0.51 (6% MeOH/CHCl$_3$); $^1$H NMR (DMSO-d$_6$) δ1.93 (s, COCH$_3$), 4.29 (d,J=5.8 Hz, NH), 6.26 (s, C$_4$H), 6.57 (d,J=8.8 Hz, CH), 7.15–7.33 (m, 5PhH), 7.48 (br s, C$_5$H), 7.76 (br s, C$_3$H), 8.96 (t,J=5.8 Hz, NH), 9.23 (d,J=8.8 Hz, NH); $^{13}$C NMR (DMSO-d$_6$) 22.41 (COCH$_3$), 42.40 (CH$_2$), 65.51 (CH), 105.37 (C$_4$), 126.87 (C$_{4'}$), 127.14 (2C$_{2'}$ or 2C$_{3'}$), 128.25 (2C$_{2'}$ or 2C$_{3'}$), 129.00 (C$_5$), 138.59 (C$_3$), 139.17 (C$_{1'}$), 165.68 (CONH), 169.81 (COCH$_3$) ppm; mass spectrum, m/e (relative intensity) 273 (M$^+$+1, 11), 272 (M$^+$, 2), 139 (83), 138 (100), 92 (37).

Anal. Calcd for C$_{14}$H$_{16}$N$_4$O$_2$: C, 61.75; H, 5.92; N, 20.57. Found: C, 61.95; H, 5.96; N, 20.28.

EXAMPLE 78

Synthesis of 2-Acetamido-N-benzyl-2-(1-(1,2,4-triazole))acetamide. Using 2-acetamido-N-benzyl-2-ethoxyacetamide (4.00 g, 16.0 mmol), BBr$_3$ (1M CH$_2$Cl$_2$ solution, 17.6 mL, 17.6 mmol), Et$_3$N (4.85 g, 48.0 mmol), and 1,2,4-triazole (1.43 g, 20.8 mmol), 1.20 g (28%) of the desired product was obtained. It was recrystallized from EtOAc as an amorphous white solid: mp 146°–148° C.; R$_f$0.48 (6% MeOH/CHCl$_3$); $^1$H NMR (DMSO-d$_6$) δ1.85 (s, COCH$_3$), 4.32 (br s, CH$_2$), 6.70 (d,J=7.8 Hz, CH), 7.21–7.29 (m, 5PhH), 8.01 (s, C$_3$H), 8.57 (s, C$_5$H), 9.04 (br s, NH), 9.39 (d,J=7.8 Hz, NH); $^{13}$C NMR (DMSO-d$_6$) 22.39 (COCH$_3$), 42.59 (CH$_2$), 65.02 (CH), 126.97 (C$_{4'}$), 127.25 (2C$_{2'}$ or 2C$_{3'}$), 128.32 (2C$_{2'}$ or 2C$_{3'}$), 138.47 (C$_{1'}$), 143.93 (C$_5$), 151.50 (C$_3$), 164.77 (CONH), 170.23 (COCH$_3$) ppm; mass spectrum, FD (relative intensity) 275 (M$^+$+2, 12), 274 (M$^+$+1, 100), 273 (11), 205 (19), 204 (13), 140 (67), 139 (31).

Anal. Calcd for C$_{13}$H$_{15}$N$_5$O$_2$: C, 57.13; H, 5.53; N, 25.63. Found: C, 57.37; H, 5.66; N, 25.38.

EXAMPLE 79

Synthesis of 2-Acetamido-N-benzyl-2-(1-tetrazole)-)acetamide. Making use of 2-acetamido-N-benzyl-2-ethoxyacetamide (3.00 g, 12.0 mmol), BBr$_3$ (1M CH$_2$Cl$_2$ solution, 13.2 mL, 13.2 mmol), Et$_3$N (2.42 g, 24.0 mmol), and tetrazole (1.10 g, 15.6 mmol), 0.90 g (27%) of the desired product was obtained as a white solid. It was recrystallized from EtOH: mp 169°–171° C.; R$_f$0.22 (4% MeOH/CHCl$_3$); $^1$H NMR (DMSO-d$_6$) δ1.97 (s, COCH$_3$), 4.25–4.40 (m, CH$_2$), 7.05 (d,J=8.4 Hz, CH), 7.21–7.38 (m, 5PhH), 9.23 (t,J=5.5 Hz, NH), 9.44 (s, C$_5$H), 9.69 (d,J=8.4 Hz, NH); $^{13}$C NMR (DMSO-d$_6$) 22.38 (COCH$_3$), 42.78 (CH$_2$), 63.62 (CH), 127.10 (C$_{4'}$), 127.39 (2C$_{2'}$ or 2C$_{3'}$), 128.38 (2C$_{2'}$ or 2C$_{3'}$), 138.26 (C$_{1'}$), 143.67 (C$_5$), 163.88 (CONH), 170.62 (COCH$_3$) ppm; mass spectrum, FD (relative intensity) 275 (M+79), 273 (14), 206 (100), 205 (50).

Anal. Calcd for C$_{12}$H$_{14}$N$_6$O$_2$: C, 52.55; H, 5.15; N, 30.64. Found: C, 52.75; H, 5.33; N, 30.64.

EXAMPLE 80

Preparation of
α-acetamido-N-benzyl-2-pyridylacetamide and
2-acetamido-N-benzyl-2-(2'-pyridone)acetamide Preparation of
2-acetamido-2-bromo-N-benzylacetamide A solution of 2-acetamido-2-ethoxy-N-benzylacetamide (2.00 g, 8 mmol) in dry CH$_2$Cl$_2$ (200 mL) was stirred at room temperature as a solution of BBr$_3$ (8.8 mL, 8.8 mmol, 1.0M in CH$_2$Cl$_2$) was introduced by means of a syringe under a nitrogen atmosphere. A white mist formed and after it disappeared, the N$_2$ line was removed and the reaction sealed. The resulting yellow solution was stirred (3.5 h) and then concentrated in vacuo to give yellow crystals of α-acetamido-2-bromo-N-benzyl acetamido which was stored under vacuum overnight.

Preparation of 2-pyridyllithium

The generation of 2-pyridyllithium in situ was run under nitrogen. A solution of n-butyllithium (7.2 mL, 2.5M solution in hexane, 18 mmol) was added to dry ether (60 mL), cooled to −20° C., and stirred as 2-bromopyridine (1.6 mL, 17 mmol) in dry ether (15 ml.) was added dropwise (15 min). The resulting blood red solution was stirred at −20° C. for an additional 5 minutes and then transferred through a doubled-ended needle under a stream of nitrogen to an addition funnel where it was cooled to −78° C.

Preparation of
α-acetamido-N-benzyl-2-pyridylacetamide and
2-acetamido-N-benzyl-2-(2-pyridone)acetamide The cooled 2-pyridyllithium solution was added dropwise (approximately 2 drops per second) to the solution of 2-acetamido-2-bromo-N-benzylacetamide in dry THF (200 mL) and maintained at −78° C. The reaction mixture was stirred for an additional 30–45 minutes at −78° C. The reaction was quenched with saturated aqueous solution of NH$_4$Cl (40 mL) at −78° C. producing a heterogenous mixture Na$_2$CO$_3$ was added dropwise until the precipitate dissolved. The organic layer was separated and then the aqueous layer was extracted with ether (2×50 mL). The combined organic layers were dried (Na$_2$SO$_4$), concentrated under vacuum and separated using flash chromatography on silica gel with ethyl acetate as the eluent. The fractions containing the products were concentrated under vacuum, separated and then further purified by column chromatography on alumina (80–200 mesh, Grade 1, Fisher) employing ethyl acetate as the solvent. Fractions containing α-acetamido-N-benzyl-2-pyridylacetamide was concentrated to dryness and gave a white amorphous solid (250 mg, 11% yield); R$_f$=0.39 (5% CH$_3$OH/CHCl$_3$); mp 146°–147° C.; IR (KBr) 3290, 3180, 3020, 1620 br, 1580, 1520 br, 1480, 1420, 1370, 1310, 1260 cm$^{-1}$; $^1$H NMR (300 MHz, DMSO-d$_6$) δ1.96 (s, 3H), 4.28 (d,J=5.8 Hz, 2H), 5.59 (d,J=8.0 Hz, 1H), 7.18–7.30 (m, 5H), 7.32 (dd,J=7.7, 5.2 Hz, 1H), 7.47 (d,J=7.7 Hz, 1H), 7.80 (dt,J=7.7, 1.5 Hz, 1H), 8.55 (m, 2H), 8.78 (br t,J=5.8 Hz, 1H); $^{13}$C NMR (75MHz, DMSO-d$_6$) 22.5, 42.1, 58.3, 121.7, 122.8, 126.6, 126.9 (2C), 128.1 (2C), 136.8, 139.1, 148.6, 157.2, 169.0, 169.2 ppm; FD (Lilly) mass spectrum, m/e (relative intensity) 284 (M$^+$+1, 6), 283 (M$^+$, 0.8), 151 (8), 150 (100), 141 (4). C$_{16}$H$_{17}$N$_3$O$_2$ Anal. Calcd for C 67.83, H, 6.05, N, 14.83 Found: C, 68.11, H, 6.00, N, 14.89.

Fractions containing 2-acetamido-N-benzyl-2-(2'-pyridone)acetamide were combined, concentrated in vacuo and yielded a white amorphous solid: (150 mg, 6% yield). R$_f$ 0.34 (5% CH$_3$OH/CHCl$_3$); mp 226 decomposed (recrystallized in ethanol) 1H NMR (300 MHx, DMSO-d$_6$) δ1.94 s, 4.26 (dd,J=15.2, 5.7 Hz, 1H), 4.33 (dd,J=15.2, 6.1 Hz, 1H),6.26 (br t,J=6.8 Hz, 1H), 6.37 (br d,J=9.1 Hz, 1H), 6.69 (d, J=8.7 Hz, 1H), 7.22–7.33 (m, 5H), 7.42 (ddd,J=9.1, 6.8, 1.6 Hz, 1H), 7.58 (dd,J=6.8, 1.6 Hz, 1H), 8.93 (br t,J=5.8 Hz, 1H), 9.20 (d,J=8.7 Hz, 1H); $^{13}$C NMR (75 MHz, DMSO-d$_6$) 22.5, 42.5, 62.5, 105.1, 119.4, 126.8..6, 127.10(2C), 128.2 (2C), 135.6, 138.8, 140.2, 161.2, 166.0, 170.0 ppm. Hydrogen and carbon assignments were verified with $^1$H-$^1$H COSY, $^1$H-$^{13}$C-COSY, zero quantum NMR experiments. The structure was conformed by X-Ray crystallography.

Preparation of authentic
2-acetamido-N-benzyl-2-(2'-pyridone)acetamide

The generation of 2-hydroxypyridylsodium in situ was done under anhydrous conditions. A solution of 2-hydroxypyridine (1.57 g, 16 mmol, vacuum dried, 97% Aldrich) in dry THF (200 mL) was stirred and cooled to 0° C. and then NaH (0.77 g, 60% in mineral oil, 19.2 mmol) was added in one portion leading to the evolution of H$_2$ and the generation of a heterogeneous mixture. A solution of 2-acetamido-2-bromo-N-benzylacetamide (8 mmol based on 2-acetamido-2-ethoxy-N-benzylacetamide) in dry THF (160 mL) was then transferred through a double-ended needle by means of a stream of nitrogen. The resulting mixture was quenched with saturated aqueous solution of NH$_4$Cl (50 mL) at 0° C. producing a white precipitate. A saturated aqueous solution Na$_2$CO$_3$ was added dropwise while stirring at 0° C. until all of the white precipitate dissolved. The two layers were separated while cold and then the aqueous fraction was extracted with THF (2×100 mL). The combined organic layers were dried (Na$_2$SO$_4$), and concentrated to dryness. The crude reaction mixture residue was dissolved in a minimum of CHCl$_3$and was flash chromatographed on a silica gel column using ethyl acetate as the eluent and gave a white amorphous solid (1.10 g, 46% yield) which was identical to properties previously observed for 2-acetamido-N-benzyl-2-(2'-pyridone)acetamide: R$_f$ 0.34 (5% CH$_3$0H]CHCl$_3$); mp 162°–163.5° C. (recrystallized in ethyl acetate); IR (KBr) 3300, 3280, 3260, 3080, 1690, 1680, 1650 br, 1580, 1570, 1520, 1490, 1140 cm$^{-1}$; $^1$H NMR (300 MHz, DMSO-d$_6$) δ1.96 (s, 3H), 4.27 (dd,J=15.3, 5.8 Hz, 1H), 4.36 (dd,J=15.3, 6.2 Hz, 1H), 6.27 (dt,J=6.8, 1.1 Hz, 1H), 6.39 (bd,J=8.9 Hz, 1H), 6.71 (d,J=8.7 Hz, 1H), 7.22–7.34 (m, 5H), 7.43 (ddd,J=8.9, 6.8, 1.9 Hz, 1H), 7.59 (dd,J=6.8, 1.9 Hz, 1H), 8.93 (br t,J=5.9 Hz 1H), 9.20 (d,J=8.7 Hz, 1H); $^{13}$C NMR (75 MHz, DMSO-d$_6$) 22.4, 42.5, 62.5, 105.1, 119.4, 126.8, 127.1 (2C), 128.2 (2C), 135.6, 138.8,140.1, 161.1, 166.0, 169.9 ppm; FD (Lilly) mass spectrum, m/e (relative intensity) 598 (2M, 2), 300 (M$^+$+1, 17), 299 (M$^+$, 100), 96 (2), 95 (26). C$_{16}$H$_{17}$N$_3$O$_3$.

Anal. Calcd for C, 64.20, H 5.73, N 14.04.

EXAMPLE 81

α-acetamido-N-benzyl-2-pyridyl acetamide N-oxide

To a cooled solution of 2-α-acetamido-N-benzyl-2-pyridylacetamide dissolved in dry THF is added m-perchloroperbenzoic acid to give the resulting product.

Similarly, using the procedure described hereinabove, the following examples are prepared.

2-acetamido-N-benzyl-2-(3-pyridyl)acetamide and the N-oxide thereof, 2-acetamido-N-benzyl-2-(4-pyridyl)acetamide and the N-oxide thereof, 2-acetamido-N-benzyl-2-(2-pyrimidinyl)acetamide and the N-oxide thereof 2-acetamido-N-benzyl-2-(4-pyrimidinyl)acetamide and the N-oxide thereof, 2-acetamido-N-benzyl-2-(5-pyrimidinyl)acetamide and the N-oxide thereof, 2-acetamido-N-benzyl-2-(3-pyridazinyl)acetamide and the N-oxide thereof, 2-acetamido-N-benzyl-2-(2-pyridazinyl)acetamide and the N-oxide thereof, 2-acetamido-N-benzyl-2-(4-pyrazinyl) acetamide and the N-oxide thereof, 2-acetamido-N-benzyl-2-(2-thiazolyl)acetamide,
2-acetamido-N-benzyl-2-(2-oxazolyl)acetamide,
2-acetamido-N-benzyl-2-(3-isoxazolyl)acetamide,
2-acetamido-N-benzyl-2-(5-isoxazolyl)acetamide,
2-acetamido-N-benzyl-2-(3-isothiazolyl)acetamide, and
2-acetamido-N-benzyl-2-(5-isothiazolyl)acetamide.

General Procedure. 2-Acetamido-N-benzyl-2-ethoxyacetamide (1equiv.) was suspended in anhydrous ethyl ether, and then boron trifluoride etherate (1.6–6.3 equiv.) was rapidly added and the resulting solution was stirred for 15 min. The aromatic substrate (1.6–16 equiv.) was then added and the reaction was stirred at room temperature (1–7 days).

EXAMPLE 82

α-Acetamido-N-benzyl-2-(S-thiophenoxy)-acetamide (II). The reaction mixture was treated wtih an aqueous saturated NaHCO$_3$ solution and the white insoluble solid was filtered and then washed successively with H$_2$O and hexanes. The desired product was purified by recrystallization from chloroform hexanes to give II in 94% yield: R$_f$ 0.43 (97:3 chloroform/methanol): m.p. 165°-167°: i.r. (KBr) 3280, 1630 (br) 1520 (br) 1430 1365 1280 1245, 1180 cm$^{-1}$; $^1$H n.m.r. (DMSO-d$_6$) 81.83 (s, CH$_3$CO). 4.22≅4.36 (m. CH$_2$), 5.90 (d,J=9.0 Hz, NH), 8,84 (t,J=5.4 Hz, NH); $^{13}$C n.m.r (DMSO-d$_6$) 22.34 (CH$_3$CO), 42.25 (CH$_2$), 57.65 (CH). 126.86 (C$_4$'), 127.20 (2C$_2$'), 123.73 (C$_4$'). 128.28 (2C$_2$' or 2C$_3$') 128.88 (2C$_2$' or 2C$_3$'), 132.36 (2C$_3$') 132.51 (C$_1$'), 138.76 (C$_1$), 167.09 (CONH), 168.97 (CH$_3$CO) ppm; mass spectrum, m/e (relative intensity) 315 (M+1,1), 205 (17), 163 (40), 138 (8), 110 (90), 109 (29), 106 (96), 93 (35), 91 (100).

Anal. calc. for C$_{17}$H$_{18}$N$_2$O$_2$S: C 64.94, H 5.77. Found: C 65.27, H 5.54.

Pharmacology. Using male Carworth Farms #1 mice, compounds of the present invention were tested for anti-convulsant activity according to the following procedure: In the rotorod test, the animal was placed on a one-inch diameter knurled plastic rod rotating at 6 rpm after the administration of the drug. Normal mice can remain on a rod rotating at this speed indefinitely. Neurologic toxicity was defined as the failure of the animal to remain on the rod fox one minute. In the horizontal screen test, previously trained mice were dosed with the compound and placed individually on top of a square (13 cm ✕ 13 cm) wire screen (no. 4 mesh) which was mounted on a metal rod. The rod was rotated 180°, and the number of mice that returned to the top of the screen was determined. Inability to climb to the top within one minute was defined as "neurological impairment". This procedure is described in *Pharmacol. Biochem. Behav.* 6, 351–353 (1977). and is incorporated herein by reference with the same force and effect as if fully set forth herein.

The dose effect behavior of the compounds was evaluated using the above-described procedures by the administration of varying dose levels, treating normally eight mice at each dose. Table I includes an evaluation of the Median Effective Dose (ED50) and the Median Toxic Dose (TD50) of representative compounds. Mice were tested with varying doses of the anticonvulsant to define the limits of complete protection (or toxicity) and no protection (or no toxicity), as well as three points in between these limits. The Median Effective Dose (ED50) was defined as the dose which produced the desired endpoint in 50% of the animals. The Median Toxicity Dose (TD50) was the dose which elicited evidence of minimal neurological toxicity in 50% of the animals.

More specifically, data tabulated in Table 1 were generated as follows:

The compound was given in various dose levels (i.e., 10, 30, 100, 300 mg) and subsequently compared with phenytoin, phenobarbital, mephenytoin arid phenacemide (See Table I). N-Acetyl-D,L-alanine-N'-benzylamide was tested at 600 mg/mL as well. Seizures were then artifically induced by either electroschock or pentylenetetrazole. Maximal electroshock seizures (MES) were elicited with a 60 cycle alternating current of 50mA intenstiy (5-7 times that necessary to elicit minimal electroshock seizures) delivered for 0.2 sec via corneal electrodes. A drop of 0.9% saline was instilled in the eye prior to application of the electrodes so as to prevent the death of the animal. Protection in this test was defined as the abolition of the hind limb tonic extension-component of-the seizure. The Subcutaneous Pentylenetetrazole (Metrazol$^R$) Seizure Threshold Test (sc Met) entailed the administration of 85 mg/kg of pentylenetetrazole as a 0.5% solution subcutaneously in the posterior midline. This amount of pentylenetetrazole was expected to produce seizures in greater than 95% of mice. The animal was observed for 30 minutes. Protection was defined as a failure to observe even a threshold seizure (a single episode of clonic spasms of at least 5 sec duration). The results of these tests are tabulated in Table I.

TABLE I

| | Comparative Median Effective Dosage | | |
|---|---|---|---|
| Compound | Tox TD50 mg/kg | MES ED50 mg/kg | sc Met ED50 mg/kg |
| N-acetyl-D,L-alanine-N'-benzylamide | 454 (417–501)* | 77 (67–89)* | ‡ |
| N-acetyl-D-alanine-N'-benzylamide | 214 (148–262)* | 55 (50–60)* | 55 (43–67)* |
| N-acetyl-L-alanine-N'-benzylamide | 841 (691–594)* | 548 (463–741)* | ‡ |
| N-acetyl-D,L-phenylglycine-N'-benzylamide | >>40 | 32.1 | ‡ |
| N-acetyl-D-phenyl-glycine-N'-benzyl-amide | >>80 | 26.4 | ‡ |
| N-acetyl-L-phenyl-glycine-N'-benzyl-amide | 100–300 | >300 | ‡ |
| D,L-α-acetamido-N-benzyl-3-thiophene-acetamide | >100 | 87.80 | ‡ |
| D,L-α-acetamido-N-benzyl-2-thiophene-acetamide | 30–100 | 44.80 | ‡ |
| D,L-α-acetamido-N-benzyl-2-furan-acetamide | 40 | 10.33 | ‡ |
| D,L-α-acetamido-N-benzyl-2-pyrrole-acetamide | <100 | 16.10 | ‡ |
| D,L-2-acetamido-N-benzyl-2-ethoxy-acetamide | >112 | 62.01 | ‡ |

TABLE I-continued

| | Comparative Median Effective Dosage | | |
|---|---|---|---|
| Compound | Tox TD50 mg/kg | MES ED50 mg/kg | sc Met ED50 mg/kg |
| D,L-2-acetamido-N-benzyl-2-methoxy-acetamide | <300 | 98.30 | ‡ |
| (D,L)-α-Acetamido-N-benzyl-2-(5-methylfuran) acetamide | 75.4$^{xx}$ | 19.2 (16.4–23.8)* | ‡ |
| (D,L)-α-Acetamido-N-benzyl-2-benzofuran-acetamide | >100 <300$^{xx}$ | >100 <300 | ‡ |
| (D,L)-α-Acetamido-N-benzyl-2-benzo[b]-thio-pheneacetamide | >100 <300$^{xx}$ | >100 <300 | ‡ |
| (D,L)-α-Acetamido-N-benzyl-2-(5-methylpyrrole) acetamide | x | 36.5 (30.6–57.1)* | ‡ |
| (D,L)-α-Acetamido-N-(2-fluorobenzyl)-2-furan-acetamide | x | 40.0 | ‡ |
| (DL)-α-Acetamido-N-(3-fluorobenzyl)-2-furan-acetamide | 135.6 (114.9–161.8)$^{xx}$ | 13.3 (11.5–15.3)* | ‡ |
| 2-acetamido-N-benzyl-2-aminoacetamide | ‡ | 65.1 (56.2–75.3) | ‡ |
| 2-acetamido-N-benzyl-2-(1-Pyrrolyl) acetamide | ‡ | 80.2 | ‡ |
| 2-acetamido-N-benzyl-2-(1-imidazoyl) acetamide | ‡ | >100 | ‡ |
| 2-acetamido-N-benzyl-2-(N,N-dimethylamino)acetamide | ‡ | 45.3 | ‡ |
| 2-acetamido-N-benzyl-2-(4-morpholine)acetamide | ‡ | >30, <100 | ‡ |
| 2-acetamido-N-benzyl-2-(N,N,N-trimethylammonium) acetamide tetrafluoroborate | ‡ | >100 | ‡ |
| 2-acetamido-N-benzyl-2-(N-anilino)acetamide | ‡ | >300 | ‡ |
| 2-acetamido-N-benzyl-2-(N-(3-pyrazolylamino)) acetamide | ‡ | ~100 | ‡ |
| 2,2-diacetamido-N-benzyl-acetamide | ‡ | >100, <300 | ‡ |
| 2-acetamido-N-benzyl-2-trifluoroacetamidoacetamide | ‡ | >300 | ‡ |
| 2-acetamido-N-benzyl-2-(N-hydroxyamino)acetamide | ‡ | ~100 | ‡ |
| 2-acetamido-N-benzyl-2-(N-methoxyamino)acetamide | 46.0$^{xx}$ (38.0–56.0) | 6.2 (5.4–7.2) | ‡ |
| 2-acetamido-N-benzyl-2-(N-(N-methylhydroxyamino)) acetamide | ‡ | ~30 | |
| 2-acetamido-N-benzyl-2-(N-(N,O-dimethylhydroxy-amino)acetamide | 50.5$^{xx}$ (40.4–59.9) | 6.7 (5.7–7.7) | ‡ |
| 2-acetamido-N-benzyl-2-(N-isoxazolidino)acetamide | ‡ | 31.4 (26.7–37.8) | |
| 2-acetamido-N-benzyl-2-(N$^2$-phenylhydrazino) acetamide | | ~100 | |
| 2-acetamido-N-benzyl-2-(N$^2$-benzyloxycarbonyl-hydrazino)acetamide | ‡ | 55.6 (49.3–63.9) | ‡ |
| 2-acetamido-N-benzyl-2-hydroxyacetamide | ‡ | 80.1 (70.6–91.0) | ‡ |
| 2-acetamido-N-benzyl-2-(1-Pyrazolyl) acetamide | ‡ | 16.5 (14.1–22.5) | ‡ |
| 2-acetamido-N-benzyl-2-phenoxyacetamide | ‡ | >100 | ‡ |
| 2-acetamido-N-benzyl-2-(methylmercapto)acetamide | ‡ | >100 | ‡ |
| 2-acetamido-N-benzyl-2-(ethylmercapto)acetamide | ‡ | >30, <100 | ‡ |
| 2-acetamido-N-benzyl-2-(S-thiophenoxy)acetamide | ‡ | >300 | ‡ |
| 2-acetamido-N-benzyl-2-(ethylmercapto)acetamide-S-oxide (diastereomer A) | ‡ | >100 | ‡ |
| 2-acetamido-N-benzyl-2-(ethylmercapto)acetamide-S-oxide (diastereomers A + B) | ‡ | >100 | ‡ |

TABLE I-continued

| | Comparative Median Effective Dosage | | |
|---|---|---|---|
| Compound | Tox TD50 mg/kg | MES ED50 mg/kg | sc Met ED50 mg/kg |
| 2-acetamido-N-benzyl-2-(ethylsulfonyl)acetamide | | >100 | ‡ |
| (D,L)-α-Acetamido-N-(4-fluorobenzyl)-2-furanacetamide | 144.4 (122.5–170.9)xx | 12.7 (10.4–15.1)* | ‡ |
| (D,L)-α-Acetamido-N-(2,5-difluorobenzyl)-2-furanacetamide | x | 23.8 (20.2–28.4) | ‡ |
| (D,L)-α-Acetamido-N-(2,6-difluorobenzyl)-2-furanacetamide | x | >25 <100 | ‡ |
| (D)-(−)-α-Acetamido-N-benzyl-2-furanacetamide | 23.8xx | 3.3 (2.8–3.9) | ‡ |
| (L)-(+)-α-Acetamido-N-benzyl-2-furanacetamide | >300 | >100 <300 | ‡ |
| (D,L)-2-Acetamido-4-pentenoic acid-N-benzylamide | x | 33.6 | ‡ |
| 2-acetamido-N-benzyl-2-(2-Pyridyl) acetamide | ‡ | 8.5 | ‡ |
| (D,L)-2-Acetamido-N-benzyl-2-(methylamino)acetamide | 95.0 | 44.5 (37.0–52.4)* | ‡ |
| (D,L)-2-Acetamido-N-benzyl-2-(ethylamino)acetamide | X | 42.4 (37.2–47.8)* | ‡ |
| (D,L)-2-Acetamido-N-benzyl-3-indoleacetamide | x | xxx | ‡ |
| phenytoin | 66 | 10 | not effective |
| phenobarbital | 69 | 22 | 13 |
| mephenytoin | 154 | 61 | 31 |
| phenacemide | 421 (337–549)* | 87 (74–100)* | 116 (71–150)* |

*95% confidence intervals.
‡ or x The TD50 for this substrate was not computed.
xx The TD50 value was determined using the horizontal screen test.
XXX No activity was noted at ≦300 mg/kg Thus, while the invention has been described with reference to certain preferred embodiments, those skilled in the art will realize that changes and modifications may be made thereto without departing from the full and intended scope of the appended claims.

We claim:

1. An anticonvulsant composition comprising an anticonvulsant effective amount of a compound having the following general formula:

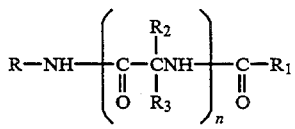

wherein R is aryl, aryl lower alkyl, heterocyclic lower alkyl, lower alkyl, or heterocyclic, each unsubstituted or substituted with at least one electron withdrawing substituent or at least one electron donating substituent;

$R_1$ is H or lower alkyl, unsubstituted or substituted with at least one electron withdrawing substituent or at least one electron donating substituent;

$R_2$ and $R_3$, independently, are hydrogen, lower alkyl, lower alkenyl, lower alkynyl, aryl, aryl lower alkyl, heterocyclic lower alkyl, or heterocyclic, each unsubstituted or substituted with at least one electron withdrawing substituent or at least one electron donating substituent; halogen or a heteroatom containing oxygen, nitrogen, or sulfur said heteroatom being substituted with hydrogen, lower alkyl or aryl, said lower alkyl or aryl groups being substituted or unsubstituted;

n is 1 to 4; and a pharmaceutically acceptable carrier.

2. The composition according to claim 1 wherein R is aryl lower alkyl, heterocyclic lower alkyl or heterocyclic, each of which may be unsubstituted or substituted with at least one halo, nitro, acyl, carboxyl, carboalkoxy, carboxamide, cyano, sulfonyl, sulfoxide, heterocyclic, guanidine, quaternary ammonium, hydroxy, lower alkoxy, lower alkyl, amino, or phenoxy;

$R_1$ is H or lower alkyl which may be unsubstituted or substituted with at least one halo, nitro, acyl, carboxamido, cyano, sulfonyl, sulfoxide, heterocyclic, guanidine, ammonium, hydroxy, lower alkoxy, amino, or phenoxy;

$R_2$ is hydrogen, lower alkyl, lower alkenyl, lower alkynyl, aryl, heterocyclic lower alkyl, or heterocyclic, each unsubstituted or substituted with at least one electron withdrawing substituent or at least one electron donating substituent; or $R_2$ is halogen or a heteroatom consisting of nitrogen oxygen or sulfur each substituted with hydrogen, lower alkyl or aryl, said lower alkyl or aryl groups being substituted or unsubstituted;

$R_3$ is hydrogen, lower alkyl, lower alkenyl, lower alkynyl, aryl, heterocyclic lower alkyl, or heterocyclic, each unsubstituted or substituted with at least one electron withdrawing substituent or at least one electron donating substituent; or $R_3$ is halogen, or a heteroatom consisting of oxygen, nitrogen, or sulfur substituted with hydrogen, lower alkyl or aryl, said lower alkyl or aryl groups being substituted or unsubstituted and n is 1–4.

3. The composition according to claim 1 wherein one of $R_2$ and $R_3$ is other than hydrogen.

4. The composition according to claim 1 wherein n is 1.

5. The composition according to claim 1 wherein n is 1 and one of $R_2$ and $R_3$ is hydrogen and the other is heterocyclic or lower alkyl heterocyclic.

6. The composition according to claim 1 wherein n is 1 and one of $R_2$ and $R_3$ is hydrogen and the other is aryl.

7. The composition according to claim 1 wherein one of $R_2$ and $R_3$ is hydrogen and the other is thienyl, furyl, pyrrolyl or phenyl.

8. The composition according to claim 1 wherein one of $R_2$ and $R_3$ is hydrogen and the other is lower alkenyl or lower alkynyl.

9. The composition according to claim 1 wherein one of $R_2$ and $R_3$ is hydrogen and the other is lower alkoxy.

10. The composition according to claim 1 wherein one of $R_2$ and $R_3$ is hydrogen and the other is lower alkyl.

11. The composition of claim 1 having a unit dosage form containing from about to 5 to about 1000 mg of said compound.

12. The composition of claim 1 wherein $R_1$ is hydrogen, methyl, ethyl, propyl, isopropyl, butyl, isobutyl, tertiary butyl, amyl or hexyl.

13. The composition of claim 12 wherein said methyl, ethyl, propyl, isopropyl, butyl, isobutyl, tertiary butyl, amyl or hexyl are unsubstituted or substituted with at least one electron withdrawing substituent or at least one electron donating substituent.

14. The composition of claim 12 wherein $R_1$ is methyl.

15. The composition of claim 1 wherein R is benzyl, unsubstituted or substituted with at least one electron withdrawing substituent or at least one electron donating substituent.

16. The composition of claim 1 wherein said electron withdrawing substituent is halo, nitro, acyl, carboxyl, carboalkoxy, carboxamide, cyano, sulfonyl, sulfoxide, heterocyclic, guanidine or quaternary ammonium.

17. The composition of claim 1 wherein said electron donating substituent is hydroxy, alkoxy, alkyl, amino or phenoxy.

18. The composition of claim 1 wherein R is benzyl, $R_1$ is methyl, $R_2$ is hydrogen, $R_3$ is methyl and n is 1 or the D or L steroisomer.

19. The composition of claim 1 wherein R is benzyl, $R_1$ is methyl, $R_2$ is hydrogen, $R_3$ is phenyl and n is 1 or the D or L stereoisomer.

20. The composition of claim 1 wherein R is benzyl, $R_1$ is methyl, $R_2$ and $R_3$ are hydrogen and n is 1.

21. The composition of claim 1 wherein R is benzyl, $R_1$ is methyl, $R_2$ is hydrogen, $R_3$ is isopropyl and n is 1 or the D or L stereoisomer;

R is benzyl, $R_1$ is t-butyl, $R_2$ is hydrogen, $R_3$ is methyl and n is 1 or the D or L stereoisomer;

R is benzyl, $R_1$ is methyl, $R_2$ is hydrogen, $R_3$ is (2-thiomethyl)ethyl and n is 1 or the D or L stereoisomer;

R is (3-fluoro)benzyl, $R_1$ is methyl, $R_2$ is hydrogen, $R_3$ is methyl and n is 1 or the D or L stereoisomer;

R is (3-methoxy)benzyl, $R_1$ is methyl, $R_2$ is hydrogen, $R_3$ is methyl and n is 1 or the D or L stereoisomer;

R is benzyl, $R_1$ is methyl, $R_2$ is (3-thienyl), $R_3$ is hydrogen and n is 1 or the D or L stereoisomer;

R is benzyl, $R_1$ is methyl, $R_2$ is (2-thienyl), $R_3$ is hydrogen and n is 1 or the D or L stereoisomer;

R is benzyl, $R_1$ is methyl, $R_2$ is (2-furyl), $R_3$ is hydrogen and n is 1 or the D or L stereoisomer;

R is benzyl, $R_1$ is methyl, $R_2$ is (2-pyrrolyl), $R_3$ is hydrogen and n is 1 or the D or L steroisomer;

R is benzyl, $R_1$ is methyl, $R_2$ is ethoxy, $R_3$ is hydrogen and n is 1 or the D or L stereoisomer; or R is benzyl, $R_1$ is methyl, $R_2$ is methoxy, $R_3$ is hydrogen and n is 1 or the D or L steroisomer.

22. The composition of claim 1 wherein said compound is in the D isomer form, L isomer form, mixtures of the D,L isomer form or D,L racemic form.

23. An anticonvulsant composition comprising an anticonvulsant effective amount of a compound having the formula:

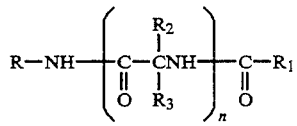

and pharmaceutically acceptable salts thereof wherein

R is aryl, aryl lower alkyl, heterocyclic or heterocyclic lower alkyl, wherein R is unsubstituted or is substituted with at least one electron withdrawing group or an electron donating group;

$R_1$ is hydrogen or lower alkyl which is unsubstituted or is substituted with at least one electron withdrawing substituent or at least one electron donating substituent;

$R_2$ and $R_3$ are independently each hydrogen, lower alkenyl, lower alkynyl, aryl lower alkyl, aryl, heterocyclic, lower alkyl, heterocyclic lower alkyl or Z-Y, wherein $R_2$ and $R_3$ may be unsubstituted or substituted with at least one electron withdrawing group or electron donating group;

Z is O, S, $NR_4$, or a chemical bond;

Y is hydrogen, lower alkyl, aryl, aryl lower alkyl, lower alkenyl, lower alkynyl, or halo, and Y may be unsubstituted or substituted with at least one electron withdrawing group or electron donating group, provided that when Y is halo, Z is a chemical bond or ZY taken together is $NR_4NR_5R_6$, $NR_4OR_5$, $ONR_4R_5$, $SNR_4R_5$, or $NR_4SR_5$, $R_4$, $R_5$ and $R_6$ are independently hydrogen, lower alkyl, aryl, aryl lower alkyl, lower alkenyl, lower alkynyl and $R_4$, $R_5$ and $R_6$ may be unsubstituted or substituted with an electron withdrawing group or an electron donating group and n is 1–4, and a pharmaceutically acceptable carrier therefor.

24. The composition of claim 23 having a unit dosage form containing from about 5 to about 1000 mg of said compound.

25. The composition of claim 23 wherein $R_1$ is methyl.

26. The composition of claim 23 wherein R is aryl lower alkyl.

27. The composition of claim 26 wherein R is benzyl.

28. The composition of claim 23 wherein the electron withdrawing group is halo, nitro, lower alkanoyl, aryloyl, aryl lower alkanoyl, carboxy, carbalkoxy, carboxamido, cyano, sulfonyl, sulfoxide, heterocyclic, guanidine or quaternary ammonium.

29. The composition of claim 23 wherein the electron donating group is hydroxy, lower alkoxy, lower alkyl, amino, lower alkylamino, di(loweralkyl)amino, or phenoxy.

30. The composition according to claim 23 wherein $R_2$ and $R_3$ are independently hydrogen, phenyl, hydroxy, phenoxy, alkyl containing 1–4 carbon atoms, lower alkoxy, amino, lower alkylthio, morpholinyl, thienyl, furyl, pyrrolyl, methylfuryl, benzofuryl, benzothienyl, indolyl, methylpyrrolyl, lower alkenyl, anilino, arylamino, lower alkylamino, hydrazino, lower alkyl hydrazino, mercapto, arylthio, N-phenylhydrazine, N-hydroxylamino or O-hydroxylamino.

31. The composition according to claim 23 wherein one of $R_2$ and $R_3$ is hydrogen.

32. The composition according to claim 23 wherein n is 1.

33. The composition according to claim 23 wherein n is 1 and $R_1$ is methyl.

34. The composition according to claim 23 wherein n is 1 and R is aryl lower alkyl.

35. The composition of claim 34 wherein R is benzyl.

36. The composition of claim 23 wherein n is 1 and wherein the electron withdrawing group is halo, nitro, lower alkanoyl, aryloyl, aryl lower alkanoyl, carboxy, carbalkoxy, carboxamido, cyano, sulfonyl, sulfoxide, heterocyclic, guanidine or quaternary ammonium.

37. The composition of claim 23 wherein n is 1 and the electron donating group is hydroxy, lower alkoxy, lower alkyl, amino, lower alkylamino, di(loweralkyl)amino, or phenoxy.

38. The composition according to claim 23 wherein n is 1 and $R_2$ and $R_3$ are independently hydrogen, phenyl, hydroxy, phenoxy, alkyl containing 1–4 carbon atoms, lower alkoxy, amino, lower alkylthio, morpholinyl, thienyl, furyl, pyrrolyl, methylfuryl, benzofuryl, benzotheinyl, indolyl, methylpyrrolyl, lower alkenyl, anilino, arylamino, lower alkylamino, hydrazino, lower alkyl hydrazino, mercapto, arylthio, N-phenyl hydrazino, N-hydroxylamino or O-hydroxylamino.

39. The composition according to claim 23 wherein said compound is in the D isomer form, the L isomer form, mixtures of the (D,L) isomer form or the D,L racemic form.

40. The composition according to claim 23 wherein n is 1 and one of $R_2$ and $R_3$ is hydrogen.

41. The composition of claim 23 wherein R is benzyl, $R_1$ is methyl, $R_2$ is hydrogen, $R_3$ is 5-methyl-2-furyl and n is 1 or the D or L stereoisomer thereof;

R is benzyl, $R_1$ is methyl, $R_2$ is hydrogen, $R_3$ is 2-benzofuryl, n is 1 or the D or L stereoisomer thereof;

R is benzyl, $R_1$ is methyl, $R_2$ is hydrogen, $R_3$ is 2-benzothienyl, n is 1 and the D or L stereoisomer thereof;

R is benzyl, $R_1$ is methyl, $R_2$ is hydrogen, $R_3$ is 3-indolyl, n is 1 or the D or L stereoisomer thereof;

R is benzyl, $R_1$ is methyl, $R_2$ is hydrogen, $R_3$ is 5-methyl-2-pyrrolyl, n is 1 or the D or L stereoisomer thereof;

R is 2-fluorobenzyl, $R_1$ is methyl, $R_2$ is hydrogen, $R_3$ is 2-furyl, n is 1 or the D or L stereoisomer thereof;

R is 3-fluorobenzyl, $R_1$ is methyl, $R_2$ is hydrogen, $R_3$ is 2-furyl, n is 1 or the D or L stereoisomer thereof;

R is 4-fluorobenzyl, $R_1$ is methyl, $R_2$ is hydrogen, $R_3$ is 2-furyl, n is 1 or the D or L stereoisomer thereof;

R is 2,5-difluorobenzyl, $R_1$ is methyl, $R_2$ is hydrogen, $R_3$ is 2-furyl, n is 1 and the D or L stereoisomer thereof;

R is 2,6-difluorobenzyl, $R_1$ is methyl, $R_2$ is hydrogen, $R_3$ is 2-furyl, n is 1 and the D or L stereoisomer thereof;

R is benzyl, $R_1$ is methyl, $R_2$ is hydrogen, $R_3$ is 2-propenyl, n is 1 and the D or L stereoisomer thereof;

R is benzyl, $R_1$ is methyl, $R_2$ is hydrogen, $R_3$ is 1-morpholino, n is 1 and the D or L stereoisomer thereof;

R is benzyl, $R_1$ is methyl, $R_2$ is hydrogen, $R_3$ is anilino, n is 1 and the D or L stereoisomer thereof;

R is benzyl, $R_1$ is methyl, $R_2$ is hydrogen, $R_3$ is methylamino, n is 1 and the D or L stereoisomer thereof; or R is benzyl, $R_1$ is methyl, $R_2$ is hydrogen, $R_3$ is ethylamino, n is 1 and the D or L stereoisomer thereof.

42. An anticonvulsant composition comprising an anticonvulsant effective amount of a compound having the formula:

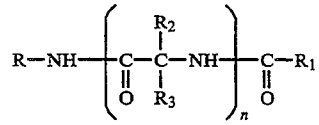

or pharmaceutically acceptable salts thereof wherein

R is aryl, aryl lower alkyl, heterocyclic heterocyclic lower alkyl, lower cycloalkyl, or lower cycloalkyl lower alkyl wherein R is unsubstituted or is substituted with at least one electron withdrawing group or an electron donating group;

$R_1$ is hydrogen or lower alkyl and $R_1$ is unsubstituted or is substituted with at least one electron withdrawing substituent or at least one electron donating substituent;

$R_2$ and $R_3$ are independently hydrogen, lower alkyl, lower alkenyl, lower alkynyl, aryl lower alkyl, aryl, heterocyclic, heterocyclic lower alkyl, cycloalkyl, lower cycloalkyl lower alkyl, or Z-Y wherein $R_2$ and $R_3$ may be unsubstituted or substituted with at least electron withdrawing group or electron donating group;

Z is O, S, S(O), or $NR_4$;

Y is hydrogen, lower alkyl, aryl, aryl lower alkyl, lower alkenyl, lower alkynyl, halo, heterocyclic, heterocyclic lower alkyl, cycloalkyl, or cycloalkyl lower alkyl and Y may be unsubstituted or substituted with an electron donating group or an electron withdrawing group provided that when Y is halo, Z is a chemical bond or ZY taken together is $NR_4NR_5R_7$, $NR_4OR_5$, $ONR_4R_7$, $SNR_4R_7$, $NR_4SR_7$,

$R_4$, $R_5$ and $R_6$ are independently hydrogen, lower alkyl, aryl, aryl lower alkyl, lower alkenyl or lower alkynyl, wherein $R_4$, $R_5$ and $R_6$ may be unsubstituted or substituted with an electron withdrawing group or an electron donating group, $R_7$ is $R_6$ or $COOR_8$ or $COR_8$, $R_8$ is hydrogen or lower alkyl, or aryl lower alkyl, n is 1–4, and a is 1–3.

43. The composition according to claim 42 wherein one of $R_2$ and $R_3$ is other than hydrogen.

44. The composition according to claim 42 wherein n is 1.

45. The composition according to claim 42 wherein one of $R_2$ and $R_3$ is hydrogen and the other is cycloalkyl, cycloalkyl lower alkyl, aryl, heterocyclic, heterocyclic lower alkyl, lower alkenyl, lower alkynyl, or Z-Y wherein $R_2$ and $R_3$ may be unsubstituted or substituted with at least one electron withdrawing group or electron donating group, Z is O, S, $S(O)_a$, $NR_4$, Y is hydrogen, lower alkyl, aryl, aryl lower alkyl, lower alkenyl, lower alkynyl, halo, heterocyclic, heterocyclic lower alkyl, lower cycloalkyl or lower cycloalkyl lower alkyl and Y may be unsubstituted or substituted with an electron donating group or an electron withdrawing group provided that when Y is halo, Z is a chemical bond or ZY taken together is $NR_4NR_5R_7$, $NR_4OR_5$, $ONR_4R_7$, $SNR_4R_7$, $NR_4SR_7$,

$R_4$, $R_5$ and $R_6$ are independently hydrogen, lower alkyl, aryl, aryl lower alkyl, lower alkenyl or lower alkynyl, wherein $R_4$, $R_5$ and $R_6$ may be unsubstituted or substituted with an electron withdrawing group or an electron donating group, $R_7$ is $R_6$ or $COOR_8$ or $COR_8$, $R_8$ is hydrogen or lower alkyl, n is 1–4, and a is 1–3.

46. The composition according to claim 42 wherein one of $R_2$ and $R_3$ is hydrogen and the other is heterocyclic.

47. The composition according to claim 46 wherein heterocyclic has the formula

 XI wherein n is 0 or 1

A, E, L and J are independently CH, or a heteroatom selected from the group consisting of O, N and S;

G is CH or a heteroatom selected from the group consisting of N, O and S but when n is O, G is CH or a heteroatom selected from the group consisting of NH, O and S, with the provision that at most two of A, E, L, J and G are heteroatoms.

48. The composition according to claim 47 wherein one of A, E, L, J and G is a heteroatom.

49. The composition according to claim 47 wherein the heterocyclic is furyl, thienyl, pyrrolyl, pyrazolyl, isoxazolidino or pyridyl.

50. The composition according to claim 42 wherein one of $R_2$ and $R_3$ is hydrogen and the other is N-hydroxylamino, lower alkoxyamino, N-lower alkylhydroxyamino, or N-lower alkyl-O-lower alkyl hydroxyamino.

51. The composition according to claim 42 wherein one of $R_2$ and $R_3$ is hydrogen and the other is lower alkoxy, amino, lower alkylamino or dilower alkylamino.

52. The composition according to claim 42 wherein $R_2$ is heterocyclic, heterocyclic amino, amino, lower alkylamino, lower dialkylamino, hydroxylamino, N-alkyl hydroxylamino, N,O-diloweralkylhydroxylamino, lower alkoxyamino, lower alkoxy, hydrogen, or lower arylalkyloxy carbonyl hydrazino.

53. The composition according to claim 42 wherein $R_2$ is furyl, pyrrolyl, isoxazolidino, amino, methylamino, ethylamino, N,N-dimethylamino, 4-morpholinyl, N,N,N-trimethylammonium, N-anilino, 3-pyrazolylamino, trifluoroacetamido, acetamido, hydroxylamino, N,O-dimethylhydroxyamino, N-methoxyamino, isoxazolidino, benzyloxycarbonyl-hydrazino, hydroxy, methoxy, ethoxy, phenoxy, ethylsulfonyl, ethylsulfinyl or phenyl.

54. The composition according to claim 42 wherein $R_2$ is furyl, pyrrolyl, phenyl benzyloxycarbonylhydrazino, isoxazolidino, N,O-dimethylhydroxyamino, N-methylhydroxyamino, N-methyoxyamino, ethylamino or methylamino.

55. The composition according to claim 42 wherein $R_1$ is lower alkyl.

56. The composition according to claim 42 wherein $R_1$ is methyl.

57. The composition according to claim 42 wherein R is aryl lower alkyl.

58. The composition according to claim 57 wherein R is benzyl.

59. The composition according to claim 42 which is in the D form, the L form, a mixture of the (D,L) form or a racemic mixture of the (D,L) form.

60. The composition according to claim 42 wherein the compound is 2-acetamido-N-benzyl-2-amino acetamide, 2-acetamido-N-benzyl-2-methylamino acetamide, 2-acetamido-N-benzyl-2-(ethylamino)acetamide, 2-acetamido-N-benzyl-2-(N,N-dimethylamino)acetamide, 2-acetamide-N-benzyl-2-(4-morpholino)acetamide, 2-acetamido-N-benzyl-2-($N^2$-phenylhydrazine)acetamide, 2-acetamido-N-benzyl-2-($N^2$-benzyloxy carbonylhydrazino)acetamide, 2-acetamido-N-benzyl-2-hydroxy acetamide, 2-acetamido-N-benzyl-2-methoxy acetamide, or 2-acetamido-N-benzyl-2-ethoxyacetamide, acetamide or the D or L stereoisomer thereof.

61. The composition according to claim 42 where the compound is 2-acetamide-N-benzyl-2-(N-methoxyamino) acetamide or the D or L steroisomer thereof.

62. The composition according to claim 42 wherein the compound is 2-acetamido-N-benzyl-2-(N-(N-methylhydroxyamino))acetamide or the D or L steroisomer thereof.

63. The composition according to claim 42 wherein the compound is 2-acetamido-N-benzyl-2-(N-(N,O-dimethylhydroxyamino)acetamide or the D or L stereoisomer thereof.

64. The composition according to claim 42 wherein the compound is 2-acetamido-N-benzyl-2-(N-isoxazolidino) acetamide or the D or L isomer thereof.

65. The composition according to claim 42 wherein the compound is 2-acetamido-N-benzyl-2-(2-pyridyl)acetamide or the D or L steroisomer.

66. The composition according to claim 42 wherein the compound is 2-acetamido-N-benzyl-2-(1-pyrazolyl)acetamido or the D or L stereoisomer thereof.

67. A compound of the formula

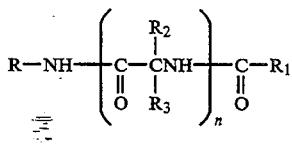 (I)

and pharmaceutically acceptable salts thereof wherein

R is aryl, aryl lower alkyl, heterocyclic or heterocyclic lower alkyl, cycloalkyl, lower cycloalkyl, or lower alkyl, wherein R is unsubstituted or is substituted with at least one electron withdrawing group or an electron donating group;

$R_1$ is hydrogen or lower alkyl and $R_1$ is unsubstituted or substituted with at least one electron withdrawing substituent or at least one electron donating substituent;

$R_2$ and $R_3$ are independently hydrogen, lower alkenyl, lower alkynyl, heterocyclic, heterocyclic lower alkyl, lower alkyl heterocyclic, lower cycloalkyl, lower cycloalkyl lower alkyl, lower alkyl, or Z-Y wherein $R_2$ and $R_3$ may be unsubstituted or substituted with at least one electron withdrawing group or electron donating group;

Z is O, $S(O)_a$ or $NR_4$;

Y is hydrogen, lower alkyl, aryl, aryl lower alkyl, lower alkenyl, lower alkynyl, halo, heterocyclic or heterocyclic lower alkyl, cycloalkyl, cycloalkyl lower alkyl and Y may be unsubstituted or substituted with an electron donating group or an electron withdrawing group provided that when Y is halo, Z is a chemical bond; or ZY taken together is $NR_4NR_5R_7$, $NR_4OR_5$, $ONR_4R_7$, $SNR_4R_7$, $NR_4SR_7$,

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group;

$R_7$ is $R_6$, $COOR_8$ or $COR_8$;

$R_8$ is hydrogen or lower alkyl or aryl lower alkyl;

n is 1-4 and a is 1-3.

68. The compound according to claim 67 wherein one of $R_2$ and $R_3$ is other than hydrogen.

69. The compound according to claim 67 wherein n is 1.

70. The compound according to claim 67 wherein one of $R_2$ and $R_3$ is hydrogen and the other is furyl, pyrrolyl, phenyl, benzyloxycarbonyl, hydrazino, isoxozolidino, N, O-dimethylhydroxyamino, N-methylhydroxyamino, N-methoxy amino, ethylamino or methylamino.

71. The compound according to claim 67 wherein $R_1$ is lower alkyl.

72. The compound according to claim 67 wherein $R_1$ is methyl.

73. The compound according to claim 67 wherein R is aryl lower alkyl.

74. The compound according to claim 67 wherein R is benzyl.

75. The composition according to claim 67 which is in the D form, the L form, a mixture of the (D, L) form or a racemic mixture of the (D, L) form.

76. The compound according to claim 67 wherein one of $R_2$ and $R_3$ is hydrogen and the other is heterocyclic.

77. The compound according to claim 67 wherein heterocyclic has the formula

 XI wherein n is 0 or 1

A, E, L and J are independently CH or a heteroatom selected from the group consisting of O, N and S G is CH or a heteroatom selected from the group consisting of N, O and S but when n is O, G is CH or a heteroatom selected from the group consisting of NH, O and S, with the proviso that at most two of A, E, L, J and G are heteroatoms.

78. The compound according to claim 77 wherein one of A, B, L, J and G is a heteroatom.

79. The compound according to claim 77 wherein $R_2$ is heterocyclic if furyl, thienyl, pyrrolyl, pyrazolyl, isoxazolidinyl or pyridyl.

80. The compound according to claim 67 wherein one of $R_2$ and $R_3$ is hydrogen and the other is N-hydroxylamino, lower alkoxyamino, N-lower alkylhydroxy, or N-lower alkyl-O-lower alkyl hydroxyamino.

81. The compound according to claim 67 wherein one of $R_2$ and $R_3$ is hydrogen and the other is lower alkoxy, amino, lower alkylamino or dilower alkylamino.

82. A compound of the formula

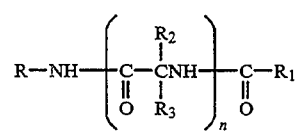 (I)

wherein

R is aryl, aryl lower alkyl, heterocyclic or heterocyclic lower alkyl which is unsubstituted or substituted with at least one electron withdrawing group or at least one electron donating group;

$R_1$ is hydrogen or lower alkyl which is unsubstituted or substituted with at least one electron withdrawing group or one electron donating group;

$R_2$ and $R_3$ are independently hydrogen, lower alkyl, lower alkenyl, lower alkynyl, Z-Y or a heterocyclic group each which may be unsubstituted or substituted with at least one electron withdrawing group or one electron donating group, with the proviso that $R_2$ and $R_3$ cannot both be hydrogen;

Z is O, S, $NR_4$, or a chemical bond;

Y is hydrogen, lower alkyl, aryl, aryl lower alkyl, lower alkenyl, lower alkynyl or halo, and Y may be unsubstituted or substituted with an electron donating group or an electron withdrawing group, provided that when Y is halo, then Z is a chemical bond; or ZY taken together is $NR_4NR_5R_6$, $NR_4OR_5$, $SNR_4R_5$, or $NR_4SR_5$, $R_4$, $R_5$ and $R_6$ are independently hydrogen, lower alkyl, aryl, aryl lower alkyl, lower alkenyl or lower alkynyl, wherein $R_4$, $R_5$ and $R_6$ may be unsubstituted or substituted with an electron withdrawing group or an electron donating group; and n is 1–4.

83. The compound according to claim 82 wherein $R_1$ is methyl.

84. The compound according to claim 82 wherein R is unsubstituted or substituted aryl lower alkyl.

85. The compound according to claim 84 wherein R is benzyl which is either unsubstituted or substituted with fluoro.

86. The compound according to claim 82 wherein the electron withdrawing group is halo, nitro, lower alkanoyl, aryloyl, aryl lower alkanoyl, carboxy, carbalkoxy, carboxamido, cyano, sulfonyl, sulfoxide, heterocyclic, guanidine or quaternary ammonium.

87. The compound according to claim 82 wherein the electron donating group is hydroxy, lower alkoxy, lower alkyl, amino, lower alkylamino, di(loweralkyl)amino, or phenoxy.

88. The compound according to claim 82 wherein one of $R_2$ and $R_3$ is hydrogen and the other is lower alkenyl or lower alkynyl.

89. The compound according to claim 88 wherein one of $R_2$ and $R_3$ is 2-propenyl.

90. The compound according to claim 82 wherein one of $R_2$ and $R_3$ is hydrogen and the other is Z-Y.

91. The compound according to claim 90 wherein ZY is lower alkoxy, aryloxy, thioloweralkoxy, amino, thioaryloxy, lower alkylamino, di(loweralkyl)amino, arylamino, hydrazino, lower alkylhydrazino, N-phenylhydrazino or hydroxylamino.

92. The compound according to claim 82 wherein one of $R_2$ and $R_3$ is hydrogen and the other is heterocyclic or heterocyclic lower alkyl.

93. The compound according to claim 92 wherein one of $R_2$ and $R_3$ is thienyl, pyridyl, pyrazinyl, furyl, pyrrolyl, methylfuryl, benzofuryl, benzothienyl, indolyl, isoxazolidinyl, methylpyrrolyl, or morpholino and the other is hydrogen.

94. The compound according to claim 93 wherein R is benzyl, 2-fluorobenzyl, 3-fluorobenzyl, or 4-fluorobenzyl and one of $R_2$ and $R_3$ is hydrogen and the other is furyl.

95. The compound according to claim 82 wherein n is 1.

96. The compound according to claim 82 wherein n is 1 and $R_1$ is methyl.

97. The compound according to claim 82 wherein n is 1 and R is unsubstituted or substituted aryl lower alkyl.

98. The compound according to claim 97 wherein R is benzyl which is either unsubstituted or substituted with fluoro.

99. The compound according to claim 82 wherein n is 1 and the electron withdrawing group is halo, nitro, lower alkanoyl, aryloyl, aryl lower alkanoyl, carboxy, carbalkoxy, carboxamido, cyano, sulfonyl, sulfoxide, heterocyclic, guanidine or quaternary ammonium.

100. The compound according to claim 82 wherein n is 1 and the electron donating group is hydroxy, lower alkoxy, lower alkyl, amino, lower alkylamino, di(loweralkyl)amino, or phenoxy, thiol, lower alkylmercapto or disulfide.

101. The compound according to claim 82 wherein n is 1 and one of $R_2$ and $R_3$ is hydrogen and the other is lower alkenyl or lower alkynyl.

102. The compound according to claim 101 wherein one of $R_2$ and $R_3$ is 2-propenyl and the other is hydrogen.

103. The compound according to claim 82 wherein n is 1 and one of $R_2$ and $R_3$ is hydrogen and the other is Z-Y.

104. The compound according to claim 103 wherein ZY is lower alkoxy, aryloxy, thioloweralkoxy, thioaryloxy, lower alkylamino, di(loweralkyl)amino, arylamino, hydrazino, lower alkylhydrazino, N-phenylhydrazino or hydroxylamino.

105. The compound according to claim 82 wherein n is 1 and one of $R_2$ and $R_3$ is hydrogen and the other is heterocyclic or heterocyclic lower alkyl.

106. The compound according to claim 105 wherein one of $R_2$ and $R_3$ is hydrogen and the other is thienyl, furyl, pyrrolyl, methylfuryl, benzofuryl, benzothienyl, indolyl, pyridyl, pyrazinyl, methylpyrrolyl, or morpholino.

107. The compound according to claim 82 wherein n is 1 and R is benzyl, 2-fluorobenzyl, 3-fluorobenzyl, or 4-fluorobenzyl and one of $R_2$ and $R_3$ is hydrogen and the other is furyl.

108. The stereoisomers of the compound of claim 82 or the mixture thereof or the racemic mixture thereof.

109. The D or L stereoisomer of the compound of claim 95 or the mixture thereof or the racemate thereof.

110. D or L-N-acetyl-phenylglycine-N'-benzylamide, or the (D,L) mixture thereof.

111. D or L α-acetamido-N-benzyl-3-thiopheneacetamide, or the (D,L) mixture thereof.

112. D or L α-acetamido-N-benzyl-2-thiopheneacetamide, or the (D,L) mixture thereof.

113. The compound according to claim 82 which is D or L-α-acetamido-N-benzyl-2-furanacetamide.

114. The compound according to claim 82 which is D or L-α-acetamido-N-benzyl-2-pyrroleacetamide.

115. The compound according to claim 82 which is or L-2-acetamido-N-benzyl-2-ethoxy-acetamide, D or L-2-acetamido-N-benzyl-2-methoxyacetamide, D or L-α-acetamido-N-benzyl-2-(5-methylfuran-)acetamide, D or L-α-acetamido-N-benzyl-2-benzo[b]thiopheneacetamide, or D or L-α-acetamido-N-benzyl-3-indolacetamide, or D or L-α-acetamido-N-benzyl-2-(5-methylpyrrole) acetamide.

116. The compound according to claim 82 which is (D,L)-α-Acetamido-N-(4-fluorobenzyl)-2-furanacetamide, D-2-Acetamido-N-(4-fluorobenzyl)-2-furanacetamide; or L-α-Acetamido-N-(4-fluorobenzyl)-2-furanacetamide.

117. The compound according to claim 82 which is (D,L)-α-Acetamido-N-(3-fluorobenzyl)-2-furanacetamide, D-α-Acetamido-N-(3-fluorobenzyl)-2-furanacetamide; or L-2-Acetamido-N-(3-fluorobenzyl)-2-furanacetamide.

118. The compound according to claim 82 which is D- or L-α-Acetamido-N-(2-fluorobenzyl)-2-furanacetamide,
   D or L-α-Acetamido-N-(2,5-difluorobenzyl)-2-furanacetamide or
   D or L-α-Acetamido-N-(2,6-difluorobenzyl)-2-furanacetamide.

119. The D or L-α-Acetamido-2-furanacetic acid or the (D,L) mixture thereof.

120. The compound according to claim 82 which is D or L-2-acetamido-4-pentenoic acid-N-benzylamide,
   D or L-2-Acetamido-N-benzyl-2-(4-morpholino) acetamide,
   D or L-2-Acetamido-N-benzyl-2-(N-anilino) acetamide,
   D or L-2-Acetamido-N-benzyl-2-(methylamino) acetamide, or
   D or L-ethyl-2-acetamido-2-(ethylamino)acetate.

121. The composition according to claim 23, wherein R is benzyl, $R_1$ is methyl, $R_2$ is hydrogen, $R_3$ is phenyl, and n is 1 or the D or L-stereoisomer thereof;
   wherein R is benzyl, $R_1$ is methyl, $R_2$ is hydrogen and $R_3$ is 2-furyl and n is 1 or the D or L-stereoisomer thereof;
   R is 2-fluorobenzyl, $R_1$ is methyl, $R_2$ is hydrogen and $R_3$ is 2-furyl and n is 1 or the D or L-stereoisomer thereof;
   R is 3-fluorobenzyl, $R_1$ is methyl, $R_2$ is hydrogen and $R_3$ is 2-furyl and n is 1 or the D or L stereoisomer thereof; or
   R is 4-fluorobenzyl, $R_1$ is methyl, $R_2$ is hydrogen and $R_3$ is 2-furyl and n is 2 or the D or L stereoisomer thereof.

122. The compound according to claim 82 which is D or L α-Acetamide-N-(2-fluorobenzenyl)-3-furanacetamide,
   D or L α-acetamido-N-(3-fluorobenzyl)-3-furanacetamide,
   D or L α-acetamido-N-(4-fluorobenzyl)-3-furanacetamide;
   D or L α-acetamido-N-benzyl-3-furanacetamide;
   D or L 2-acetamido-N-benzyl-2-amino acetamide;
   D or L -α-acetamido-N-benzyl-2-(N,N-dimethylamino)acetamide, 2-acetamido-N-benzyl-2-(N,N,N-trimethylammonium) acetamide tetrafluoroborate,
   D or L 2-acetamido-2-benzyl-2-(N-(3-pyrazolylamino))acetamide,
   D or L 2,2-diacetamido-N-benzyl-acetamide, or
   D or L 2-acetamido-N-benzyl-2-trifluoroacetamidoacetamide.

123. The compound according to claim 82 which is 2-acetamido-N-benzyl-2-(N-hydroxyamino)acetamide or the D or L isomer thereof.

124. The compound according to claim 82 which is 2-acetamido-N-benzyl-2-(N-methoxyamino)acetamide or the D or L isomer thereof.

125. The compound according to claim 82 which is 2-acetamido-N-benzyl-2-(N-(N-methylhydroxyamino))acetamide or the D or L isomer thereof.

126. The compound according to claim 82 which is 2-acetamido-N-benzyl-2-(N-(N,O-dimethylhydroxyamino))acet amide or the D or L isomer thereof.

127. The compound according to claim 82 which is 2-acetamido-N-benzyl-2-(N-isoxazolidino)acetamide or the D or L isomer thereof.

128. The compound according to claim 82 which is 2-acetamido-N-benzyl-2-($N^2$-phenylhydrazino)acetamide.
   D or L 2-acetamido-N-benzyl-2-($N^2$-benzyloxycarbonyl-hydrazino)acetamide,
   D or L 2-acetamido-N-benzyl-2-hydroxyacetamide,
   D or L 2-acetamido-N-benzyl-2-phenoxyacetamide,
   D or L 2-acetamido-N-benzyl-2-ethylmercapto) acetamide-S-oxide or
   D or L 2-acetamido-N-benzyl-2-(ethylsulfonyl) acetamide.

129. The compound according to claim 82 which is 2-acetamido-N-benzyl-2-(2-pyridyl)acetamide.

130. The compound according to claim 82 which is 2-acetamido-N-butyl-2-(1-pyrazole)acetamide.

131. The compound according to claim 82 which is 2-acetamido-N-benzyl-2-(1-pyrrolyl)acetamide, acetamido-N-benzyl-2-(1 -imidazolyl)acetamide, 2-acetamido-N-benzyl-2-(3 -pyridyl)acetamide, 2-acetamido-N-benzyl-2-(4-pyridyl)acetamide, 2-acetamido-N-benzyl-2-(2-pyrimidinyl)acetamide, 2-acetamido-N-benzyl-2-(4-pyrimidinyl)acetamide, 2-acetamido-N-benzyl-2-(5-pyrimidinyl)acetamide, 2-acetamido-N-benzyl-2-(3-pyridazinyl)acetamide, 2-acetamido-N-benzyl-2-(4-pyridazinyl)acetamide, 2-acetamido-N-benzyl-2-(2-pyrazinyl)acetamide, 2-acetamido-N-benzyl-2-(2-thiazolyl)acetamide, 2-acetamido-N-benzyl-2-(3-oxazolyl)acetamide, 2-acetamido-N-benzyl-2-(3-isoxazolyl)acetamide, 2-acetamido-N-benzyl-2-(5-isoxazolyl)acetamide, 2-acetamido-N-benzyl-2-(3-isothiazolyl)acetamide or 2-acetamido-N-benzyl-2-(5-isothiazolyl)acetamide 132. A method of treating central nervous system disorders in animals comprising the administration to said animal an effective amount of a compound according to claim 1.

133. A method of treating central nervous system disorders in animals comprising the administration to said animal an effective amount of a compound according to claim 2.

134. A method of treating central nervous system disorders in animals comprising the administration to said animal an effective amount of a compound according to claim 23.

135. A method of treating central nervous system disorders in animals comprising the administration to said animal an effective amount of a compound according to claim 67.

136. A method of treating central nervous system disorders in animals comprising the administration to said animal an effective amount of a compound according to claim 82.

137. The method of claim 132 wherein said compound is administered in an amount from about 10 to about 100 mg/kg of body weight per day.

138. The method of claim 133 wherein said compound is administered in an amount from about 10 to about 100 mg/kg of body weight per day.

139. The method of claim 134 wherein said compound is administered in an amount from about 10 to about 100 mg/kg of body weight per day.

140. The method of claim 135 wherein said compound is administered in an amount from about 10 to about 100 mg/kg of body weight per day.

141. The method of claim 136 wherein said compound is administered in an amount from about 10 to about 100 mg/kg of body weight per day.

142. The method according to claim 135 wherein the compound administered is 2-acetamido-N-benzyl-2-(N-methoxyamino)acetamide, 2-acetamido-N-benzyl-2-(N-(N,O)-dimethylhydroxy-amino)acetamide, N-acetyl-phenylgylcine-N'-benzylamide, α-acetamido-N-benzyl-2-furanacetamide, α-acetamido-N-benzyl-2-(5-methylfuran)acetamide, α-acetamido-N-(3-fluorobenzyl)-2-furanacetamide, 2-acetamido-N-benzyl-2-(N,(N-methylhydroxyamino) acetamide, 2-acetamido-N-benzyl-2-(N-isoxazolidino)acetamide 2-acetamido-N-benzyl-2-(2-pyrroyl) acetamide, 2-acetamido-N-benzyl-2-(2-pyridyl) acetamide or 2-acetamido-N-benzyl-2-(1-pyrazolyl)acetamide or the D isomer of the compound, L isomer of the compound or a mixture of the (D,L) isomer of the compound.

143. The compound according to claim 82 which is (D)-(−)-α-Acetamido-N-benzyl-2-furanacetamide.

144. The compound according to claim 110 which is N-acetyl-D-phenylglycine-N'-benzylamide.

145. The composition according to claim 1 wherein said electron withdrawing substituent is halo, nitro, carboxy, lower alkenyl, lower alkynyl, formyl, carboxyamido, aryl, quaternary ammonium, trifluoromethyl, aryl lower alkanoyl and carbalkoxy.

146. The composition according to claim 1 wherein said electron donating substituent is hydroxy, lower alkoxy, lower alkyl, amino, lower alkylamino, di(lower alkyl)amino, phenoxy, thiol, lower alkylmercapto, or disulfide.

147. The composition according to claim 42 wherein said electron withdrawing group is halo, nitro, carboxy, lower alkenyl, lower alkynyl, formyl, carboxyamido, aryl, quaternary ammonium, trifluoromethyl, aryl lower alkanoyl and carbalkoxy.

148. The composition according to claim 42 wherein said electron donating group is hydroxy, lower alkoxy, lower alkyl, amino, lower alkylamino, di(lower alkyl)amino, phenoxy, thiol, lower alkylmercapto, or disulfide.

149. The composition according to claim 67 wherein said electron withdrawing group is halo, nitro, carboxy, lower alkenyl, lower alkynyl, formyl, carboxyamido, aryl, quaternary ammonium, trifluoromethyl, aryl lower alkanoyl, and carbalkoxy.

150. The composition according to claim 67 wherein said electron donating group is hydroxy, lower alkoxy, lower alkyl, amino, lower alkylamino, di(lower alkyl)amino, phenoxy, thiol, lower alkylmercapto, or disulfide.

* * * * *

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 4, line 16: "cycIodecyl" should read --cyclodecyl--

Column 5, line 49: "o" should read --O--

Column 6, line 12: after "hydrogen" insert --.--

Column 6, line 31: after "aralkoxycarbonylhydrazino" delete "," and insert --.--

Column 8, line 32: "$PR_4R_5R_7$" should read --$PR_4NR_5R_7$--

Column 8, line 38: "$R_6$are" should read --$R_6$ are--

Column 8, line 43: "group-and" should read --group and--

Column 11, Scheme II: on line 11, insert the following: --wherein $R_{17}=$ lower alkyl, aryl, aryl lower alkyl,--

Column 13, line 30: "$R_{16}$" should read --$R_{17}$--

Column 17, line 29: "tile" should read --the--

Column 19, line 32: "(P+I)" should read --(P+1)--

Column 20, line 22: "(P+I)" should read --(P+1)--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 20, line 37: "$^1$NMR" should read -- $^1$H NMR --
Column 21, line 63: "15I" should read --1H--
Column 23, line 22: delete -- + --
Column 23, line 33: "residue-was" should read --residue was--
Column 23, line 43: "2..29" should read --2.29--
Column 23, line 60: "mol" should read --mmol--
Column 24, line 20: "41:5" should read --41.5--
Column 24, line 56: "3]I)" should read --3H)--
Column 25, line 30: "85 .(34)" should read --85 (34)--
Column 25, line 64: "C3" should read --$C_3$--
Column 25, line 68: "$C_4$··" should read --$C_4$·--
Column 26, line 5: "cm⁻" should read -- $cm^{-1}$ --
Column 26, line 24: "C5" should read --$C_5$--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 26, line 49: "271.-13208" should read --271.13208--

Column 27, line 30: $2C_2$" should read --$2C_2\cdot$--

Column 27, line 31: "17 1.57" should read --171.57--

Column 27, line 65: "$C_{3,,}$" should read --$C_3'$--

Column 27, line 66: "2C2" should read --$2C_2$--

Column 27, line 67: "$C_{2,,}$" should read --$C_2'$--

Column 28, line 2: "$cm^-$" should read --$cm^{-1}$--

Column 28, line 24: "($Na_2SO_4$" should read --($Na_2SO_4$)--

Column 28, line 44: after "(5)" insert --,--

Column 28, line 67: "chloroform/n(ethanol)" should read --chloroform/methanol)--

Column 29, line 12: "$C_{7,,}a$" should read --$C_7,a$--

Column 29, line 66: "2.00 a" should read --2.00 g--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

```
Column 32, line 64:    "Marking"   should read  --Making--
Column 33, line 13:    "820"       should read  --820,--
Column 33, line 32:    after "solution" insert --of--
Column 33, line 42:    "15.4G"     should read  --15.46--

Column 35, line 61:    "169.0:2"   should read  --169.02--
Column 36, line 10:    "9..82"     should read  --2.82--
Column 36, line 17:    "By"        should read  --by--
Column 37, line 44:    "SiO2"      should read  --$SiO_2$--
Column 38, line 23:    "SiO2"      should read  --$SiO_2$--
Column 38, line 26:    "4H"        should read  --4H),--
Column 38, line 37:    "CHCl8"     should read  --$CHCl_3$ --
Column 38, line 47:    "11.87"     should read  --113.87--
Column 38, line 61:    "Rental"    should read  --mmol--
Column 39, line 65:    "0.(30 g"   should read  --0.60 g--
```

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 40, line 40: "$O_2$59.71%" should read --$O_2$ 59.71%--
Column 41, line 1: "61" should read --51--
Column 41, line 48: "(100) (20)" should read --(100), 122 (20)--
Column 42, line 2: "(798" should read --(7%--
Column 42, line 17: "It;" should read --H--
Column 43, line 25: "$H_{18}$" should read --$H_{15}$--
Column 43, line 41: "59.5G%" should read --59.56%--
Column 43, line 67: "rental" should read --mmol--
Column 44, line 40: "1.520" should read --1520--
Column 48, line 10: "18.9,1," should read --48.94,--
Column 48, line 13: "1470." should read --1470,--
Column 48, line 14: "740,700,610" should read --740, 700, 610--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 48, line 36: "hydroxyacetamido" should read --hydroxyacetamide--

Column 48, line 56: "730,690" should read --730, 690--

Column 48, line 61: "59.2,1%" should read --59.24%--

Column 48, line 63: "62" should read --67--

Column 48, line 65: "synthesis" should read --Synthesis--

Column 49, line 8: "staple" should read --sample--

Column 49, line 55: "760,700" should read --760, 700--

Column 50, line 1: "(6 mL." should read --(6 mL).--

Column 51, line 17: "(M++I)" should read --($M^+$+1)--

Column 52, line 1: "45.,t3" should read --45.43--

Column 52, line 20: "(6 ml,)" should read --(6 mL)--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 52, line 22: "(-50 mL)" should read --(∼ 50 mL)--

Column 52, line 63: "($2C_2$," should read --($2C_2$--

Column 53, line 43: "nap" should read --mp--

Column 54, line 12: "of2" should read --of 2--

Column 54, line 55: "ml." should read --mL--

Column 54, line 63: "(2-pyridone)" should read --(2'-pyridone)--

Column 55, line 43: "126.8..6" should read --126.80--

Column 55, line 47: "conformed" should read --confirmed--

Column 56, line 10: "$CH_3OH$]" should read --$CH_3OH$/--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 56, line 20: "138.8,140.1" should read --138.8, 140.1--

Column 57, line 25: "fox" should read --for--
Column 58, line 17: "arid" should read --and--
Column 59, line 43: after "∼30" insert -- ‡ --
Column 59, line 50: before "∼100" insert -- ‡ --and after "∼100" insert -- ‡ --
Column 61, line 6: before "∼100" insert -- ‡ --
Column 61, line 11: "28.4)" should read --28.4)*--
Column 61, line 15: "3.9)" should read --3.9}*--

Column 65, line 36, Claim 39: "p" should read --D--
Column 65, line 67, Claim 41: "p" should read --D--

UNITED STATES PATENT AND TRADEMARK OFFICE
CERTIFICATE OF CORRECTION

PATENT NO. : 5,378,729
DATED : January 3, 1995
INVENTOR(S) : Harold L. Kohn, et al.

It is certified that error appears in the above-indentified patent and that said Letters Patent is hereby corrected as shown below:

Column 66, line 39, Claim 42: "S(O)," should read --S(O)a,--

Column 68, line 5, Claim 53: delete --isoxazoldino,--

Column 70, line 31, Claim 79: "if" should read --is--

Column 72, line 44, Claim 115: "which is or" should read --which is D or--

Column 73, line 43, Claim 122: "2-acetamido" should read -- α-acetamido --

Column 73, line 48, Claim 122: "2-benzyl" should read --N-benzyl--

Signed and Sealed this

Eleventh Day of June, 1996

BRUCE LEHMAN

*Attest:*

*Attesting Officer*     *Commissioner of Patents and Trademarks*